US011306140B2

(12) United States Patent
Dana et al.

(10) Patent No.: US 11,306,140 B2
(45) Date of Patent: Apr. 19, 2022

(54) THERAPEUTICS FOR OCULAR IMMUNOINFLAMMATORY DISEASES

(71) Applicant: The Schepens Eye Research Institute, Inc., Boston, MA (US)

(72) Inventors: Reza Dana, Newton, MA (US); Sunil Chauhan, Cambridge, MA (US); Yihe Chen, Somerville, MA (US)

(73) Assignee: The Schepens Eye Research Institute, Inc., Boston, MA (US)

( * ) Notice: Subject to any disclaimer, the term of this patent is extended or adjusted under 35 U.S.C. 154(b) by 17 days.

(21) Appl. No.: 16/068,300

(22) PCT Filed: Jan. 6, 2017

(86) PCT No.: PCT/US2017/012547
§ 371 (c)(1),
(2) Date: Jul. 5, 2018

(87) PCT Pub. No.: WO2017/120479
PCT Pub. Date: Jul. 13, 2017

(65) Prior Publication Data
US 2019/0008765 A1     Jan. 10, 2019

Related U.S. Application Data

(60) Provisional application No. 62/275,946, filed on Jan. 7, 2016.

(51) Int. Cl.
*C07K 16/24* (2006.01)
*A61P 27/04* (2006.01)
*A61K 39/00* (2006.01)
*A61L 27/54* (2006.01)
*A61K 9/00* (2006.01)

(52) U.S. Cl.
CPC .......... *C07K 16/244* (2013.01); *A61K 9/0048* (2013.01); *A61L 27/54* (2013.01); *A61P 27/04* (2018.01); *A61K 9/0051* (2013.01); *A61K 2039/505* (2013.01); *A61L 2300/426* (2013.01); *A61L 2430/16* (2013.01); *C07K 2317/76* (2013.01)

(58) Field of Classification Search
CPC ... C07K 2317/76; C07K 16/244; A61P 27/02; A61K 39/3955; A61K 39/395; A61K 39/00114
See application file for complete search history.

(56) References Cited

U.S. PATENT DOCUMENTS

| 4,816,567 A | 3/1989 | Cabilly et al. |
| 5,641,673 A | 6/1997 | Haseloff et al. |
| 5,795,966 A * | 8/1998 | Grabstein ............ C07K 16/244 |
| | | 530/388.23 |
| 2006/0110429 A1 | 5/2006 | Reiff et al. |
| 2011/0104236 A1 * | 5/2011 | Dana .................... C07K 16/244 |
| | | 424/429 |
| 2011/0200585 A1 | 8/2011 | Kirby et al. |
| 2013/0045927 A1 * | 2/2013 | Dana .................... A61K 9/0048 |
| | | 514/20.8 |

FOREIGN PATENT DOCUMENTS

| EP | 0 794 441 A2 | 9/1997 |
| JP | 2009-539977 A | 11/2009 |
| WO | 93/11161 A1 | 6/1993 |
| WO | 2004/076620 A2 | 9/2004 |
| WO | 2007/145618 A1 | 12/2007 |
| WO | WO 2012/027546 A2 | 3/2012 |
| WO | WO 2014/107737 A2 | 7/2014 |
| WO | 2017120479 A1 | 7/2017 |

OTHER PUBLICATIONS

Palmer et al. Interleukin-7 Receptor Signaling Network: An Integrated Systems Perspective. Cellular & Molecular Immunology. 2008;5(2):79-89 (Year: 2008).*
Mishra et al. Molecular Pathways: Interleukin-15 Signaling in Health and in Cancer. Clin Cancer Res; 20(8) Apr. 15, 2014 (Year: 2014).*
Aagaard et al. RNAi therapeutics: Principles, prospects and challenges. Advanced Drug Delivery Reviews 59 (2007) 75-86 (Year: 2007).*
Warzocha et al. Antisense Strategy: Biological Utility and Prospects in the Treatment of Hematological Malignancies. Leukemia and Lymphoma, vol. 24. 1997,pp. 267-281 (Year: 1997).*
Bowie et al. Deciphering the Message in Protein Sequences: Tolerance to Amino Acid Substitutions. Science, 1990, 247:1306-1310 (Year: 1990).*
Burgess et al. Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue. J. Cell Biol. 111:2129-2138, 1990 (Year: 1990).*
Lazar et al. Transforming Growth Factor ox: Mutation of Aspartic Acid 47 and Leucine 48 Results in Different Biological Activities. Mol. Cell. Biol., 8:1247-1252, 1988 (Year: 1988).*
Bork. Powers and Pitfalls in Sequence Analysis: The 70% Hurdle. Genome Research, 2000, 10:398-400 (Year: 2000).*
Vajdos et al. Comprehensive Functional Maps of the Antigenbinding Site of an Anti-ErbB2 Antibody Obtained with Shotgun Scanning Mutagenesis. J Mol Biol. Jul. 5, 2002;320(2):415-28 (Year: 2002).*

(Continued)

*Primary Examiner* — Vanessa L. Ford
*Assistant Examiner* — Sandra E Dillahunt
(74) *Attorney, Agent, or Firm* — Mintz Levin Cohn Ferris Glovsky and Popeo, P.C.; Ingrid A. Beattie

(57) ABSTRACT

Methods and compositions for reducing the activity or number of memory Th17 cells in ocular tissue, and for treatment and/or prevention of ocular immunoinflammatory diseases are described.

9 Claims, 8 Drawing Sheets
Specification includes a Sequence Listing.

(56) References Cited

OTHER PUBLICATIONS

Brown et al. Tolerance to Single, but Not Multiple, Amino Acid Replacements in Antibody VH CDR2. J Immunol. May 1996; 156(9): 3285-91 (Year: 1996).*
Guido et al. Virtual Screening and Its Integration with Modern Drug Design Technologies. Curr Med Chem. 2008; 15(1):37-46 (Year: 2008).*
Clark et al. Discovery and Development of Janus Kinase (JAK) Inhibitors for Inflammatory Diseases. J. Med. Chem., 2014, 57 (12), pp. 5023-5038 (Year: 2014).*
Tempest-Roe et al.Local therapies for inflammatory eye disease in translation: past, present and future. BMC Ophthalmology 2013, 13:39 (Year: 2013).*
Barata et al. Flip the coin: IL-7 and IL-7R in health and disease. Nature Immunology, 2019; 20:1584-1593. (Year: 2019).*
Lin et al. The Future of Uveitis Treatment. Opthalmology, 2014; 121:365-376 (Year: 2014).*
Guex-Crosier et al. Humanized Antibodies Against the a-Chain of the IL-2 Receptor and Against the B-Chain Shared by the IL-2 and IL-15 Receptors in a Monkey Uveitis Model of Autoimmune Diseases. Journal of Immunology, 1997, 158: 452-458 (Year: 1997).*
Hui et al. Tofacitinib (CP-690,550), a Janus Kinase Inhibitor for Dry Eye Disease. Ophthalmology 2012;119:1328-1335 (Year: 2012).*
Chen et al. A Comparison of Cyclosporine 0.05% Ophthalmic Emulsion Versus Vehicle in Chinese Patients with Moderate to Severe Dry Eye Disease: An Eight-Week, Multicenter, Randomized, Double-Blind, Parallel-Group Trial. Journal of Ocular Pharmacology and Therapeutics. Aug. 2010, 361-366 (Year: 2010).*
Chuahan et al. Autoimmunity in Dry Eye Is Due to Resistance of Th17 to Treg Suppression. Journal of Immunology, 2009, 182: 1247-1252. (Year: 2009).*
Tempest-Roe et al. (BMC Ophthalmology 2013, 13:39 (Year: 2013).*
Barata et al. Nature Immunology, 2019; 20:1584-1593 (Year: 2019).*
Lin et al. Ophthalmology, 2014; 121:365-376 (Year: 2014).*
Guex-Crosier et al. Journal of Immunology, 1997, 158: 452-458 (Year: 1997).*
Chen et al. Journal of Ocular Pharmacology and Therapeutics, Aug. 2010; 361-366 (Year: 2010).*
Ziolkowska et al. J Immunol 2000; 164:2832-2838 (Year: 2000).*
Chuahan et al. Journal of Immunology, 2009, 182: 1247-1252 (Year: 2009).*
Chi et al., Upregulated IL-23 and IL-17 in Behcet patients with Active Uveitis, Investigative Ophthalmology & Visual Science, Jul. 1, 2008, vol. 49, No. 7, pp. 3058-3064.
Ziolkowska et al., High Levels of IL-17 in rheumatoid Arthritis Patients: IL-15 Triggers in vitro IL-17 Production via Cyclosporin A-sensitive Mechanism, J Immunol, Mar. 1, 200, vol. 164, No. 5, pp. 2832-2838.
"Cytokine Receptor Common Subunit Gamma", UniProtKB—P31785 (IL2RG_HUMAN), 17 pages.
"*Homo sapiens* Interleukin 15 (IL15), Transcript Variant 2, mRNA", NCBI Acession No. NM_172175, 4 pages.
"*Homo sapiens* Interleukin 15 (IL15), Transcript Variant 3, mRNA", NCBI accession No. NM_000585, 4 pages.
"*Homo sapiens* Interleukin 15 Receptor Subunit Alpha (IL15RA), Transcript Variant 1, mRNA", NCBI No. NM_002189, 4 pages.
"*Homo sapiens* Interleukin 15 Receptor Subunit Alpha (IL15RA), Transcript Variant 2, mRNA", NCBI accession No. NM_172200, 3 pages.
"*Homo sapiens* Interleukin 15 Receptor Subunit Alpha (IL15RA), Transcript Variant 3, mRNA", NCBI accession No. NM_001243539, 4 pages.
"*Homo sapiens* Interleukin 15 Receptor Subunit Alpha (IL15RA), Transcript Variant 4, mRNA", NCBI accession No. NM_001256765, 3 pages.
"*Homo sapiens* Interleukin 2 Receptor Subunit Beta (IL2RB), Transcript Variant 1, mRNA", NCBI accession No. NM_000878, 5 pages.

"*Homo sapiens* Interleukin 2 Receptor Subunit Gamma (IL2RG), mRNA", NCBI accession No. NM_000206.3, 5 pages.
"*Homo sapiens* Interleukin 7 (IL7), Transcript Variant 1, mRNA", NCBI accession No. NM_000880.4, 4 pages.
"*Homo sapiens* Interleukin 7 (IL7), Transcript Variant 2, mRNA", NCBI accession No. NM_001199886.1, 3 pages.
"*Homo sapiens* Interleukin 7 (IL7), Transcript Variant 3, mRNA", NCBI accession No. NM_001199887.1, 3 pages.
"*Homo sapiens* Interleukin 7 (IL7), Transcript Variant 4, mRNA", NCBI accession No. NM_001199888.1, 3 pages.
"*Homo sapiens* Interleukin 7 Receptor (IL7R), Transcript Variant 1, mRNA", NCBI accession No. NM_002185.5, 5 pages.
(Mar. 23, 2015) "Interleukin 15 Receptor, Alpha, Isoform CRA_d [*Homo sapiens*]", GenBank Accession No. EAW86418, 2 pages.
"Interleukin-15", UniProtKB—P40933 (IL15_HUMAN), 12 pages.
(May 25, 2018) "Interleukin-15 Receptor Subunit Alpha", UniProtKB—Q13261 (I15RA_HUMAN), 15 pages.
"Interleukin-2 Receptor Subunit Beta", UniProtKB—P14784 (IL2RB_HUMAN), 13 pages.
"Interleukin-7", UniProtKB—P13232 (IL7_HUMAN), 12 pages.
"Interleukin-7 Receptor Subunit Alpha", UniProtKB—P16871 (IL7RA_HUMAN), 15 pages.
Anonymous (Apr. 2007) "The Definition and Classification of Dry Eye Disease: Report of the Definition and Classification Subcommittee of the International Dry Eye Workshop (2007)", The Ocular Surface, 5(2):75-92.
Anonymous (Apr. 2007) "The Epidemiology of Dry Eye Disease: Report of the Epidemiology Subcommittee of the International Dry Eye Workshop (2007)", The Ocular Surface, 5(2):93-107.
Benoist et al. (Mar. 26, 1981) "In Vivo Sequence Requirements of the SV40 Early Promotor Region", Nature, 290(5804):304-310.
Brinster et al. (Mar. 4, 1982) "Regulation of Metallothionein-Thymidine Kinase Fusion Plasmids Injected into Mouse Eggs", Nature, 296(5852):39-42.
Brown et al. (Feb. 2009) "Value-based Medicine, Comparative Effectiveness, and Cost-effectiveness Analysis of Topical Cyclosporine for the Treatment of Dry Eye Syndrome", Arch Ophthalmol, 127(2):146-152.
Carnahan et al. (Dec. 2000) "Ocular Complications of Topical, Peri-ocular, and Systemic Corticosteroids", Current Opinion in Ophthalmology, 11(6):478-483.
Chen et al. (Jan. 2014) "Chronic Dry Eye Disease is Principally Mediated by Effector Memory Th17 Cells", Mucosal Immunology, 7(1):38-45.
Clackson et al. (Aug. 15, 1991) "Making Antibody Fragments Using Phage Display Libraries", Nature, 352(6336):624-628.
Cole et al. (Jan. 12, 1983) Journal of Cellular Biochemistry, "Monoclonal Antibodies and Cancer Therapy," pp. 77-96. https://doi.org/10.1002/jcb.240290503.
Cox et al. (Oct. 2001) "Automated Selection of Anti-protein Aptamers", Bioorganic & Medicinal Chemistry, 9(10):2525-2531.
Cox et al. (Oct. 15, 2002) "Automated Selection of Aptamers Against Protein Targets Translated in Vitro: From Gene to Aptamer", Nucleic Acids Research, e108, 30(20):14 pages.
Guex-Crosier et al. (Feb. 15, 1996) "Humanized Anti-Il-2 and Anti-Il-15 Receptor Antibodies in the Treatment of Uyeoretinitis in a Monkey Model", Investigative Ophthalmology & Visual Science, 1 page.
Hollinger et al. (Jul. 1993) ""Diabodies": Small Bivalent and Bispecific Antibody Fragments", Proceedings of the National Academy of Sciences of the United States of America, 90(14):6444-6448.
Kang et al. (Jul. 2011) "Interleukin-17 in Various Ocular Surface Inflammatory Diseases", Journal of Korean medical science, 26(7):938-944.
Kohler et al. (Aug. 7, 1975) "Continuous Cultures of Fused Cells Secreting Antibody of Predefined Specificity", Nature, 256(5517):495-497.
Kozbor et al. (Mar. 1983) "The Production of Monoclonal Antibodies from Human Lymphocytes", Immunology Today, 4(3):72-79.

(56) References Cited

OTHER PUBLICATIONS

Lemp (Oct. 1995) "Report of the National Eye Institute/Industry Workshop on Clinical Trials in Dry Eyes", CLAO Journal, 21(4):221-232.

Ludwig (Nov. 3, 2005) "The Use of Mucoadhesive Polymers in Ocular Drug Delivery", Advanced Drug Delivery Reviews, 57(11):1595-1639.

Marks et al. (Dec. 5, 1991) "By-Passing Immunization: Human Antibodies from V-Gene Libraries Displayed on Phage", Journal of Molecular Biology, 222(3):581-597.

Martinsen et al. (Jan. 5, 1989) "Alginate as Immobilization Material: I. Correlation between Chemical and Physical Properties of Alginate Gel Beads", Biotechnology and Bioengineering, 33(1):79-89.

Miljanović et al. (Mar. 2007) "Impact of Dry Eye Syndrome on Vision-Related Quality of Life", Am J Ophthalmol., 143(3):409-415.

Neves et al. (Dec. 2010) "Defining the Secondary Structural Requirements of a Cocaine-binding Aptamer by a Thermodynamic and Mutation Study", Biophysical Chemistry, 153(1):9-16.

Pluckthun (1994) "Antibodies from *Escherichia coli*", The Pharmacology of Monoclonal Antibodies, 113:269-315.

Wagner et al. (Mar. 1981) "Nucleotide Sequence of the Thymidine Kinase Gene of Herpes Simplex Virus Type 1", Proceedings of the National Academy of Sciences of the United States of America, 78(3):1441-1445.

Yamamoto et al. (Dec. 1980) "Identification of a Functional Promoter in the Long Terminal Repeat of Rous Sarcoma Virus", Cell, 22(3):787-797.

Yoshimura et al. (Jan. 22, 2009) "Involvement of Th17 Cells and the Effect of anti-IL-6 Therapy in Autoimmune Uveitis", Rheumatology, 48(4):347-354.

Zapata et al. (Oct. 1995) "Engineering Linear F(ab')2 Fragments for Efficient Production in *Escherichia coli* and Enhanced Anti-Proliferative Activity", Protein Engineering, 8(10):1057-1062.

Chauhan et al. (Jul. 2009) "Role of Th17 Cells in the Immunopathogenesis of Dry Eye Disease", Mucosal Immunology, 2(4):375-376.

* cited by examiner

SEQUENCE LISTING

<160> NUMBER OF SEQ ID NOS: 38

<210> SEQ ID NO 1
<211> LENGTH: 177
<212> TYPE: PRT
<213> ORGANISM: Homo sapiens

<400> SEQUENCE: 1

```
Met Phe His Val Ser Phe Arg Tyr Ile Phe Gly Leu Pro Pro Leu Ile
1               5                   10                  15

Leu Val Leu Leu Pro Val Ala Ser Ser Asp Cys Asp Ile Glu Gly Lys
            20                  25                  30

Asp Gly Lys Gln Tyr Glu Ser Val Leu Met Val Ser Ile Asp Gln Leu
        35                  40                  45

Leu Asp Ser Met Lys Glu Ile Gly Ser Asn Cys Leu Asn Asn Glu Phe
    50                  55                  60

Asn Phe Phe Lys Arg His Ile Cys Asp Ala Asn Lys Glu Gly Met Phe
65                  70                  75                  80

Leu Phe Arg Ala Ala Arg Lys Leu Arg Gln Phe Leu Lys Met Asn Ser
                85                  90                  95
```

Thr Gly Asp Phe Asp Leu His Leu Leu Lys Val Ser Glu Gly Thr Thr
                100                 105                 110

Ile Leu Leu Asn Cys Thr Gly Gln Val Lys Gly Arg Lys Pro Ala Ala
            115                 120                 125

Leu Gly Glu Ala Gln Pro Thr Lys Ser Leu Glu Glu Asn Lys Ser Leu
    130                 135                 140

Lys Glu Gln Lys Lys Leu Asn Asp Leu Cys Phe Leu Lys Arg Leu Leu
145                 150                 155                 160

Gln Glu Ile Lys Thr Cys Trp Asn Lys Ile Leu Met Gly Thr Lys Glu
                165                 170                 175

His

<210> SEQ ID NO 2
<211> LENGTH: 133
<212> TYPE: PRT
<213> ORGANISM: Homo sapiens

<400> SEQUENCE: 2

Met Phe His Val Ser Phe Arg Tyr Ile Phe Gly Leu Pro Pro Leu Ile
1               5                   10                  15

Leu Val Leu Leu Pro Val Ala Ser Ser Asp Cys Asp Ile Glu Gly Lys
            20                  25                  30

Asp Gly Lys Gln Tyr Glu Ser Val Leu Met Val Ser Ile Asp Gln Leu
        35                  40                  45

Leu Asp Ser Met Lys Glu Ile Gly Ser Asn Cys Leu Asn Asn Glu Phe
    50                  55                  60

Asn Phe Phe Lys Arg His Ile Cys Asp Ala Asn Lys Val Lys Gly Arg
65                  70                  75                  80

Lys Pro Ala Ala Leu Gly Glu Ala Gln Pro Thr Lys Ser Leu Glu Glu
                85                  90                  95

Asn Lys Ser Leu Lys Glu Gln Lys Lys Leu Asn Asp Leu Cys Phe Leu
            100                 105                 110

Lys Arg Leu Leu Gln Glu Ile Lys Thr Cys Trp Asn Lys Ile Leu Met
        115                 120                 125

Gly Thr Lys Glu His
    130

<210> SEQ ID NO 3
<211> LENGTH: 64
<212> TYPE: PRT
<213> ORGANISM: Homo sapiens

<400> SEQUENCE: 3

Met Lys Glu Ile Gly Ser Asn Cys Leu Asn Asn Glu Phe Asn Phe Phe
1               5                   10                  15

Lys Arg His Ile Cys Asp Ala Asn Lys Glu Glu Asn Lys Ser Leu Lys
            20                  25                  30

Glu Gln Lys Lys Leu Asn Asp Leu Cys Phe Leu Lys Arg Leu Leu Gln
        35                  40                  45

Glu Ile Lys Thr Cys Trp Asn Lys Ile Leu Met Gly Thr Lys Glu His
    50                  55                  60

<210> SEQ ID NO 4
<211> LENGTH: 2089
<212> TYPE: DNA
<213> ORGANISM: Homo sapiens

<400> SEQUENCE: 4

```
acatccgcgg caacgcctcc ttggtgtcgt ccgcttccaa taacccagct tgcgtcctgc      60
acacttgtgg cttccgtgca cacattaaca actcatggtt ctagctccca gtcgccaagc     120
gttgccaagg cgttgagaga tcatctggga agtcttttac ccagaattgc tttgattcag     180
gccagctggt ttttcctgcg gtgattcgga aattcgcgaa ttcctctggt cctcatccag     240
gtgcgcggga agcaggtgcc caggagagag gggataatga agattccatg ctgatgatcc     300
caaagattga acctgcagac caagcgcaaa gtagaaactg aaagtacact gctggcggat     360
cctacggaag ttatggaaaa ggcaaagcgc agagccacgc cgtagtgtgt gccgcccccc     420
ttgggatgga tgaaactgca gtcgcggcgt gggtaagagg aaccagctgc agagatcacc     480
ctgcccaaca cagactcggc aactccgcgg aagaccaggg tcctgggagt gactatgggc     540
ggtgagagct tgctcctgct ccagttgcgg tcatcatgac tacgcccgcc tcccgcagac     600
catgttccat gtttctttta ggtatatctt tggacttcct cccctgatcc ttgttctgtt     660
gccagtagca tcatctgatt gtgatattga aggtaaagat ggcaaacaat atgagagtgt     720
tctaatggtc agcatcgatc aattattgga cagcatgaaa gaaattggta gcaattgcct     780
gaataatgaa tttaactttt ttaaaagaca tatctgtgat gctaataagg aaggtatgtt     840
tttattccgt gctgctcgca agttgaggca atttcttaaa atgaatagca ctggtgattt     900
tgatctccac ttattaaaag tttcagaagg cacaacaata ctgttgaact gcactggcca     960
ggttaaagga agaaaaccag ctgccctggg tgaagcccaa ccaacaaaga gtttggaaga    1020
aaataaatct ttaaaggaac agaaaaaact gaatgacttg tgtttcctaa agagactatt    1080
acaagagata aaaacttgtt ggaataaaat tttgatgggc actaaagaac actgaaaaat    1140
atggagtggc aatatagaaa cacgaacttt agctgcatcc tccaagaatc tatctgctta    1200
tgcagttttt cagagtggaa tgcttcctag aagttactga atgcaccatg gtcaaaacgg    1260
attagggcat ttgagaaatg catattgtat tactagaaga tgaatacaaa caatggaaac    1320
tgaatgctcc agtcaacaaa ctatttctta tatatgtgaa catttatcaa tcagtataat    1380
tctgtactga tttttgtaag acaatccatg taaggtatca gttgcaataa tacttctcaa    1440
acctgtttaa atatttcaag acattaaatc tatgaagtat ataatggttt caaagattca    1500
aaattgacat tgctttactg tcaaaataat tttatggctc actatgaatc tattatactg    1560
tattaagagt gaaaattgtc ttcttctgtg ctggagatgt tttagagtta acaatgatat    1620
atggataatg ccggtgagaa taagagagtc ataaacctta agtaagcaac agcataacaa    1680
ggtccaagat acctaaaaga gatttcaaga gatttaatta atcatgaatg tgtaacacag    1740
tgccttcaat aaatggtata gcaaatgttt tgacatgaaa aaggacaatt tcaaaaaaaa    1800
taaaataaaa taaaaataaa ttcacctagt ctaaggatgc taaaccttag tactgagtta    1860
cattgtcatt tatatagatt ataacttgtc taaataagtt tgcaatttgg gagatatatt    1920
tttaagataa taatatatgt ttacctttta attaatgaaa tatctgtatt taattttgac    1980
actatatctg tatataaaat atttttcatac agcattacaa attgcttact ttggaataca    2040
tttctccttt gataaaataa atgagctatg tattaaaaaa aaaaaaaa                 2089
```

<210> SEQ ID NO 5
<211> LENGTH: 1957
<212> TYPE: DNA
<213> ORGANISM: Homo sapiens

<400> SEQUENCE: 5

-continued

| | |
|---|---|
| acatccgcgg caacgcctcc ttggtgtcgt ccgcttccaa taacccagct tgcgtcctgc | 60 |
| acacttgtgg cttccgtgca cacattaaca actcatggtt ctagctccca gtcgccaagc | 120 |
| gttgccaagg cgttgagaga tcatctggga agtcttttac ccagaattgc tttgattcag | 180 |
| gccagctggt ttttcctgcg gtgattcgga aattcgcgaa ttcctctggt cctcatccag | 240 |
| gtgcgcggga agcaggtgcc caggagagag gggataatga agattccatg ctgatgatcc | 300 |
| caaagattga acctgcagac caagcgcaaa gtagaaactg aaagtacact gctggcggat | 360 |
| cctacggaag ttatggaaaa ggcaaagcgc agagccacgc cgtagtgtgt gccgcccccc | 420 |
| ttgggatgga tgaaactgca gtcgcggcgt gggtaagagg aaccagctgc agagatcacc | 480 |
| ctgcccaaca cagactcggc aactccgcgg aagaccaggg tcctgggagt gactatgggc | 540 |
| ggtgagagct tgctcctgct ccagttgcgg tcatcatgac tacgcccgcc tcccgcagac | 600 |
| catgttccat gtttctttta ggtatatctt tggacttcct cccctgatcc ttgttctgtt | 660 |
| gccagtagca tcatctgatt gtgatattga aggtaaagat ggcaaacaat atgagagtgt | 720 |
| tctaatggtc agcatcgatc aattattgga cagcatgaaa gaaattggta gcaattgcct | 780 |
| gaataatgaa tttaactttt ttaaaagaca tatctgtgat gctaataagg ttaaaggaag | 840 |
| aaaaccagct gccctgggtg aagcccaacc aacaaagagt ttggaagaaa ataaatcttt | 900 |
| aaaggaacag aaaaaactga atgacttgtg tttcctaaag agactattac aagagataaa | 960 |
| aacttgttgg aataaaattt tgatgggcac taaagaacac tgaaaaatat ggagtggcaa | 1020 |
| tatagaaaca cgaactttag ctgcatcctc caagaatcta tctgcttatg cagttttca | 1080 |
| gagtggaatg cttcctagaa gttactgaat gcaccatggt caaaacggat tagggcattt | 1140 |
| gagaaatgca tattgtatta ctagaagatg aatacaaaca atggaaactg aatgctccag | 1200 |
| tcaacaaact atttcttata tatgtgaaca tttatcaatc agtataattc tgtactgatt | 1260 |
| tttgtaagac aatccatgta aggtatcagt tgcaataata cttctcaaac ctgtttaaat | 1320 |
| atttcaagac attaaatcta tgaagtatat aatggtttca aagattcaaa attgacattg | 1380 |
| ctttactgtc aaaataattt tatggctcac tatgaatcta ttatactgta ttaagagtga | 1440 |
| aaattgtctt cttctgtgct ggagatgttt tagagttaac aatgatatat ggataatgcc | 1500 |
| ggtgagaata agagagtcat aaaccttaag taagcaacag cataacaagg tccaagatac | 1560 |
| ctaaaagaga tttcaagaga tttaattaat catgaatgtg taacacagtg ccttcaataa | 1620 |
| atggtatagc aaatgttttg acatgaaaaa aggacaattt caaaaaaata aaataaaata | 1680 |
| aaaataaatt cacctagtct aaggatgcta aaccttagta ctgagttaca ttgtcattta | 1740 |
| tatagattat aacttgtcta aataagtttg caatttggga gatatatttt taagataata | 1800 |
| atatatgttt accttttaat taatgaaata tctgtattta attttgacac tatatctgta | 1860 |
| tataaaatat tttcatacag cattacaaat tgcttacttt ggaatacatt tctcctttga | 1920 |
| taaaataaat gagctatgta ttaaaaaaaa aaaaaaa | 1957 |

<210> SEQ ID NO 6
<211> LENGTH: 2035
<212> TYPE: DNA
<213> ORGANISM: Homo sapiens

<400> SEQUENCE: 6

| | |
|---|---|
| acatccgcgg caacgcctcc ttggtgtcgt ccgcttccaa taacccagct tgcgtcctgc | 60 |
| acacttgtgg cttccgtgca cacattaaca actcatggtt ctagctccca gtcgccaagc | 120 |
| gttgccaagg cgttgagaga tcatctggga agtcttttac ccagaattgc tttgattcag | 180 |

```
gccagctggt ttttcctgcg gtgattcgga aattcgcgaa ttcctctggt cctcatccag    240
gtgcgcggga agcaggtgcc caggagagag gggataatga agattccatg ctgatgatcc    300
caaagattga acctgcagac caagcgcaaa gtagaaactg aaagtacact gctggcggat    360
cctacggaag ttatggaaaa ggcaaagcgc agagccacgc cgtagtgtgt gccgccccc    420 ttgggatgga tgaaactgca gtcgcggcgt gggtaagagg aaccagctgc agagatcacc    480
ctgcccaaca cagactcggc aactccgcgg aagaccaggg tcctgggagt gactatgggc    540
ggtgagagct tgctcctgct ccagttgcgg tcatcatgac tacgcccgcc tcccgcagac    600
catgttccat gtttctttta ggtatatctt tggacttcct cccctgatcc ttgttctgtt    660
gccagtagca tcatctgatt gtgatattga aggtaaagat ggcaaacaat atgagagtgt    720
tctaatggtc agcatcgatc aattattgga cagcatgaaa gaaattggta gcaattgcct    780
gaataatgaa tttaacttt ttaaaagaca tatctgtgat gctaataagg aaggtatgtt    840
tttattccgt gctgctcgca agttgaggca atttcttaaa atgaatagca ctggtgattt    900
tgatctccac ttattaaaag tttcagaagg cacaacaata ctgttgaact gcactggcca    960
ggaagaaaat aaatctttaa aggaacgaaa aaaactgaat gacttgtgtt tcctaaagag   1020
actattacaa gagataaaaa cttgttggaa taaaattttg atgggcacta agaacactg   1080 aaaaatatgg agtggcaata tagaaacacg aactttagct gcatcctcca agaatctatc   1140
tgcttatgca gttttcaga gtggaatgct tcctagaagt tactgaatgc accatggtca   1200
aaacggatta gggcatttga gaaatgcata ttgtattact agaagatgaa tacaaacaat   1260
ggaaactgaa tgctccagtc aacaaactat ttcttatata tgtgaacatt tatcaatcag   1320
tataattctg tactgattt tgtaagacaa tccatgtaag gtatcagttg caataatact   1380
tctcaaacct gtttaaatat ttcaagacat taaatctatg aagtatataa tggtttcaaa   1440
gattcaaaat tgacattgct ttactgtcaa ataattttta tggctcacta tgaatctatt   1500
atactgtatt aagagtgaaa attgtcttct tctgtgctgg agatgtttta gagttaacaa   1560
tgatatatgg ataatgccgg tgagaataag agagtcataa accttaagta agcaacagca   1620
taacaaggtc caagatacct aaaagagatt tcaagagatt taattaatca tgaatgtgta   1680
acacagtgcc ttcaataaat ggtatagcaa atgttttgac atgaaaaaag gacaatttca   1740
aaaaaataaa ataaaataaa aataaattca cctagtctaa ggatgctaaa ccttagtact   1800
gagttacatt gtcatttata tagattataa cttgtctaaa taagtttgca atttgggaga   1860
tatattttta agataataat atatgtttac cttttaatta atgaaatatc tgtatttaat   1920
tttgacacta tatctgtata taaaatattt tcatacagca ttacaaattg cttactttgg   1980
aatacatttc tcctttgata aaataaatga gctatgtatt aaaaaaaaaa aaaaa          2035
```

<210> SEQ ID NO 7
<211> LENGTH: 1903
<212> TYPE: DNA
<213> ORGANISM: Homo sapiens

<400> SEQUENCE: 7

```
acatccgcgg caacgcctcc ttggtgtcgt ccgcttccaa taacccagct tgcgtcctgc     60
acacttgtgg cttccgtgca cacattaaca actcatggtt ctagctccca gtcgccaagc    120
gttgccaagg cgttgagaga tcatctggga agtcttttac ccagaattgc tttgattcag    180
gccagctggt ttttcctgcg gtgattcgga aattcgcgaa ttcctctggt cctcatccag    240
```

```
gtgcgcggga agcaggtgcc caggagagag gggataatga agattccatg ctgatgatcc    300
caaagattga acctgcagac caagcgcaaa gtagaaactg aaagtacact gctggcggat    360
cctacggaag ttatggaaaa ggcaaagcgc agagccacgc cgtagtgtgt gccgcccccc    420
ttgggatgga tgaaactgca gtcgcggcgt gggtaagagg aaccagctgc agagatcacc    480
ctgcccaaca cagactcggc aactccgcgg aagaccaggg tcctgggagt gactatgggc    540
ggtgagagct tgctcctgct ccagttgcgg tcatcatgac tacgcccgcc tcccgcagac    600
catgttccat gtttctttta ggtatatctt tggacttcct cccctgatcc ttgttctgtt    660
gccagtagca tcatctgatt gtgatattga aggtaaagat ggcaaacaat atgagagtgt    720
tctaatggtc agcatcgatc aattattgga cagcatgaaa gaaattggta gcaattgcct    780
gaataatgaa tttaactttt ttaaaagaca tatctgtgat gctaataagg aagaaaataa    840
atctttaaag gaacagaaaa aactgaatga cttgtgtttc ctaaagagac tattacaaga    900
gataaaaact tgttggaata aattttttgat gggcactaaa gaacactgaa aaatatggag    960
tggcaatata gaaacacgaa ctttagctgc atcctccaag aatctatctg cttatgcagt    1020
ttttcagagt ggaatgcttc ctagaagtta ctgaatgcac catggtcaaa acggattagg    1080
gcatttgaga aatgcatatt gtattactag aagatgaata caaacaatgg aaactgaatg    1140
ctccagtcaa caaactattt cttatatatg tgaacattta tcaatcagta taattctgta    1200
ctgatttttg taagacaatc catgtaaggt atcagttgca ataatacttc tcaaacctgt    1260
ttaaatattt caagacatta aatctatgaa gtatataatg gtttcaaaga ttcaaaattg    1320
acattgcttt actgtcaaaa taattttatg gctcactatg aatctattat actgtattaa    1380
gagtgaaaat tgtcttcttc tgtgctggag atgttttaga gttaacaatg atatatggat    1440
aatgccggtg agaataagag agtcataaac cttaagtaag caacagcata acaaggtcca    1500
agatacctaa aagagatttc aagagattta attaatcatg aatgtgtaac acagtgcctt    1560
caataaatgg tatagcaaat gttttgacat gaaaaaagga caatttcaaa aaaataaaat    1620
aaaataaaaa taaattcacc tagtctaagg atgctaaacc ttagtactga gttacattgt    1680
catttatata gattataact tgtctaaata agttttgcaat ttgggagata tatttttaag    1740
ataataatat atgtttacct tttaattaat gaaatatctg tatttaattt tgacactata    1800
tctgtatata aaatattttc atacagcatt acaaattgct tactttggaa tacatttctc    1860
ctttgataaa ataaatgagc tatgtattaa aaaaaaaaaa aaa                      1903

<210> SEQ ID NO 8
<211> LENGTH: 459
<212> TYPE: PRT
<213> ORGANISM: Homo sapiens

<400> SEQUENCE: 8

Met Thr Ile Leu Gly Thr Thr Phe Gly Met Val Phe Ser Leu Leu Gln
1               5                   10                  15

Val Val Ser Gly Glu Ser Gly Tyr Ala Gln Asn Gly Asp Leu Glu Asp
            20                  25                  30

Ala Glu Leu Asp Asp Tyr Ser Phe Ser Cys Tyr Ser Gln Leu Glu Val
        35                  40                  45

Asn Gly Ser Gln His Ser Leu Thr Cys Ala Phe Glu Asp Pro Asp Val
    50                  55                  60

Asn Thr Thr Asn Leu Glu Phe Glu Ile Cys Gly Ala Leu Val Glu Val
65                  70                  75                  80
```

Lys Cys Leu Asn Phe Arg Lys Leu Gln Glu Ile Tyr Phe Ile Glu Thr
            85                  90                  95

Lys Lys Phe Leu Leu Ile Gly Lys Ser Asn Ile Cys Val Lys Val Gly
            100                 105                 110

Glu Lys Ser Leu Thr Cys Lys Lys Ile Asp Leu Thr Thr Ile Val Lys
            115                 120                 125

Pro Glu Ala Pro Phe Asp Leu Ser Val Ile Tyr Arg Glu Gly Ala Asn
130                 135                 140

Asp Phe Val Val Thr Phe Asn Thr Ser His Leu Gln Lys Lys Tyr Val
145                 150                 155                 160

Lys Val Leu Met His Asp Val Ala Tyr Arg Gln Glu Lys Asp Glu Asn
            165                 170                 175

Lys Trp Thr His Val Asn Leu Ser Ser Thr Lys Leu Thr Leu Leu Gln
            180                 185                 190

Arg Lys Leu Gln Pro Ala Ala Met Tyr Glu Ile Lys Val Arg Ser Ile
            195                 200                 205

Pro Asp His Tyr Phe Lys Gly Phe Trp Ser Glu Trp Ser Pro Ser Tyr
            210                 215                 220

Tyr Phe Arg Thr Pro Glu Ile Asn Asn Ser Ser Gly Glu Met Asp Pro
225                 230                 235                 240

Ile Leu Leu Thr Ile Ser Ile Leu Ser Phe Phe Ser Val Ala Leu Leu
            245                 250                 255

Val Ile Leu Ala Cys Val Leu Trp Lys Lys Arg Ile Lys Pro Ile Val
            260                 265                 270

Trp Pro Ser Leu Pro Asp His Lys Lys Thr Leu Glu His Leu Cys Lys
            275                 280                 285

Lys Pro Arg Lys Asn Leu Asn Val Ser Phe Asn Pro Glu Ser Phe Leu
            290                 295                 300

Asp Cys Gln Ile His Arg Val Asp Asp Ile Gln Ala Arg Asp Glu Val
305                 310                 315                 320

Glu Gly Phe Leu Gln Asp Thr Phe Pro Gln Gln Leu Glu Glu Ser Glu
            325                 330                 335

Lys Gln Arg Leu Gly Gly Asp Val Gln Ser Pro Asn Cys Pro Ser Glu
            340                 345                 350

Asp Val Val Ile Thr Pro Glu Ser Phe Gly Arg Asp Ser Ser Leu Thr
            355                 360                 365

Cys Leu Ala Gly Asn Val Ser Ala Cys Asp Ala Pro Ile Leu Ser Ser
            370                 375                 380

Ser Arg Ser Leu Asp Cys Arg Glu Ser Gly Lys Asn Gly Pro His Val
385                 390                 395                 400

Tyr Gln Asp Leu Leu Leu Ser Leu Gly Thr Thr Asn Ser Thr Leu Pro
            405                 410                 415

Pro Pro Phe Ser Leu Gln Ser Gly Ile Leu Thr Leu Asn Pro Val Ala
            420                 425                 430

Gln Gly Gln Pro Ile Leu Thr Ser Leu Gly Ser Asn Gln Glu Glu Ala
            435                 440                 445

Tyr Val Thr Met Ser Ser Phe Tyr Gln Asn Gln
450                 455

<210> SEQ ID NO 9
<211> LENGTH: 298
<212> TYPE: PRT
<213> ORGANISM: Homo sapiens

<400> SEQUENCE: 9

-continued

```
Met Thr Ile Leu Gly Thr Thr Phe Gly Met Val Phe Ser Leu Leu Gln
1               5                   10                  15

Val Val Ser Gly Glu Ser Gly Tyr Ala Gln Asn Gly Asp Leu Glu Asp
            20                  25                  30

Ala Glu Leu Asp Asp Tyr Ser Phe Ser Cys Tyr Ser Gln Leu Glu Val
            35                  40                  45

Asn Gly Ser Gln His Ser Leu Thr Cys Ala Phe Glu Asp Pro Asp Val
50                  55                  60

Asn Thr Thr Asn Leu Glu Phe Glu Ile Cys Gly Ala Leu Val Glu Val
65                  70                  75                  80

Lys Cys Leu Asn Phe Arg Lys Leu Gln Glu Ile Tyr Phe Ile Glu Thr
                85                  90                  95

Lys Lys Phe Leu Leu Ile Gly Lys Ser Asn Ile Cys Val Lys Val Gly
            100                 105                 110

Glu Lys Ser Leu Thr Cys Lys Lys Ile Asp Leu Thr Thr Ile Val Lys
            115                 120                 125

Pro Glu Ala Pro Phe Asp Leu Ser Val Ile Tyr Arg Glu Gly Ala Asn
130                 135                 140

Asp Phe Val Val Thr Phe Asn Thr Ser His Leu Gln Lys Lys Tyr Val
145                 150                 155                 160

Lys Val Leu Met His Asp Val Ala Tyr Arg Gln Glu Lys Asp Glu Asn
                165                 170                 175

Lys Trp Thr His Val Asn Leu Ser Ser Thr Lys Leu Thr Leu Leu Gln
            180                 185                 190

Arg Lys Leu Gln Pro Ala Ala Met Tyr Glu Ile Lys Val Arg Ser Ile
            195                 200                 205

Pro Asp His Tyr Phe Lys Gly Phe Trp Ser Trp Ser Pro Ser Tyr
210                 215                 220

Tyr Phe Arg Thr Pro Glu Ile Asn Asn Ser Ser Gly Glu Met Asp Pro
225                 230                 235                 240

Ile Leu Leu Thr Ile Ser Ile Leu Ser Phe Phe Ser Val Ala Leu Leu
                245                 250                 255

Val Ile Leu Ala Cys Val Leu Trp Lys Lys Arg Ile Lys Pro Ile Val
            260                 265                 270

Trp Pro Ser Leu Pro Asp His Lys Lys Thr Leu Glu His Leu Cys Lys
            275                 280                 285

Lys Pro Arg Lys Val Ser Val Phe Gly Ala
            290                 295
```

<210> SEQ ID NO 10
<211> LENGTH: 261
<212> TYPE: PRT
<213> ORGANISM: Homo sapiens

<400> SEQUENCE: 10

```
Met Thr Ile Leu Gly Thr Thr Phe Gly Met Val Phe Ser Leu Leu Gln
1               5                   10                  15

Val Val Ser Gly Glu Ser Gly Tyr Ala Gln Asn Gly Asp Leu Glu Asp
            20                  25                  30

Ala Glu Leu Asp Asp Tyr Ser Phe Ser Cys Tyr Ser Gln Leu Glu Val
            35                  40                  45

Asn Gly Ser Gln His Ser Leu Thr Cys Ala Phe Glu Asp Pro Asp Val
50                  55                  60

Asn Thr Thr Asn Leu Glu Phe Glu Ile Cys Gly Ala Leu Val Glu Val
```

```
                65                  70                  75                  80
Lys Cys Leu Asn Phe Arg Lys Leu Gln Glu Ile Tyr Phe Ile Glu Thr
                    85                  90                  95

Lys Lys Phe Leu Leu Ile Gly Lys Ser Asn Ile Cys Val Lys Val Gly
                100                 105                 110

Glu Lys Ser Leu Thr Cys Lys Lys Ile Asp Leu Thr Thr Ile Val Lys
                115                 120                 125

Pro Glu Ala Pro Phe Asp Leu Ser Val Ile Tyr Arg Glu Gly Ala Asn
                130                 135                 140

Asp Phe Val Val Thr Phe Asn Thr Ser His Leu Gln Lys Lys Tyr Val
145                 150                 155                 160

Lys Val Leu Met His Asp Val Ala Tyr Arg Gln Glu Lys Asp Glu Asn
                165                 170                 175

Lys Trp Thr His Val Asn Leu Ser Thr Lys Leu Thr Leu Leu Gln
                180                 185                 190

Arg Lys Leu Gln Pro Ala Ala Met Tyr Glu Ile Lys Val Arg Ser Ile
                195                 200                 205

Pro Asp His Tyr Phe Lys Gly Phe Trp Ser Glu Trp Ser Pro Ser Tyr
                210                 215                 220

Tyr Phe Arg Thr Pro Glu Ile Asn Asn Ser Ser Gly Leu Ser Leu Ser
225                 230                 235                 240

Tyr Gly Pro Val Ser Pro Ile Ile Arg Arg Leu Trp Asn Ile Phe Val
                245                 250                 255

Arg Asn Gln Glu Lys
                260

<210> SEQ ID NO 11
<211> LENGTH: 252
<212> TYPE: PRT
<213> ORGANISM: Homo sapiens

<400> SEQUENCE: 11

Met Thr Ile Leu Gly Thr Thr Phe Gly Met Val Phe Ser Leu Leu Gln
1               5                   10                  15

Val Val Ser Gly Glu Ser Gly Tyr Ala Gln Asn Gly Asp Leu Glu Asp
                20                  25                  30

Ala Glu Leu Asp Asp Tyr Ser Phe Ser Cys Tyr Ser Gln Leu Glu Val
                35                  40                  45

Asn Gly Ser Gln His Ser Leu Thr Cys Ala Phe Glu Asp Pro Asp Val
            50                  55                  60

Asn Thr Thr Asn Leu Glu Phe Glu Ile Cys Gly Ala Leu Val Glu Val
65                  70                  75                  80

Lys Cys Leu Asn Phe Arg Lys Leu Gln Glu Ile Tyr Phe Ile Glu Thr
                    85                  90                  95

Lys Lys Phe Leu Leu Ile Gly Lys Ser Asn Ile Cys Val Lys Val Gly
                100                 105                 110

Glu Lys Ser Leu Thr Cys Lys Lys Ile Asp Leu Thr Thr Ile Val Lys
                115                 120                 125

Pro Glu Ala Pro Phe Asp Leu Ser Val Ile Tyr Arg Glu Gly Ala Asn
                130                 135                 140

Asp Phe Val Val Thr Phe Asn Thr Ser His Leu Gln Lys Lys Tyr Val
145                 150                 155                 160

Lys Val Leu Met His Asp Val Ala Tyr Arg Gln Glu Lys Asp Glu Asn
                165                 170                 175
```

Lys Trp Thr His Val Asn Leu Ser Ser Thr Lys Leu Thr Leu Leu Gln
            180                 185                 190

Arg Lys Leu Gln Pro Ala Ala Met Tyr Glu Ile Lys Val Arg Ser Ile
        195                 200                 205

Pro Asp His Tyr Phe Lys Gly Phe Trp Ser Glu Trp Ser Pro Ser Tyr
    210                 215                 220

Tyr Phe Arg Thr Pro Glu Ile Asn Asn Ser Ser Gly Leu Ser Leu Ser
225                 230                 235                 240

Tyr Gly Pro Val Ser Pro Ile Ile Arg Gln Glu Leu
                245                 250

<210> SEQ ID NO 12
<211> LENGTH: 4617
<212> TYPE: DNA
<213> ORGANISM: Homo sapiens

<400> SEQUENCE: 12

| | | | | | |
|---|---|---|---|---|---|
| atctaagctt | ctctgtcttc | ctccctccct | ccttcctct | tactctcatt | catttcatac | 60 |
| acactggctc | acacatctac | tctctctctc | tatctctctc | agaatgacaa | ttctaggtac | 120 |
| aactttggc | atggttttt | ctttacttca | agtcgtttct | ggagaaagtg | gctatgctca | 180 |
| aaatggagac | ttggaagatg | cagaactgga | tgactactca | ttctcatgct | atagccagtt | 240 |
| ggaagtgaat | ggatcgcagc | actcactgac | ctgtgctttt | gaggacccag | atgtcaacat | 300 |
| caccaatctg | gaatttgaaa | tatgtgggc | cctcgtggag | gtaaagtgcc | tgaatttcag | 360 |
| gaaactacaa | gagatatatt | tcatcgagac | aaagaaattc | ttactgattg | aaagagcaa | 420 |
| tatatgtgtg | aaggttggag | aaaagagtct | aacctgcaaa | aaatagacc | taaccactat | 480 |
| agttaaacct | gaggctcctt | ttgacctgag | tgtcgtctat | cgggaaggag | ccaatgactt | 540 |
| tgtggtgaca | tttaatacat | cacacttgca | aaagaagtat | gtaaaagttt | taatgcacga | 600 |
| tgtagcttac | cgccaggaaa | aggatgaaaa | caaatggacg | catgtgaatt | tatccagcac | 660 |
| aaagctgaca | ctcctgcaga | gaaagctcca | accggcagca | atgtatgaga | ttaaagttcg | 720 |
| atccatccct | gatcactatt | ttaaaggctt | ctggagtgaa | tggagtccaa | gttattactt | 780 |
| cagaactcca | gagatcaata | atagctcagg | ggagatggat | cctatcttac | taaccatcag | 840 |
| cattttgagt | ttttctctg | tcgctctgtt | ggtcatcttg | gcctgtgtgt | tatggaaaaa | 900 |
| aaggattaag | cctatcgtat | ggcccagtct | ccccgatcat | aagaagactc | tggaacatct | 960 |
| ttgtaagaaa | ccaagaaaaa | atttaaatgt | gagtttcaat | cctgaaagtt | tcctggactg | 1020 |
| ccagattcat | agggtggatg | acattcaagc | tagagatgaa | gtggaaggtt | ttctgcaaga | 1080 |
| tacgtttcct | cagcaactag | aagaatctga | gaagcagagg | cttggagggg | atgtgcagag | 1140 |
| ccccaactgc | ccatctgagg | atgtagtcat | cactccagaa | agctttggaa | gagattcatc | 1200 |
| cctcacatgc | ctggctggga | atgtcagtgc | atgtgacgcc | ctattctct | cctcttccag | 1260 |
| gtccctagac | tgcagggaga | gtggcaagaa | tgggcctcat | gtgtaccagg | acctcctgct | 1320 |
| tagccttggg | actacaaaca | gcacgctgcc | ccctccatt | tctctccaat | ctggaatcct | 1380 |
| gacattgaac | ccagttgctc | agggtcagcc | cattcttact | ccctgggat | caaatcaaga | 1440 |
| agaagcatat | gtcaccatgt | ccagcttcta | ccaaaaccag | tgaagtgtaa | gaaacccaga | 1500 |
| ctgaacttac | cgtgagcgac | aaagatgatt | taaagggaa | gtctagagtt | cctagtctcc | 1560 |
| ctcacagcac | agagaagaca | aaattagcaa | accccacta | cacagtctgc | aagattctga | 1620 |
| aacattgctt | tgaccactct | tcctgagttc | agtggcactc | aacatgagtc | aagagcatcc | 1680 |

```
tgcttctacc atgtggattt ggtcacaagg tttaaggtga cccaatgatt cagctattta    1740
aaaaaaaaag aggaaagaat gaaagagtaa aggaaatgat tgaggagtga ggaaggcagg    1800
aagagagcat gagaggaaag aaagaaagga aaataaaaaa tgatagttgc cattattagg    1860
atttaatata tatccagtgc tttgcaagtg ctctgcgcac cttgtctcac tccatcctga    1920
caataatcct gggaggtgtg tgcaattact acgactactc tcttttttat agatcattaa    1980
attcagaact aaggagttaa gtaacttgtc caagttgttc acacagtgaa ggagggggcc    2040
aagatatgat ggctgggagt ctaattgcag ttccctgagc catgtgcctt tctcttcact    2100
gaggactgcc ccattcttga gtgccaaacg tcactagtaa cagggtgtgc ctagataatt    2160
tatgatccaa actgagtcag tttggaaagt gaaagggaaa cttacatata tccctccgg    2220 gacaatgagc aaaactagg actgtcccca gacaaatgtg aacatacata tcatcactta    2280
aattaaaatg gctatgagaa agaaagaggg ggagaaacag tcttgcgggt gtgaagtccc    2340
atgaccagcc atgtcaaaag aaggtaaaga agtcaagaaa aagccatgaa gcccatttgg    2400
tttcattttt ctgaaaatag gctcaagagg gaataaaatta gaaactcaca atttctcttg    2460
tttgttacca agacagtgat tctcttgctg ctaccaccca actgcatccg tccatgatct    2520
cagaggaaac tgtcgctgac cctggacatg ggtacgtttg acgagtgaga ggaggcatga    2580
cccctcccat gtgtatagac actaccccaa cctaaattca tccctaaatt gtcccaagtt    2640
ctccagcaat agaggctgcc acaaacttca gggagaaaga gttacaagta catgcaatga    2700
gtgaactgac tgtggctaca atcttgaaga tatacggaag agacgtatta ttaatgcttg    2760
acatatatca tcttgccttt cttggtctag actgacttct aatgactaac tcaaagtcaa    2820
ggcaactgag taatgtcagc tcagcaaagt gcagcaaacc catctcccac aggcctccaa    2880
accctggctg ttcacagaac cacaaagggc agatgctgca cagaaaacta gagaaggggt    2940
cataggttca tggttttgtt tgagatttgt tgctactgtt tttctgtttt gaattttctt    3000 cttttgttctg ttttttacttt atttaggggg actaggtgtt tctgatattt tagttttctt    3060
gtttgttttg ttttgtgttg tctgtgaatg gggttttaac tgtggatgaa tggaccttat    3120
ctgttggctt aaaggactgg taagatcaga ccatcttatt cttcaggtga atgttttact    3180
ttccaaagtg ctctcctctg caccagcagt aataaataca atgccataat cccttaggtt    3240
tgcctagtgc ttttgcaatt ttcaaagcac ttccataagc attccttcca cctccttgat    3300
aggcatttat ggaaagcctg ctacatgtca atcatactgt taggcacagg ggacctaaag    3360
acacataaaa ggatggcatt ctgcctcata aattgcaaaa cctaatgaaa gtgactgctt    3420
ggtaaacaaa ttattattat attataaaat gctataaaag agccatattg aaagtgccct    3480
gttggagaca gggcaaatgc cacaaaaatg atgtaaattt acatggagga aaagtagaat    3540
ctgcctggtt tgtaggcagc agaagacatt tttcatcagt gggcaggtgt tctttacctt    3600
ttgtagaaat gggagtcaag tctcaaatag gaggctccac aaaatctcat gccaggtctc    3660 tgataccta ttcacagaag ttctttgaag tatttattgt tattttcttt gacttatggg    3720
aaaactggga cacaggaaga caggtaaatt acccaacctc acacgttaag tcagaactgg    3780
gagccataat tttgtatccc tggtataaat agacaatctc ttgaagaaat gaagagatga    3840
ccatagaaaa acatcgagat atctccagct ctaaaatcct ttgtttcaat gttgtttggc    3900
atatgttatc tttggaattt agtgtctgag cctctgtctg ttactgtagt atttaaaatg    3960
catgtattat aatcatataa tcataactgc tgttaattct tgattatata cctagggaca    4020
atgtgtaatg taagattact aattggttct gcccaatctc ctttcagatt ttattaggaa    4080
```

-continued

```
aaaaaaataa acctcctgat cggagacaat gtattaatca gaagtgtaaa ctgccagttc    4140
tatatagcat gaaatgaaaa gacagctaat ttggtccaac aaacatgact gggtctaggg    4200
cacccaggct gattcagctg atttcctacc agcctttgcc tcttccttca atgtggtttc    4260
catgggaatt tgcttcagaa aagccaagta tgggctgttc agaggtgcac acctgcattt    4320
tcttagctct tctagagggg ctaagagact tggtacgggc aggaagaat atgtggcaga     4380 gctcctggaa atgatgcaga ttaggtggca tttttgtcag ctctgtggtt tattgttggg    4440
actattcttt aaaatatcca ttgttcacta cagtgaagat ctctgattta accgtgtact    4500
atccacatgc attacaaaca tttcgcagag ctgcttagta tataagcgta caatgtatgt    4560
aataaccatc tcatatttaa ttaaatggta tagaagaaca aaaaaaaaaa aaaaaaa      4617
```

<210> SEQ ID NO 13
<211> LENGTH: 369
<212> TYPE: PRT
<213> ORGANISM: Homo sapiens

<400> SEQUENCE: 13

```
Met Leu Lys Pro Ser Leu Pro Phe Thr Ser Leu Leu Phe Leu Gln Leu
1               5                   10                  15

Pro Leu Leu Gly Val Gly Leu Asn Thr Thr Ile Leu Thr Pro Asn Gly
            20                  25                  30

Asn Glu Asp Thr Thr Ala Asp Phe Leu Thr Thr Met Pro Thr Asp
        35                  40                  45

Ser Leu Ser Val Ser Thr Leu Pro Leu Pro Glu Val Gln Cys Phe Val
    50                  55                  60

Phe Asn Val Glu Tyr Met Asn Cys Thr Trp Asn Ser Ser Ser Glu Pro
65                  70                  75                  80

Gln Pro Thr Asn Leu Thr Leu His Tyr Trp Tyr Lys Asn Ser Asp Asn
                85                  90                  95

Asp Lys Val Gln Lys Cys Ser His Tyr Leu Phe Ser Glu Glu Ile Thr
            100                 105                 110

Ser Gly Cys Gln Leu Gln Lys Lys Glu Ile His Leu Tyr Gln Thr Phe
        115                 120                 125

Val Val Gln Leu Gln Asp Pro Arg Glu Pro Arg Arg Gln Ala Thr Gln
    130                 135                 140

Met Leu Lys Leu Gln Asn Leu Val Ile Pro Trp Ala Pro Glu Asn Leu
145                 150                 155                 160

Thr Leu His Lys Leu Ser Glu Ser Gln Leu Glu Leu Asn Trp Asn Asn
                165                 170                 175

Arg Phe Leu Asn His Cys Leu Glu His Leu Val Gln Tyr Arg Thr Asp
            180                 185                 190

Trp Asp His Ser Trp Thr Glu Gln Ser Val Asp Tyr Arg His Lys Phe
        195                 200                 205

Ser Leu Pro Ser Val Asp Gly Gln Lys Arg Tyr Thr Phe Arg Val Arg
    210                 215                 220

Ser Arg Phe Asn Pro Leu Cys Gly Ser Ala Gln His Trp Ser Glu Trp
225                 230                 235                 240

Ser His Pro Ile His Trp Gly Ser Asn Thr Ser Lys Glu Asn Pro Phe
                245                 250                 255

Leu Phe Ala Leu Glu Ala Val Val Ile Ser Val Gly Ser Met Gly Leu
            260                 265                 270

Ile Ile Ser Leu Leu Cys Val Tyr Phe Trp Leu Glu Arg Thr Met Pro
```

```
                     275                 280                 285
Arg Ile Pro Thr Leu Lys Asn Leu Glu Asp Leu Val Thr Glu Tyr His
    290                 295                 300

Gly Asn Phe Ser Ala Trp Ser Gly Val Ser Lys Gly Leu Ala Glu Ser
305                 310                 315                 320

Leu Gln Pro Asp Tyr Ser Glu Arg Leu Cys Leu Val Ser Glu Ile Pro
                325                 330                 335

Pro Lys Gly Ala Leu Gly Glu Gly Pro Gly Ala Ser Pro Cys Asn
            340                 345                 350

Gln His Ser Pro Tyr Trp Ala Pro Pro Cys Tyr Thr Leu Lys Pro Glu
            355                 360                 365

Thr

<210> SEQ ID NO 14
<211> LENGTH: 179
<212> TYPE: PRT
<213> ORGANISM: Homo sapiens

<400> SEQUENCE: 14

Met Gly Met Lys Thr Pro Gln Leu Glu Gln Ser Val Asp Tyr Arg His
1               5                   10                  15

Lys Phe Ser Leu Pro Ser Val Asp Gly Gln Lys Arg Tyr Thr Phe Arg
                20                  25                  30

Val Arg Ser Arg Phe Asn Pro Leu Cys Gly Ser Ala Gln His Trp Ser
            35                  40                  45

Glu Trp Ser His Pro Ile His Trp Gly Ser Asn Thr Ser Lys Glu Asn
    50                  55                  60

Pro Phe Leu Phe Ala Leu Glu Ala Val Val Ile Ser Val Gly Ser Met
65                  70                  75                  80

Gly Leu Ile Ile Ser Leu Leu Cys Val Tyr Phe Trp Leu Glu Arg Thr
                85                  90                  95

Met Pro Arg Ile Pro Thr Leu Lys Asn Leu Glu Asp Leu Val Thr Glu
                100                 105                 110

Tyr His Gly Asn Phe Ser Ala Trp Ser Gly Val Ser Lys Gly Leu Ala
            115                 120                 125

Glu Ser Leu Gln Pro Asp Tyr Ser Glu Arg Leu Cys Leu Val Ser Glu
    130                 135                 140

Ile Pro Pro Lys Gly Ala Leu Gly Glu Gly Pro Gly Ala Ser Pro
145                 150                 155                 160

Cys Asn Gln His Ser Pro Tyr Trp Ala Pro Pro Cys Tyr Thr Leu Lys
                165                 170                 175

Pro Glu Thr

<210> SEQ ID NO 15
<211> LENGTH: 1560
<212> TYPE: DNA
<213> ORGANISM: Homo sapiens

<400> SEQUENCE: 15
agaggaaacg tgtgggtggg gagggtagt  gggtgaggga cccaggttcc tgacacagac    60
agactacacc cagggaatga agagcaagcg ccatgttgaa gccatcatta ccattcacat   120
ccctcttatt cctgcagctg cccctgctgg gagtggggct gaacacgaca attctgacgc   180
ccaatgggaa tgaagacacc acagctgatt cttcctgac cactatgccc actgactccc   240
tcagtgtttc cactctgccc ctcccagagg ttcagtgttt tgtgttcaat gtcgagtaca   300
```

```
tgaattgcac ttggaacagc agctctgagc cccagcctac caacctcact ctgcattatt    360
ggtacaagaa ctcggataat gataaagtcc agaagtgcag ccactatcta ttctctgaag    420
aaatcacttc tggctgtcag ttgcaaaaaa aggagatcca cctctaccaa acatttgttg    480
ttcagctcca ggaccacgg gaacccagga acaggccac acagatgcta aaactgcaga     540
atctggtgat ccctgggct ccagagaacc taacacttca caaactgagt gaatcccagc    600
tagaactgaa ctgaacaac agattcttga accactgttt ggagcacttg gtgcagtacc    660
ggactgactg ggaccacagc tggactgaac aatcagtgga ttatagacat aagttctcct    720
tgcctagtgt ggatgggcag aaacgctaca cgtttcgtgt tcggagccgc tttaacccac    780
tctgtggaag tgctcagcat tggagtgaat ggagccaccc aatccactgg gggagcaata    840
cttcaaaaga gaatcctttc ctgtttgcat tggaagccgt ggttatctct gttggctcca    900
tgggattgat tatcagcctt ctctgtgtgt atttctggct ggaacggacg atgccccgaa    960
ttcccaccct gaagaaccta gaggatcttg ttactgaata ccacgggaac ttttcggcct   1020
ggagtggtgt gtctaaggga ctggctgaga gtctgcagcc agactacagt gaacgactct   1080
gcctcgtcag tgagattccc ccaaaaggag gggcccttgg ggaggggcct ggggcctccc   1140
catgcaacca gcatagcccc tactgggccc cccatgttta caccctaaag cctgaaacct   1200
gaaccccaat cctctgacag aagaacccca gggtcctgta gccctaagtg gtactaactt   1260
tccttcattc aacccacctg cgtctcatac tcacctcacc ccactgtggc tgatttggaa   1320
ttttgtgccc ccatgtaagc accccttcat ttggcattcc ccacttgaga attacccttt   1380
tgccccgaac atgttttttct tctccctcag tctggcccttc cttttcgca ggattcttcc   1440
tccctccctc tttccctccc ttcctctttc catctaccct ccgattgttc ctgaaccgat   1500
gagaaataaa gtttctgttg ataatcatca aaaaaaaaaa aaaaaaaaa aaaaaaaaa    1560

<210> SEQ ID NO 16
<211> LENGTH: 162
<212> TYPE: PRT
<213> ORGANISM: Homo sapiens

<400> SEQUENCE: 16

Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
                20                  25                  30

Val Phe Ile Leu Gly Cys Phe Ser Ala Gly Leu Pro Lys Thr Glu Ala
            35                  40                  45

Asn Trp Val Asn Val Ile Ser Asp Leu Lys Lys Ile Glu Asp Leu Ile
        50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
        115                 120                 125

Thr Glu Ser Gly Cys Lys Glu Cys Glu Glu Leu Glu Glu Lys Asn Ile
    130                 135                 140

Lys Glu Phe Leu Gln Ser Phe Val His Ile Val Gln Met Phe Ile Asn
```

```
145                 150                 155                 160

Thr Ser

<210> SEQ ID NO 17
<211> LENGTH: 135
<212> TYPE: PRT
<213> ORGANISM: Homo sapiens

<400> SEQUENCE: 17

Met Val Leu Gly Thr Ile Asp Leu Cys Ser Cys Phe Ser Ala Gly Leu
1               5                   10                  15

Pro Lys Thr Glu Ala Asn Trp Val Asn Val Ile Ser Asp Leu Lys Lys
            20                  25                  30

Ile Glu Asp Leu Ile Gln Ser Met His Ile Asp Ala Thr Leu Tyr Thr
        35                  40                  45

Glu Ser Asp Val His Pro Ser Cys Lys Val Thr Ala Met Lys Cys Phe
    50                  55                  60

Leu Leu Glu Leu Gln Val Ile Ser Leu Glu Ser Gly Asp Ala Ser Ile
65                  70                  75                  80

His Asp Thr Val Glu Asn Leu Ile Ile Leu Ala Asn Asn Ser Leu Ser
                85                  90                  95

Ser Asn Gly Asn Val Thr Glu Ser Gly Cys Lys Glu Cys Glu Glu Leu
            100                 105                 110

Glu Glu Lys Asn Ile Lys Glu Phe Leu Gln Ser Phe Val His Ile Val
        115                 120                 125

Gln Met Phe Ile Asn Thr Ser
    130                 135

<210> SEQ ID NO 18
<211> LENGTH: 2012
<212> TYPE: DNA
<213> ORGANISM: Homo sapiens

<400> SEQUENCE: 18
gttgggactc cgggtggcag gcgcccgggg gaatcccagc tgactcgctc actgccttcg      60
aagtccggcg ccccccggga gggaactggg tggccgcacc ctcccggctg cggtggctgt     120
cgccccccac cctgcagcca ggactcgatg gagaatccat tccaatatat ggccatgtgg     180
ctctttggag caatgttcca tcatgttcca tgctgctgac gtcacatgga gcacagaaat     240
caatgttagc agatagccag cccatacaag atcgtattgt attgtaggag cattgtgga     300
tggatggctg ctggaaaccc cttgccatag ccagctcttc ttcaatactt aaggatttac     360
cgtggctttg agtaatgaga atttcgaaac cacatttgag aagtatttcc atccagtgct     420
acttgtgttt acttctaaac agtcattttc taactgaagc tggcattcat gtcttcattt     480
tgggctgttt cagtgcaggg cttcctaaaa cagaagccaa ctgggtgaat gtaataagtg     540
atttgaaaaa aattgaagat cttattcaat ctatgcatat tgatgctact ttatatacgg     600
aaagtgatgt tcaccccagt tgcaaagtaa cagcaatgaa gtgctttctc ttggagttac     660
aagttatttc acttgagtcc ggagatgcaa gtattcatga tacagtagaa aatctgatca     720
tcctagcaaa caacagtttg tcttctaatg ggaatgtaac agaatctgga tgcaaagaat     780
gtgaggaact ggaggaaaaa aatattaaag aattttttgca gagttttgta catattgtcc     840
aaatgttcat caacacttct tgattgcaat tgattctttt taaagtgttt ctgttattaa     900
caaacatcac tctgctgctt agacataaca aaacactcgg catttcaaat gtgctgtcaa     960
```

| | |
|---|---|
| aacaagtttt tctgtcaaga agatgatcag accttggatc agatgaactc ttagaaatga | 1020 |
| aggcagaaaa atgtcattga gtaatatagt gactatgaac ttctctcaga cttactttac | 1080 |
| tcattttttt aatttattat tgaaattgta catatttgtg gaataatgta aaatgttgaa | 1140 |
| taaaaatatg tacaagtgtt gttttttaag ttgcactgat attttacctc ttattgcaaa | 1200 |
| atagcatttg tttaagggtg atagtcaaat tatgtattgg tgggctggg taccaatgct | 1260 |
| gcaggtcaac agctatgctg gtaggctcct gccagtgtgg aaccactgac tactggctct | 1320 |
| cattgacttc cttactaagc atagcaaaca gaggaagaat tgttatcag taagaaaaag | 1380 |
| aagaactata tgtgaatcct cttctttata ctgtaattta gttattgatg tataaagcaa | 1440 |
| ctgttatgaa ataaagaaat tgcaataact ggcatataat gtccatcagt aaatcttggt | 1500 |
| ggtggtggca ataataaact tctactgata ggtagaatgg tgtgcaagct tgtccaatca | 1560 |
| cggattgcag gccacatgcg gcccaggaca actttgaatg tgcccaaca caaattcata | 1620 |
| aactttcata catctcgttt ttagctcatc agctatcatt agcggtagtg tatttaaagt | 1680 |
| gtggcccaag acaattcttc ttattccaat gtggcccagg gaaatcaaaa gattggatgc | 1740 |
| ccctggtata gaaaactaat agtgacagtg ttcatatttc atgctttccc aaatacaggt | 1800 |
| atttattttt cacattcttt ttgccatgtt tatataataa taaagaaaaa ccctgttgat | 1860 |
| ttgttggagc cattgttatc tgacagaaaa taattgttta tattttttgc actacactgt | 1920 |
| ctaaaattag caagctctct tctaatgaaa ctgtaagaaa gatgaaatat ttttgtttta | 1980 |
| ttataaattt atttcacctt aaaaaaaaaa aa | 2012 |

<210> SEQ ID NO 19
<211> LENGTH: 2333
<212> TYPE: DNA
<213> ORGANISM: Homo sapiens

<400> SEQUENCE: 19

| | |
|---|---|
| gttgggactc cgggtggcag gcgcccgggg gaatcccagc tgactcgctc actgccttcg | 60 |
| aagtccggcg ccccccggga gggaactggg tggccgcacc ctcccggctg cggtggctgt | 120 |
| cgccccccac cctgcagcca ggactcgatg gagaatccat tccaatatat ggccatgtgg | 180 |
| ctctttggag caatgttcca tcatgttcca tgctgctgac gtcacatgga gcacagaaat | 240 |
| caatgttagc agatagccag cccatacaag atcgttttca actagtggcc ccactgtgtc | 300 |
| cggaattgat gggttcttgg tctcactgac ttcaagaatg aagccgcgga ccctcgcggt | 360 |
| gagtgttaca gctcttaagg tggcgcatct ggagtttgtt ccttctgatg ttcgatgtg | 420 |
| ttcggagttt cttccttctg gtgggttcgt ggtctcgctg gctcaggagt gaagctacag | 480 |
| accttcgcgg aggcattgtg gatggatggc tgctggaaac cccttgccat agccagctct | 540 |
| tcttcaatac ttaaggattt accgtggctt tgagtaatga aatttcgaa accacatttg | 600 |
| agaagtattt ccatccagtg ctacttgtgt ttacttctaa acagtcattt tctaactgaa | 660 |
| gctggcattc atgtcttcat tttgggatgc agctaatata cccagttggc ccaaagcacc | 720 |
| taacctatag ttatataatc tgactctcag ttcagttta ctctactaat gccttcatgg | 780 |
| tattgggaac catagatttg tgcagctgtt tcagtgcagg gcttcctaaa acagaagcca | 840 |
| actgggtgaa tgtaataagt gatttgaaaa aaattgaaga tcttattcaa tctatgcata | 900 |
| ttgatgctac tttatatacg gaaagtgatg ttcaccccag ttgcaaagta acagcaatga | 960 |
| agtgctttct cttggagtta caagttattt cacttgagtc cggagatgca agtattcatg | 1020 |
| atacagtaga aaatctgatc atcctagcaa acaacagttt gtcttctaat gggaatgtaa | 1080 |

```
cagaatctgg atgcaaagaa tgtgaggaac tggaggaaaa aaatattaaa gaattttttgc    1140 agagttttgt acatattgtc caaatgttca tcaacacttc ttgattgcaa ttgattcttt    1200
ttaaagtgtt tctgttatta acaaacatca ctctgctgct tagacataac aaaacactcg    1260
gcatttcaaa tgtgctgtca aaacaagttt ttctgtcaag aagatgatca gaccttggat    1320
cagatgaact cttagaaatg aaggcagaaa aatgtcattg agtaatatag tgactatgaa    1380
cttctctcag acttacttta ctcattttt taatttatta ttgaaattgt acatatttgt    1440
ggaataatgt aaaatgttga ataaaaatat gtacaagtgt tgtttttaa gttgcactga    1500 tattttacct cttattgcaa aatagcattt gtttaagggt gatagtcaaa ttatgtattg    1560
gtggggctgg gtaccaatgc tgcaggtcaa cagctatgct ggtaggctcc tgccagtgtg    1620
gaaccactga ctactggctc tcattgactt ccttactaag catagcaaac agaggaagaa    1680
tttgttatca gtaagaaaaa gaagaactat atgtgaatcc tcttctttat actgtaattt    1740
agttattgat gtataaagca actgttatga aataaagaaa ttgcaataac tggcatataa    1800
tgtccatcag taaatcttgg tggtggtggc aataataaac ttctactgat aggtagaatg    1860
gtgtgcaagc ttgtccaatc acggattgca ggccacatgc ggcccaggac aactttgaat    1920
gtggcccaac acaaattcat aaactttcat acatctcgtt tttagctcat cagctatcat    1980
tagcggtagt gtatttaaag tgtggcccaa gacaattctt cttattccaa tgtgcccag    2040 ggaaatcaaa agattggatg cccctggtat agaaaactaa tagtgacagt gttcatattt    2100
catgctttcc caaatacagg tatttttt tcacattctt tttgccatgt ttatataata    2160
ataaagaaaa accctgttga tttgttggag ccattgttat ctgacagaaa ataattgttt    2220 atatttttg cactacactg tctaaaatta gcaagctctc ttctaatgga actgtaagaa    2280
agatgaaata tttttgtttt attataaatt tatttcacct taaaaaaaaa aaa            2333
```

<210> SEQ ID NO 20
<211> LENGTH: 551
<212> TYPE: PRT
<213> ORGANISM: Homo sapiens

<400> SEQUENCE: 20

```
Met Ala Ala Pro Ala Leu Ser Trp Arg Leu Pro Leu Ile Leu Leu
1               5                   10                  15

Leu Pro Leu Ala Thr Ser Trp Ala Ser Ala Ala Val Asn Gly Thr Ser
                20                  25                  30

Gln Phe Thr Cys Phe Tyr Asn Ser Arg Ala Asn Ile Ser Cys Val Trp
            35                  40                  45

Ser Gln Asp Gly Ala Leu Gln Asp Thr Ser Cys Gln Val His Ala Trp
        50                  55                  60

Pro Asp Arg Arg Arg Trp Asn Gln Thr Cys Glu Leu Leu Pro Val Ser
65                  70                  75                  80

Gln Ala Ser Trp Ala Cys Asn Leu Ile Leu Gly Ala Pro Asp Ser Gln
                85                  90                  95

Lys Leu Thr Thr Val Asp Ile Val Thr Leu Arg Val Leu Cys Arg Glu
            100                 105                 110

Gly Val Arg Trp Arg Val Met Ala Ile Gln Asp Phe Lys Pro Phe Glu
        115                 120                 125

Asn Leu Arg Leu Met Ala Pro Ile Ser Leu Gln Val Val His Val Glu
    130                 135                 140

Thr His Arg Cys Asn Ile Ser Trp Glu Ile Ser Gln Ala Ser His Tyr
```

```
            145                 150                 155                 160
       Phe Glu Arg His Leu Glu Phe Glu Ala Arg Thr Leu Ser Pro Gly His
                       165                 170                 175
       Thr Trp Glu Glu Ala Pro Leu Leu Thr Leu Lys Gln Lys Gln Glu Trp
                       180                 185                 190
       Ile Cys Leu Glu Thr Leu Thr Pro Asp Thr Gln Tyr Glu Phe Gln Val
                       195                 200                 205
       Arg Val Lys Pro Leu Gln Gly Glu Phe Thr Thr Trp Ser Pro Trp Ser
                       210                 215                 220
       Gln Pro Leu Ala Phe Arg Thr Lys Pro Ala Ala Leu Gly Lys Asp Thr
       225                 230                 235                 240
       Ile Pro Trp Leu Gly His Leu Leu Val Gly Leu Ser Gly Ala Phe Gly
                       245                 250                 255
       Phe Ile Ile Leu Val Tyr Leu Leu Ile Asn Cys Arg Asn Thr Gly Pro
                       260                 265                 270
       Trp Leu Lys Lys Val Leu Lys Cys Asn Thr Pro Asp Pro Ser Lys Phe
                       275                 280                 285
       Phe Ser Gln Leu Ser Ser Glu His Gly Gly Asp Val Gln Lys Trp Leu
                       290                 295                 300
       Ser Ser Pro Phe Pro Ser Ser Ser Phe Ser Pro Gly Gly Leu Ala Pro
       305                 310                 315                 320
       Glu Ile Ser Pro Leu Glu Val Leu Glu Arg Asp Lys Val Thr Gln Leu
                       325                 330                 335
       Leu Leu Gln Gln Asp Lys Val Pro Glu Pro Ala Ser Leu Ser Ser Asn
                       340                 345                 350
       His Ser Leu Thr Ser Cys Phe Thr Asn Gln Gly Tyr Phe Phe Phe His
                       355                 360                 365
       Leu Pro Asp Ala Leu Glu Ile Glu Ala Cys Gln Val Tyr Phe Thr Tyr
                       370                 375                 380
       Asp Pro Tyr Ser Glu Glu Asp Pro Asp Glu Gly Val Ala Gly Ala Pro
       385                 390                 395                 400
       Thr Gly Ser Ser Pro Gln Pro Leu Gln Pro Leu Ser Gly Glu Asp Asp
                       405                 410                 415
       Ala Tyr Cys Thr Phe Pro Ser Arg Asp Asp Leu Leu Leu Phe Ser Pro
                       420                 425                 430
       Ser Leu Leu Gly Gly Pro Ser Pro Pro Ser Thr Ala Pro Gly Gly Ser
                       435                 440                 445
       Gly Ala Gly Glu Glu Arg Met Pro Pro Ser Leu Gln Glu Arg Val Pro
                       450                 455                 460
       Arg Asp Trp Asp Pro Gln Pro Leu Gly Pro Pro Thr Pro Gly Val Pro
       465                 470                 475                 480
       Asp Leu Val Asp Phe Gln Pro Pro Pro Glu Leu Val Leu Arg Glu Ala
                       485                 490                 495
       Gly Glu Glu Val Pro Asp Ala Gly Pro Arg Glu Gly Val Ser Phe Pro
                       500                 505                 510
       Trp Ser Arg Pro Pro Gly Gln Gly Glu Phe Arg Ala Leu Asn Ala Arg
                       515                 520                 525
       Leu Pro Leu Asn Thr Asp Ala Tyr Leu Ser Leu Gln Glu Leu Gln Gly
                       530                 535                 540
       Gln Asp Pro Thr His Leu Val
       545                 550

<210> SEQ ID NO 21
```

```
<211> LENGTH: 4050
<212> TYPE: DNA
<213> ORGANISM: Homo sapiens

<400> SEQUENCE: 21
gcagccagag ctcagcaggg ccctggagag atggccacgg tcccagcacc ggggaggact    60
ggagagcgcg cgctgccacc gccccatgtc tcagccaggg cttccttcct cggctccacc   120
ctgtggatgt aatggcggcc cctgctctgt cctggcgtct gccctcctc atcctcctcc    180 tgcccctggc tacctcttgg gcatctgcag cggtgaatgg cacttcccag ttcacatgct   240
tctacaactc gagagccaac atctcctgtg tctggagcca agatgggct ctgcaggaca    300 cttcctgcca agtccatgcc tggccggaca gacggcggtg gaaccaaacc tgtgagctgc   360
tccccgtgag tcaagcatcc tgggcctgca acctgatcct cggagcccca gattctcaga   420
aactgaccac agttgacatc gtcaccctga gggtgctgtg ccgtgagggg gtgcgatgga   480
gggtgatggc catccaggac ttcaagccct tgagaacct cgcctgatg ccccccatct     540 ccctccaagt tgtccacgtg agacccaca gatgcaacat aagctgggaa atctcccaag    600
cctcccacta ctttgaaaga cacctggagt tcgaggcccg acgctgtcc ccaggccaca    660 cctgggagga ggcccccctg ctgactctca agcagaagag gaatggatc tgcctggaga    720 cgctcacccc agacacccag tatgagtttc aggtgcgggt caagcctctg caaggcgagt   780
tcacgacctg gagccctgg agccagcccc tggccttcag acaaagcct gcagcccttg     840 ggaaggacac cattccgtgg ctcggccacc tcctcgtggg cctcagcggg gcttttggct   900
tcatcatctt agtgtacttg ctgatcaact gcaggaacac cgggccatgg ctgaagaagg   960
tcctgaagtg taacaccccca gacccctcga agttctttt ccagctgagc tcagagcatg    1020
gaggagacgt ccagaagtgg ctctcttcgc ccttcccctc atcgtccttc agccctggcg   1080
gcctggcacc tgagatctcg ccactagaag tgctggagag gacaaggtg acgcagctgc    1140 tcctgcagca ggacaaggtg cctgagcccg catccttaag cagcaaccac tgctgacca    1200 gctgcttcac caaccagggt tacttcttct tccacctccc ggatgccttg gagatagagg   1260
cctgccaggt gtactttact tacgaccct actcagagga agaccctgat gagggtgtgg    1320
ccggggcacc cacagggtct tccccccaac ccctgcagcc tctgtcaggg gaggacgacg   1380
cctactgcac cttcccctcc agggatgacc tgctgctctt ctccccccagt ctcctcggtg   1440 gccccagccc ccaagcact gccctgggg gcagtgggc cggtgaagag aggatgcccc      1500
cttctttgca agaagagtc cccagagact gggaccccca gccccctgggg cctcccaccc    1560 caggagtccc agacctggtg gattttcagc caccccctga gctggtgctg cgagaggctg   1620
gggaggaggt ccctgacgct ggccccaggg agggagtcag tttcccctgg tccaggcctc   1680
ctgggcaggg ggagttcagg gcccttaatg ctcgcctgcc cctgaacact gatgcctact   1740
tgtccctcca agaactccag ggtcaggacc caactcactt ggtgtagaca gatgccagg     1800 gtgggaggca ggcagctgcc tgctctgcgc cgagcctcag aaggaccctg ttgagggtcc   1860
tcagtccact gctgaggaca ctcagtgtcc agttgcagct ggacttctcc acccggatgg   1920
ccccacccca gtcctgcaca cttggtccat ccatttccaa acctccactg ctgctcccgg   1980
gtcctgctgc ccgagccagg aactgtgtgt gttgcagggg ggcagtaact ccccaactcc   2040
ctcgttaatc acaggatccc acgaattag gctcagaagc atcgctcctc tccagccctg    2100
cagctattca ccaatatcag tcctcgcgg tctccagggc tccctgccct gacctcttcc    2160
ctgggttttc tgccccagcc tcctccttcc ctcccctccc cgtccacagg gcagcctgag   2220
```

```
cgtgctttcc aaaacccaaa tatggccacg ctcccctcg gttcaaaacc ttgcacaggt    2280
cccactgccc tcagcccac ttctcagcct ggtacttgta cctccggtgt cgtgtgggga    2340 catcccttc tgcaatcctc cctaccgtcc tcctgagcca ctcagagctc cctcacaccc    2400
cctctgttgc acatgctatt ccctggggct gctgtgcgct ccccctcatc taggtgacaa    2460
acttccctga ctcttcaagt gccggttttg cttctcctgg agggaagcac tgcctccctt    2520
aatctgccag aaacttctag cgtcagtgct ggagggagaa gctgtcaggg acccagggcg    2580
cctggagaaa gaggccctgt tactattcct ttgggatctc tgaggcctca gagtgcttgg    2640
ctgctgtatc tttaatgctg gggcccaagt aagggcacag atccccccac aaagtggatg    2700
cctgctgcat cttcccacag tggcttcaca gacccacaag agaagctgat ggggagtaaa    2760
ccctggagtc cgaggcccag gcagcagccc cgcctagtgg tgggccctga tgctgccagg    2820
cctgggacct cccactgccc cctccactgg aggggtctcc tctgcagctc agggactggc    2880
acactggcct ccagaagggc agctccacag ggcagggcct cattatttt cactgcccca    2940 gacacagtgc ccaacacccc gtcgtatacc ctggatgaac gaattaatta cctggcacca    3000
cctcgtctgg gctccctgcg cctgacattc acacagagag gcagagtccc gtgcccatta    3060
ggtctggcat gcccctcct gcaagggct caacccccta ccccgacccc tccacgtatc    3120
tttcctaggc agatcacgtt gcaatggctc aaacaacatt ccaccccagc aggacagtga    3180
ccccagtccc agctaactct gacctgggag ccctcaggca cctgcactta caggccttgc    3240
tcacagctga ttgggcacct gaccacacgc cccacaggc tctgaccagc agcctatgag    3300
ggggtttggc accaagctct gtccaatcag gtaggctggg cctgaactag ccaatcagat    3360
caactctgtc ttgggcgttt gaactcaggg agggaggccc ttgggagcag gtgcttgtgg    3420
acaaggctcc acaagcgttg agccttggaa aggtagacaa gcgttgagcc actaagcaga    3480
ggaccttggg ttcccaatac aaaaatacct actgctgaga gggctgctga ccatttggtc    3540
aggattcctg ttgcctttat atccaaaata aactcccctt tcttgaggtt gtctgagtct    3600
tgggtctatg ccttgaaaaa agctgaatta ttggacagtc tcacctcctg ccatagggtc    3660
ctgaatgttt cagaccacaa ggggctccac acctttgctg tgtgttctgg ggcaacctac    3720
taatcctctc tgcaagtcgg tctccttatc cccccaaatg gaaattgtat ttgccttctc    3780 cacttttggga ggctcccact tcttgggagg gttacatttt ttaagtctta atcatttgtg    3840
acatatgtat ctatacatcc gtatctttta atgatccgtg tgtaccatct ttgtgattat    3900
ttccttaata ttttttcttt aagtcagttc attttcgttg aaatacattt atttaaagaa    3960
aaatctttgt tactctgtaa atgaaaaaac ccattttcgc tataaataaa aggtaactgt    4020
acaaaataag tacaatgcaa caaaaaaaa                                    4050
```

<210> SEQ ID NO 22
<211> LENGTH: 267
<212> TYPE: PRT
<213> ORGANISM: Homo sapiens

<400> SEQUENCE: 22

Met Ala Pro Arg Arg Ala Arg Gly Cys Arg Thr Leu Gly Leu Pro Ala
1               5                   10                  15

Leu Leu Leu Leu Leu Leu Leu Arg Pro Pro Ala Thr Arg Gly Ile Thr
                20                  25                  30

Cys Pro Pro Pro Met Ser Val Glu His Ala Asp Ile Trp Val Lys Ser
            35                  40                  45

```
Tyr Ser Leu Tyr Ser Arg Glu Arg Tyr Ile Cys Asn Ser Gly Phe Lys
         50                  55                  60

Arg Lys Ala Gly Thr Ser Ser Leu Thr Glu Cys Val Leu Asn Lys Ala
 65                  70                  75                  80

Thr Asn Val Ala His Trp Thr Thr Pro Ser Leu Lys Cys Ile Arg Asp
                     85                  90                  95

Pro Ala Leu Val His Gln Arg Pro Ala Pro Ser Thr Val Thr Thr
                100                 105                 110

Ala Gly Val Thr Pro Gln Pro Glu Ser Leu Ser Pro Ser Gly Lys Glu
                115                 120                 125

Pro Ala Ala Ser Ser Pro Ser Ser Asn Asn Thr Ala Ala Thr Thr Ala
                130                 135                 140

Ala Ile Val Pro Gly Ser Gln Leu Met Pro Ser Lys Ser Pro Ser Thr
145                 150                 155                 160

Gly Thr Thr Glu Ile Ser Ser His Glu Ser Ser His Gly Thr Pro Ser
                    165                 170                 175

Gln Thr Thr Ala Lys Asn Trp Glu Leu Thr Ala Ser Ala Ser His Gln
                180                 185                 190

Pro Pro Gly Val Tyr Pro Gln Gly His Ser Asp Thr Thr Val Ala Ile
                195                 200                 205

Ser Thr Ser Thr Val Leu Leu Cys Gly Leu Ser Ala Val Ser Leu Leu
210                 215                 220

Ala Cys Tyr Leu Lys Ser Arg Gln Thr Pro Pro Leu Ala Ser Val Glu
225                 230                 235                 240

Met Glu Ala Met Glu Ala Leu Pro Val Thr Trp Gly Thr Ser Ser Arg
                245                 250                 255

Asp Glu Asp Leu Glu Asn Cys Ser His His Leu
                260                 265

<210> SEQ ID NO 23
<211> LENGTH: 234
<212> TYPE: PRT
<213> ORGANISM: Homo sapiens

<400> SEQUENCE: 23

Met Ala Pro Arg Arg Ala Arg Gly Cys Arg Thr Leu Gly Leu Pro Ala
 1               5                  10                  15

Leu Leu Leu Leu Leu Leu Leu Arg Pro Pro Ala Thr Arg Gly Ile Thr
                 20                  25                  30

Cys Pro Pro Pro Met Ser Val Glu His Ala Asp Ile Trp Val Lys Ser
             35                  40                  45

Tyr Ser Leu Tyr Ser Arg Glu Arg Tyr Ile Cys Asn Ser Gly Phe Lys
         50                  55                  60

Arg Lys Ala Gly Thr Ser Ser Leu Thr Glu Cys Val Leu Asn Lys Ala
 65                  70                  75                  80

Thr Asn Val Ala His Trp Thr Thr Pro Ser Leu Lys Cys Ile Lys Pro
                     85                  90                  95

Ala Ala Ser Ser Pro Ser Ser Asn Asn Thr Ala Ala Thr Thr Ala Ala
                100                 105                 110

Ile Val Pro Gly Ser Gln Leu Met Pro Ser Lys Ser Pro Ser Thr Gly
                115                 120                 125

Thr Thr Glu Ile Ser Ser His Glu Ser Ser His Gly Thr Pro Ser Gln
130                 135                 140

Thr Thr Ala Lys Asn Trp Glu Leu Thr Ala Ser Ala Ser His Gln Pro
```

```
                145                 150                 155                 160
Pro Gly Val Tyr Pro Gln Gly His Ser Asp Thr Thr Val Ala Ile Ser
                165                 170                 175

Thr Ser Thr Val Leu Leu Cys Gly Leu Ser Ala Val Ser Leu Leu Ala
            180                 185                 190

Cys Tyr Leu Lys Ser Arg Gln Thr Pro Pro Leu Ala Ser Val Glu Met
            195                 200                 205

Glu Ala Met Ala Leu Pro Val Thr Trp Gly Thr Ser Ser Arg Asp
210                 215                 220

Glu Asp Leu Glu Asn Cys Ser His His Leu
225                 230

<210> SEQ ID NO 24
<211> LENGTH: 252
<212> TYPE: PRT
<213> ORGANISM: Homo sapiens

<400> SEQUENCE: 24

Met Ala Pro Arg Arg Ala Arg Gly Cys Arg Thr Leu Gly Leu Pro Ala
1               5                   10                  15

Leu Leu Leu Leu Leu Leu Leu Arg Pro Pro Ala Thr Arg Gly Ile Thr
            20                  25                  30

Cys Pro Pro Pro Met Ser Val Glu His Ala Asp Ile Trp Val Lys Ser
            35                  40                  45

Tyr Ser Leu Tyr Ser Arg Glu Arg Tyr Ile Cys Asn Ser Gly Phe Lys
        50                  55                  60

Arg Lys Ala Gly Thr Ser Ser Leu Thr Glu Cys Val Leu Asn Lys Ala
65                  70                  75                  80

Thr Asn Val Ala His Trp Thr Thr Pro Ser Leu Lys Cys Ile Arg Asp
                85                  90                  95

Pro Ala Leu Val His Gln Arg Pro Ala Pro Pro Ser Thr Val Thr Thr
            100                 105                 110

Ala Gly Val Thr Pro Gln Pro Glu Ser Leu Ser Pro Ser Gly Lys Glu
        115                 120                 125

Pro Ala Ala Ser Ser Pro Ser Ser Asn Asn Thr Ala Ala Thr Thr Ala
    130                 135                 140

Ala Ile Val Pro Gly Ser Gln Leu Met Pro Ser Lys Ser Pro Ser Thr
145                 150                 155                 160

Gly Thr Thr Glu Ile Ser Ser His Glu Ser Ser His Gly Thr Pro Ser
                165                 170                 175

Gln Thr Thr Ala Lys Asn Trp Glu Leu Thr Ala Ser Ala Ser His Gln
            180                 185                 190

Pro Pro Gly Val Tyr Pro Gln Gly His Ser Asp Thr Thr Val Ala Ile
        195                 200                 205

Ser Thr Ser Thr Val Leu Leu Cys Gly Leu Ser Ala Val Ser Leu Leu
    210                 215                 220

Ala Cys Tyr Leu Lys Ser Arg Ala Ser Val Cys Ser Cys His Pro Arg
225                 230                 235                 240

Ser Ala Gly His Thr Cys Ser Val Gly Ser Val Cys
                245                 250

<210> SEQ ID NO 25
<211> LENGTH: 219
<212> TYPE: PRT
<213> ORGANISM: Homo sapiens
```

<400> SEQUENCE: 25

Met Ala Pro Arg Arg Ala Arg Gly Cys Arg Thr Leu Gly Leu Pro Ala
1               5                   10                  15

Leu Leu Leu Leu Leu Leu Leu Arg Pro Pro Ala Thr Arg Gly Ile Thr
            20                  25                  30

Cys Pro Pro Met Ser Val Glu His Ala Asp Ile Trp Val Lys Ser
        35                  40                  45

Tyr Ser Leu Tyr Ser Arg Glu Arg Tyr Ile Cys Asn Ser Gly Phe Lys
    50                  55                  60

Arg Lys Ala Gly Thr Ser Ser Leu Thr Glu Cys Val Leu Asn Lys Ala
65                  70                  75                  80

Thr Asn Val Ala His Trp Thr Thr Pro Ser Leu Lys Cys Ile Lys Pro
                85                  90                  95

Ala Ala Ser Ser Pro Ser Ser Asn Asn Thr Ala Ala Thr Ala Ala
                100                 105                 110

Ile Val Pro Gly Ser Gln Leu Met Pro Ser Lys Ser Pro Ser Thr Gly
            115                 120                 125

Thr Thr Glu Ile Ser Ser His Glu Ser Ser His Gly Thr Pro Ser Gln
        130                 135                 140

Thr Thr Ala Lys Asn Trp Glu Leu Thr Ala Ser Ala Ser His Gln Pro
145                 150                 155                 160

Pro Gly Val Tyr Pro Gln Gly His Ser Asp Thr Thr Val Ala Ile Ser
                165                 170                 175

Thr Ser Thr Val Leu Leu Cys Gly Leu Ser Ala Val Ser Leu Leu Ala
            180                 185                 190

Cys Tyr Leu Lys Ser Arg Ala Ser Val Cys Ser Cys His Pro Arg Ser
        195                 200                 205

Ala Gly His Thr Cys Ser Val Gly Ser Val Cys
            210                 215

<210> SEQ ID NO 26
<211> LENGTH: 202
<212> TYPE: PRT
<213> ORGANISM: Homo sapiens

<400> SEQUENCE: 26

Met Ala Pro Arg Arg Ala Arg Gly Cys Arg Thr Leu Gly Leu Pro Ala
1               5                   10                  15

Leu Leu Leu Leu Leu Leu Leu Arg Pro Pro Ala Thr Arg Gly Asp Pro
            20                  25                  30

Ala Leu Val His Gln Arg Pro Ala Pro Ser Thr Val Thr Thr Ala
        35                  40                  45

Gly Val Thr Pro Gln Pro Glu Ser Leu Ser Pro Ser Gly Lys Glu Pro
    50                  55                  60

Ala Ala Ser Ser Pro Ser Ser Asn Asn Thr Ala Ala Thr Ala Ala
65                  70                  75                  80

Ile Val Pro Gly Ser Gln Leu Met Pro Ser Lys Ser Pro Ser Thr Gly
                85                  90                  95

Thr Thr Glu Ile Ser Ser His Glu Ser Ser His Gly Thr Pro Ser Gln
            100                 105                 110

Thr Thr Ala Lys Asn Trp Glu Leu Thr Ala Ser Ala Ser His Gln Pro
        115                 120                 125

Pro Gly Val Tyr Pro Gln Gly His Ser Asp Thr Thr Val Ala Ile Ser
    130                 135                 140

Thr Ser Thr Val Leu Leu Cys Gly Leu Ser Ala Val Ser Leu Leu Ala
145                 150                 155                 160

Cys Tyr Leu Lys Ser Arg Gln Thr Pro Pro Leu Ala Ser Val Glu Met
                165                 170                 175

Glu Ala Met Glu Ala Leu Pro Val Thr Trp Gly Thr Ser Ser Arg Asp
            180                 185                 190

Glu Asp Leu Glu Asn Cys Ser His His Leu
            195                 200

<210> SEQ ID NO 27
<211> LENGTH: 187
<212> TYPE: PRT
<213> ORGANISM: Homo sapiens

<400> SEQUENCE: 27

Met Ala Pro Arg Arg Ala Arg Gly Cys Arg Thr Leu Gly Leu Pro Ala
1               5                   10                  15

Leu Leu Leu Leu Leu Leu Leu Arg Pro Pro Ala Thr Arg Gly Asp Pro
            20                  25                  30

Ala Leu Val His Gln Arg Pro Ala Pro Pro Ser Thr Val Thr Thr Ala
        35                  40                  45

Gly Val Thr Pro Gln Pro Glu Ser Leu Ser Pro Ser Gly Lys Glu Pro
50                  55                  60

Ala Ala Ser Ser Pro Ser Ser Asn Asn Thr Ala Ala Thr Thr Ala Ala
65                  70                  75                  80

Ile Val Pro Gly Ser Gln Leu Met Pro Ser Lys Ser Pro Ser Thr Gly
                85                  90                  95

Thr Thr Glu Ile Ser Ser His Glu Ser Ser His Gly Thr Pro Ser Gln
            100                 105                 110

Thr Thr Ala Lys Asn Trp Glu Leu Thr Ala Ser Ala Ser His Gln Pro
        115                 120                 125

Pro Gly Val Tyr Pro Gln Gly His Ser Asp Thr Thr Val Ala Ile Ser
130                 135                 140

Thr Ser Thr Val Leu Leu Cys Gly Leu Ser Ala Val Ser Leu Leu Ala
145                 150                 155                 160

Cys Tyr Leu Lys Ser Arg Ala Ser Val Cys Ser Cys His Pro Arg Ser
                165                 170                 175

Ala Gly His Thr Cys Ser Val Gly Ser Val Cys
            180                 185

<210> SEQ ID NO 28
<211> LENGTH: 169
<212> TYPE: PRT
<213> ORGANISM: Homo sapiens

<400> SEQUENCE: 28

Met Ala Pro Arg Arg Ala Arg Gly Cys Arg Thr Leu Gly Leu Pro Ala
1               5                   10                  15

Leu Leu Leu Leu Leu Leu Leu Arg Pro Ala Thr Arg Glu Pro Ala
            20                  25                  30

Ala Ser Ser Pro Ser Ser Asn Asn Thr Ala Ala Thr Thr Ala Ala Ile
        35                  40                  45

Val Pro Gly Ser Gln Leu Met Pro Ser Lys Ser Pro Ser Thr Gly Thr
    50                  55                  60

Thr Glu Ile Ser Ser His Glu Ser Ser His Gly Thr Pro Ser Gln Thr
65                  70                  75                  80

```
Thr Ala Lys Asn Trp Glu Leu Thr Ala Ser Ala Ser His Gln Pro Pro
                85                  90                  95

Gly Val Tyr Pro Gln Gly His Ser Asp Thr Thr Val Ala Ile Ser Thr
            100                 105                 110

Ser Thr Val Leu Leu Cys Gly Leu Ser Ala Val Ser Leu Leu Ala Cys
        115                 120                 125

Tyr Leu Lys Ser Arg Gln Thr Pro Pro Leu Ala Ser Val Glu Met Glu
    130                 135                 140

Ala Met Glu Ala Leu Pro Val Thr Trp Gly Thr Ser Ser Arg Asp Glu
145                 150                 155                 160

Asp Leu Glu Asn Cys Ser His His Leu
                165
```

<210> SEQ ID NO 29
<211> LENGTH: 154
<212> TYPE: PRT
<213> ORGANISM: Homo sapiens

<400> SEQUENCE: 29

```
Met Ala Pro Arg Arg Ala Arg Gly Cys Arg Thr Leu Gly Leu Pro Ala
1               5                   10                  15

Leu Leu Leu Leu Leu Leu Leu Arg Pro Pro Ala Thr Arg Glu Pro Ala
                20                  25                  30

Ala Ser Ser Pro Ser Ser Asn Asn Thr Ala Ala Thr Thr Ala Ala Ile
            35                  40                  45

Val Pro Gly Ser Gln Leu Met Pro Ser Lys Ser Pro Ser Thr Gly Thr
    50                  55                  60

Thr Glu Ile Ser Ser His Glu Ser Ser His Gly Thr Pro Ser Gln Thr
65                  70                  75                  80

Thr Ala Lys Asn Trp Glu Leu Thr Ala Ser Ala Ser His Gln Pro Pro
                85                  90                  95

Gly Val Tyr Pro Gln Gly His Ser Asp Thr Thr Val Ala Ile Ser Thr
            100                 105                 110

Ser Thr Val Leu Leu Cys Gly Leu Ser Ala Val Ser Leu Leu Ala Cys
        115                 120                 125

Tyr Leu Lys Ser Arg Ala Ser Val Cys Ser Cys His Pro Arg Ser Ala
    130                 135                 140

Gly His Thr Cys Ser Val Gly Ser Val Cys
145                 150
```

<210> SEQ ID NO 30
<211> LENGTH: 231
<212> TYPE: PRT
<213> ORGANISM: Homo sapiens

<400> SEQUENCE: 30

```
Met Ser Val Glu His Ala Asp Ile Trp Val Lys Ser Tyr Ser Leu Tyr
1               5                   10                  15

Ser Arg Glu Arg Tyr Ile Cys Asn Ser Gly Phe Lys Arg Lys Ala Gly
                20                  25                  30

Thr Ser Ser Leu Thr Glu Cys Val Leu Asn Lys Ala Thr Asn Val Ala
            35                  40                  45

His Trp Thr Thr Pro Ser Leu Lys Cys Ile Arg Asp Pro Ala Leu Val
    50                  55                  60

His Gln Arg Pro Ala Pro Pro Ser Thr Val Thr Thr Ala Gly Val Thr
65                  70                  75                  80
```

Pro Gln Pro Glu Ser Leu Ser Pro Ser Gly Lys Glu Pro Ala Ala Ser
             85                  90                  95

Ser Pro Ser Ser Asn Asn Thr Ala Ala Thr Thr Ala Ala Ile Val Pro
            100                 105                 110

Gly Ser Gln Leu Met Pro Ser Lys Ser Pro Ser Thr Gly Thr Thr Glu
        115                 120                 125

Ile Ser Ser His Glu Ser Ser His Gly Thr Pro Ser Gln Thr Thr Ala
    130                 135                 140

Lys Asn Trp Glu Leu Thr Ala Ser Ala Ser His Gln Pro Pro Gly Val
145                 150                 155                 160

Tyr Pro Gln Gly His Ser Asp Thr Thr Val Ala Ile Ser Thr Ser Thr
                165                 170                 175

Val Leu Leu Cys Gly Leu Ser Ala Val Ser Leu Leu Ala Cys Tyr Leu
            180                 185                 190

Lys Ser Arg Gln Thr Pro Pro Leu Ala Ser Val Glu Met Glu Ala Met
        195                 200                 205

Glu Ala Leu Pro Val Thr Trp Gly Thr Ser Ser Arg Asp Glu Asp Leu
    210                 215                 220

Glu Asn Cys Ser His His Leu
225                 230

<210> SEQ ID NO 31
<211> LENGTH: 1657
<212> TYPE: DNA
<213> ORGANISM: Homo sapiens

<400> SEQUENCE: 31
aaaagcgaaa gcgaatgcga ctggcggggc ggcaggtccc agagcagcgc tcgccacctc    60
cccccggcct gggcagcgct cgcccgggga gtccagcggt gtcctgtgga gctgccgcca    120
tggccccgcg gcgggcgcgc ggctgccgga ccctcggtct cccggcgctg ctactgctgc    180
tgctgctccg gccgccggcg acgcggggca tcacgtgccc tccccccatg tccgtggaac    240
acgcagacat ctgggtcaag agctacagct tgtactccag ggagcggtac atttgtaact    300
ctggtttcaa gcgtaaagcc ggcacgtcca gcctgacgga gtgcgtgttg aacaaggcca    360
cgaatgtcgc ccactggaca acccccagtc tcaaatgcat tagagaccct gccctggttc    420
accaaaggcc agcgccaccc tccacagtaa cgacggcagg ggtgacccca cagcagagga    480
gcctctcccc ttctggaaaa gagcccgcag cttcatctcc cagctcaaac aacacagcgg    540
ccacaacagc agctattgtc ccgggctccc agctgatgcc ttcaaaatca ccttccacag    600
gaaccacaga gataagcagt catgagtcct cccacggcac ccctctcag acaacagcca     660 agaactggga actcacagca tccgcctccc accagccgcc aggtgtgtat ccacagggcc    720
acagcgacac cactgtggct atctccacgt ccactgtcct gctgtgtggg ctgagcgctg    780
tgtctctcct ggcatgctac ctcaagtcaa ggcaaactcc cccgctggcc agcgttgaaa    840
tggaagccat ggaggctctg ccggtgactt ggggggaccag cagcagagat gaagacttgg    900
aaaactgctc tcaccaccta tgaaactcgg ggaaaccagc cagctaagt ccggagtgaa     960 ggagcctctc tgctttagct aaagacgact gagaagaggt gcaaggaagc gggctccagg    1020
agcaagctca ccaggcctct cagaagtccc agcaggatct cacggactgc cgggtcggcg    1080
cctcctgcgc gagggagcag gttctccgca ttcccatggg caccacctgc ctgcctgtcg    1140
tgccttggac ccagggccca gcttcccagg agagaccaaa ggcttctgag caggattttt    1200
atttcattac agtgtgagct gcctggaata catgtggtaa tgaaataaaa accctgcccc    1260

```
gaatcttccg tccctcatcc taactttcag ttcacagaga aaagtgacat acccaaagct   1320
ctctgtcaat tacaaggctt ctcctggcgt gggagacgtc tacagggaag acaccagcgt   1380
ttgggcttct aaccaccctg tctccagctg ctctgcacac atggacaggg acctgggaaa   1440
ggtgggagag atgctgagcc cagcgaatcc tctccattga aggattcagg aagaagaaaa   1500
ctcaactcag tgccatttta cgaatatatg cgtttatatt tatacttcct tgtctattat   1560
atctatacat tatatattat ttgtattttg acattgtacc ttgtataaac aaaataaaac   1620
atctattttc aatattttta aaatgcaaaa aaaaaaa                            1657

<210> SEQ ID NO 32
<211> LENGTH: 1558
<212> TYPE: DNA
<213> ORGANISM: Homo sapiens

<400> SEQUENCE: 32
aaaagcgaaa gcgaatgcga ctggcggggc ggcaggtccc agagcagcgc tcgccacctc     60 ccccggcct gggcagcgct cgcccgggga gtccagcggt gtcctgtgga gctgccgcca    120
tggccccgcg gcgggcgcgc ggctgccgga ccctcggtct cccggcgctg ctactgctgc    180
tgctgctccg gccgccggcg acgcggggca tcacgtgccc tcccccatg tccgtggaac    240 acgcagacat ctgggtcaag agctacagct tgtactccag ggagcggtac atttgtaact    300
ctggtttcaa gcgtaaagcc ggcacgtcca gcctgacgga gtgcgtgttg aacaaggcca    360
cgaatgtcgc ccactggaca acccccagtc tcaaatgcat taagcccgca gcttcatctc    420
ccagctcaaa caacacagcg gccacaacag cagctattgt cccgggctcc cagctgatgc    480
cttcaaaatc accttccaca ggaaccacag agataagcag tcatgagtcc tcccacggca    540 cccctctca gacaacagcc aagaactggg aactcacagc atccgcctcc accagccgc    600 caggtgtgta tccacagggc cacagcgaca ccactgtggc tatctccacg tccactgtcc    660
tgctgtgtgg gctgagcgct gtgtctctcc tggcatgcta cctcaagtca aggcaaactc    720
ccccgctggc cagcgttgaa atggaagcca tggaggctct gccggtgact gggggaccca    780
gcagcagaga tgaagacttg gaaaactgct ctcaccacct atgaaactcg ggaaaccag    840 cccagctaag tccggagtga aggagcctct ctgctttagc taaagacgac tgagaagagg    900
tgcaaggaag cgggctccag gagcaagctc accaggcctc tcagaagtcc cagcaggatc    960
tcacggactg ccgggtcggc gcctcctgcg cgagggagca ggttctccgc attcccatgg   1020
gcaccacctg cctgcctgtc gtgccttgga cccagggccc agcttccag gagagaccaa   1080 aggcttctga gcaggatttt tatttcatta cagtgtgagc tgcctggaat acatgtggta   1140
atgaaataaa aaccctgccc cgaatcttcc gtccctcatc ctaactttca gttcacagag   1200
aaaagtgaca tacccaaagc tctctgtcaa ttacaaggct tctcctggcg tgggagacgt   1260
ctacagggaa gacaccagcg tttgggcttc taaccaccct gtctccagct gctctgcaca   1320
catggacagg gacctgggaa aggtgggaga gatgctgagc ccagcgaatc ctctccattg   1380
aaggattcag gaagaagaaa actcaactca gtgccatttt acgaatatat gcgtttatat   1440
ttatacttcc ttgtctatta tatctataca ttatatatta tttgtatttt gacattgtac   1500
cttgtataaa caaaataaaa catctatttt caatattttt aaaatgcaaa aaaaaaaa    1558

<210> SEQ ID NO 33
<211> LENGTH: 1861
<212> TYPE: DNA
```

<213> ORGANISM: Homo sapiens

<400> SEQUENCE: 33

```
agctgcagca ggaattcggc gaagtggcgg agctggggcc ccagcgggcg ccggggggccg      60
cgggagccag caggtggcgg gggctgcgct ccgcccgggc cagagcgcac caggcaggtg     120
cccgcgcctc cgcaccgcgg cgacacctcc gcgggcactc acccaggccg gccgctcaca     180
accgagcgca gggccgcgga gggagaccag gaaagccgaa ggcggagcag ctggaggcga     240
ccagcgccgg gcgaggtcaa gtggatccga gccgcagaga gggctggaga gagtctgctc     300
tccgatgact ttgcccactc tcttcgcagt ggggacaccg gaccgagtgc acactggagg     360
tcccagagca cgacgagcgc ggaggaccgg gaggctcccg ggcttgcgtg ggcatcacgt     420
gccctccccc catgtccgtg gaacacgcag acatctgggt caagagctac agcttgtact     480
ccagggagcg gtacatttgt aactctggtt tcaagcgtaa agccggcacg tccagcctga     540
cggagtgcgt gttgaacaag gccacgaatg tcgcccactg gacaaccccc agtctcaaat     600
gcattagaga ccctgccctg gttcaccaaa ggccagcgcc accctccaca gtaacgacgg     660
cagggggtgac cccacagcca gagagcctct ccccttctgg aaaagagccc gcagcttcat     720
ctcccagctc aaacaacaca gcggccacaa cagcagctat tgtcccgggc tcccagctga     780
tgccttcaaa atcaccttcc acaggaacca cagagataag cagtcatgag tcctcccacg     840
gcacccccctc tcagacaaca gccaagaact gggaactcac agcatccgcc tcccaccagc     900
cgccaggtgt gtatccacag ggccacagcg acaccactgt ggctatctcc acgtccactg     960
tcctgctgtg tgggctgagc gctgtgtctc tcctggcatg ctacctcaag tcaaggcaaa    1020
ctcccccgct ggccagcgtt gaaatggaag ccatggaggc tctgccggtg acttggggga    1080
ccagcagcag agatgaagac ttggaaaact gctctcacca cctatgaaac tcggggaaac    1140
cagcccagct aagtccggag tgaaggagcc tctctgcttt agctaaagac gactgagaag    1200
aggtgcaagg aagcgggctc caggagcaag ctcaccaggc ctctcagaag tcccagcagg    1260
atctcacgga ctgccgggtc ggcgcctcct gcgcgaggga gcaggttctc cgcattccca    1320
tgggcaccac ctgcctgcct gtcgtgcctt ggacccaggg cccagcttcc caggagagac    1380
caaaggcttc tgagcaggat ttttatttca ttacagtgtg agctgcctgg aatacatgtg    1440
gtaatgaaat aaaaaccctg ccccgaatct tccgtccctc atcctaactt tcagttcaca    1500
gagaaaagtg acatacccaa agctctctgt caattacaag gcttctcctg gcgtgggaga    1560
cgtctacagg gaagacacca gcgtttgggc ttctaaccac cctgtctcca gctgctctgc    1620
acacatggac agggacctgg gaaaggtggg agagatgctg agcccagcga atcctctcca    1680
ttgaaggatt caggaagaag aaaactcaac tcagtgccat tttacgaata tatgcgttta    1740
tatttatact tccttgtcta ttatatctat acattatata ttatttgtat tttgacattg    1800
taccttgtat aaacaaaata aaacatctat tttcaatatt tttaaaatgc aaaaaaaaa    1860
a                                                                    1861
```

<210> SEQ ID NO 34
<211> LENGTH: 1810
<212> TYPE: DNA
<213> ORGANISM: Homo sapiens

<400> SEQUENCE: 34

```
aaaagcgaaa gcgaatgcga ctggcggggc ggcaggtccc agagcagcgc tcgccacctc      60
cccccggcct gggcagcgct cgcccgggga gtccagcggt gtcctgtgga gctgccgcca     120
```

```
tggccccgcg gcgggcgcgc ggctgccgga ccctcggtct cccggcgctg ctactgctgc      180
tgctgctccg gccgccggcg acgcgggatg caagagacag gctggctgtc ctggcgggaa      240
ggagcagaat atctgaaagc ttcaaccatg aggtccagac acgaggcc tgcgtgagac        300
tcaggacaat ggaaaactgc ccccagtgcc accaccatcg acaagcagg cagcaagcag       360
gcatcacgtg ccctccccc atgtccgtgg aacacgcaga catctgggtc aagagctaca       420
gcttgtactc cagggagcgg tacatttgta actctggttt caagcgtaaa gccggcacgt      480
ccagcctgac ggagtgcgtg ttgaacaagg ccacgaatgt cgcccactgg acaaccccca     540
gtctcaaatg cattagagac cctgccctgg ttcaccaaag ccagcgcca ccctccacag       600
taacgacggc aggggtgacc ccacagccag agagcctctc cccttctgga aagagcccg       660
cagcttcatc tcccagctca acaacacag cggccacaac agcagctatt gtcccgggct      720
cccagctgat gccttcaaaa tcaccttcca caggaaccac agagataagc agtcatgagt      780
cctcccacgg cacccctct cagacaacag ccaagaactg gaactcaca gcatccgcct       840
cccaccagcc gccaggtgtg tatccacagg gccacagcga caccactgtg gctatctcca      900
cgtccactgt cctgctgtgt gggctgagcg ctgtgtctct cctggcatgc tacctcaagt      960
caaggcaaac tcccccgctg gccagcgttg aaatggaagc catggaggct ctgccggtga     1020
cttggggggac cagcagcaga gatgaagact tggaaaactg ctctcaccac ctatgaaact    1080
cggggaaacc agcccagcta agtccggagt gaaggagcct ctctgcttta gctaaagacg     1140
actgagaaga ggtgcaagga agcgggctcc aggagcaagc tcaccaggcc tctcagaagt    1200
cccagcagga tctcacggac tgccgggtcg gcgcctcctg cgcgagggag caggttctcc    1260
gcattcccat gggcaccacc tgcctgcctg tcgtgccttg gacccagggc ccagcttccc    1320
aggagagacc aaaggcttct gagcaggatt tttatttcat tacagtgtga gctgcctgga    1380
atacatgtgg taatgaaata aaaccctgc cccgaatctt ccgtccctca tcctaacttt    1440
cagttcacag agaaaagtga catacccaaa gctctctgtc aattacaagg cttctcctgg    1500
cgtgggagac gtctacaggg aagacaccag cgtttgggct tctaaccacc ctgtctccag   1560
ctgctctgca cacatggaca gggacctggg aaaggtggga gagatgctga gcccagcgaa    1620
tcctctccat tgaaggattc aggaagaaga aaactcaact cagtgccatt ttacgaatat    1680
atgcgtttat atttatactt ccttgtctat tatatctata cattatatat tatttgtatt    1740
ttgacattgt accttgtata aacaaaataa aacatctatt ttcaatattt ttaaaatgca    1800
aaaaaaaaaa                                                            1810
```

<210> SEQ ID NO 35
<211> LENGTH: 234
<212> TYPE: PRT
<213> ORGANISM: Homo sapiens

<400> SEQUENCE: 35

Met Ala Pro Arg Arg Ala Arg Gly Cys Arg Thr Leu Gly Leu Pro Ala
1               5                   10                  15

Leu Leu Leu Leu Leu Leu Leu Arg Pro Pro Ala Thr Arg Gly Ile Thr
            20                  25                  30

Cys Pro Pro Pro Met Ser Val Glu His Ala Asp Ile Trp Val Lys Ser
        35                  40                  45

Tyr Ser Leu Tyr Ser Arg Glu Arg Tyr Ile Cys Asn Ser Gly Phe Lys
    50                  55                  60

```
Arg Lys Ala Gly Thr Ser Ser Leu Thr Glu Cys Val Leu Asn Lys Ala
 65                  70                  75                  80

Thr Asn Val Ala His Trp Thr Thr Pro Ser Leu Lys Cys Ile Lys Pro
                 85                  90                  95

Ala Ala Ser Ser Pro Ser Ser Asn Asn Thr Ala Ala Thr Thr Ala Ala
            100                 105                 110

Ile Val Pro Gly Ser Gln Leu Met Pro Ser Lys Ser Pro Ser Thr Gly
        115                 120                 125

Thr Thr Glu Ile Ser Ser Glu Ser Ser His Gly Thr Pro Ser Gln
    130                 135                 140

Thr Thr Ala Lys Asn Trp Glu Leu Thr Ala Ser Ala Ser His Gln Pro
145                 150                 155                 160

Pro Gly Val Tyr Pro Gln Gly His Ser Asp Thr Thr Val Ala Ile Ser
                165                 170                 175

Thr Ser Thr Val Leu Leu Cys Gly Leu Ser Ala Val Ser Leu Leu Ala
            180                 185                 190

Cys Tyr Leu Lys Ser Arg Gln Thr Pro Pro Leu Ala Ser Val Glu Met
        195                 200                 205

Glu Ala Met Glu Ala Leu Pro Val Thr Trp Gly Thr Ser Ser Arg Asp
210                 215                 220

Glu Asp Leu Glu Asn Cys Ser His His Leu
225                 230
```

```
<210> SEQ ID NO 36
<211> LENGTH: 115
<212> TYPE: PRT
<213> ORGANISM: Homo sapiens

<400> SEQUENCE: 36

Met Phe His Val Ser Phe Arg Tyr Ile Phe Gly Leu Pro Pro Leu Ile
1               5                   10                  15

Leu Val Leu Leu Pro Val Ala Ser Ser Asp Cys Asp Ile Glu Gly Lys
            20                  25                  30

Asp Gly Lys Gln Tyr Glu Ser Val Leu Met Val Ser Ile Asp Gln Leu
        35                  40                  45

Leu Asp Ser Met Lys Glu Ile Gly Ser Asn Cys Leu Asn Asn Glu Phe
 50                  55                  60

Asn Phe Phe Lys Arg His Ile Cys Asp Ala Asn Lys Glu Gly Met Phe Leu Lys
65                  70                  75                  80

Ser Leu Lys Glu Gln Lys Lys Leu Asn Asp Leu Cys Phe Leu Lys Arg
            85                  90                  95

Leu Leu Gln Glu Ile Lys Thr Cys Trp Asn Lys Ile Leu Met Gly Thr
        100                 105                 110

Lys Glu His
        115
```

```
<210> SEQ ID NO 37
<211> LENGTH: 7
<212> TYPE: PRT
<213> ORGANISM: Artificial Sequence
<220> FEATURE:
<223> OTHER INFORMATION: Linker Polypeptide in soluble human IL-7R alpha
      (CD127)-Fc chimera

<400> SEQUENCE: 37

Ile Ile Glu Gly Arg Met Asp
1               5
```

```
<210> SEQ ID NO 38
<211> LENGTH: 7
<212> TYPE: PRT
<213> ORGANISM: Artificial Sequence
<220> FEATURE:
<223> OTHER INFORMATION: Fusion Linker in soluble human IL-15R alpha-Fc
      chimera

<400> SEQUENCE: 38

Ile Glu Gly Arg Asp Met Asp
1               5
```

THERAPEUTICS FOR OCULAR IMMUNOINFLAMMATORY DISEASES

CROSS-REFERENCE TO RELATED APPLICATIONS

This application is a National Stage Application, filed under 35 U.S.C. § 371, of International Application No. PCT/US2017/012547 filed Jan. 6, 2017, which claims the priority and the benefit of U.S. Provisional Application Ser. No. 62/275,946, filed Jan. 7, 2016, which is incorporated herein by reference in its entirely and for all purposes.

STATEMENT AS TO FEDERALLY SPONSORED RESEARCH

This invention was made with government support under R01-EY20889 awarded by the National Institutes of Health. The government has certain rights in the invention.

FIELD OF THE INVENTION

The present invention relates generally to the field of ophthalmology.

INCORPORATION BY REFERENCE OF SEQUENCE LISTING

The contents of the text file named 36770-547001US_SE-QUENCE_LISTING.txt, which was created Jan. 6, 2017, and is 84.9 kilobytes in size, are hereby incorporated by reference in their entireties.

BACKGROUND

Dry Eye Disease (DED), characterized by ocular surface inflammation, remains one of the most frequent reasons leading patients to seek ophthalmic care (Am J Ophthalmol. 2007; 143:409-15). It affects approximately 5 million Americans over the age of 50 years, with millions more experiencing intermittent symptoms of dry eye (Ocul Surf 2007; 5:93-107). The disease can have a debilitating impact upon activities of daily living, and current therapeutic strategies are restricted to symptomatic relief with artificial tears, as well as non-specific corticosteroid therapy and topical cyclosporine [Restasis® (Cyclosporine Ophthalmic Emulsion)]. However, the long-term use of corticosteroids is limited by the sight-threatening side effects of raised intraocular pressure and cataracts (Curr Opin Ophthalmol 2000; 11:478-483). Additionally, tolerability issues such as burning and stinging have been reported with Restasis® (Arch Ophthalmol 2009; 127:146-152).

There remains an unmet need for novel immunomodulatory treatment methods and compositions that target specific components of the underlying immune response in ocular immunoinflammatory diseases such as DED, autoimmune uveitis, and ocular Graft Versus Host Disease (GVHD).

SUMMARY OF THE INVENTION

The present subject matter provides a novel therapeutic approach for treating memory Th17-cell mediated ocular immune inflammatory diseases. Aspects of the present subject matter provide methods and compositions for treating memory Th17 cell mediated ocular disorders (e.g. DED) in which an interleukin (IL)-7/IL-7 receptor (IL-7R) or IL-15/IL-15 receptor (IL-15R) inhibitor is administered. In some embodiments, a IL-7/IL-7R signaling inhibitor and a IL-15/IL15R inhibitor are administered.

A subject afflicted with an ocular immunoinflammatory disorder may be treated by locally administering a composition having a compound that preferentially inhibits interleukin-15 (IL-15) signal transduction and/or a compound that preferentially inhibits interleukin-7 (IL-7) signal transduction to an eye of the subject. In various embodiments, treating the ocular immunoinflammatory disorder comprises inhibiting the survival or proliferation of a Th17 cell in an eye tissue. A non-limiting example of an ocular immunoinflammatory disorder is DED.

"IL-7 signal transduction," "IL-7 signaling," or "IL-7 signaling pathway" used herein refers to the intracellular signaling pathway activated when IL-7 binds to a cell surface receptor complex comprising IL-7 R alpha and/or common gamma-chain/IL-2 R gamma (e.g., IL-7R and/or IL-2RG). IL-7 signaling is involved in the establishment and maintenance of normal immune system functions. It is required for mouse and human T cell development and homeostatic proliferation, mouse B cell development, and the generation of CD4+ and CD8+ memory T cells. Though the present subject matter is not limited by any scientific theory, the requirement of 11-7 for T cell survival has been partially attributed to its ability to induce expression of the anti-apoptotic Bcl-2, Bcl-xL, and Mcl-1 proteins. In addition, IL-7 plays a role in regulating V(D)J recombination at the TCR gamma, TCR beta, and immunoglobulin heavy chain loci.

"IL-15 signal transduction," "IL-15 signaling," or "IL-15 signaling pathway" used herein refers to the intracellular signaling pathway activated when 11-15 binds to a cell surface receptor complex comprising a unique IL-15 R alpha subunit, IL-2/IL-15 R beta, and/or the common gamma-chain/IL-2 R gamma subunit. IL-15 signaling is involved in normal immune system functions. Though the present subject matter is not limited by any scientific theory, it stimulates T cell proliferation and inhibits IL-2-mediated activation-induced cell death. In addition, IL-15 is required for the development, survival, and activation of natural killer (NK) cells, homeostasis of natural killer T (NKT) cells and intraepithelial lymphocytes, and maintenance of naïve and memory CD8+ T cells.

A compound may inhibit signal transduction by a variety of mechanisms and at different possible sites of a cell. For example, the compound that preferentially inhibits IL-7 signal transduction may inhibit initiation of IL-7 signal transduction at the cell surface of a Th17 cell and/or the compound may inhibit initiation of IL-15 signal transduction and the cell surface of a Th17 cell. In certain embodiments, the compound that preferentially inhibits IL-7 signal transduction inhibits extracellular engagement or binding of an IL-7 receptor (IL-7R) with or to IL-7 and/or the compound that preferentially inhibits IL-15 signal transduction inhibits extracellular engagement or binding of an IL-15 receptor (IL-15R) with or to IL-15.

The terms "inhibitor," "repressor" or "antagonist" or "downregulator" interchangeably refer to a substance that results in a detectably lower expression or activity level as compared to a control. In various embodiments, the inhibited expression or activity can be reduced by about 10%, 15%, 20%, 25%, 30%, 35%, 40%, 45%, 50%, 55%, 60%, 65%, 70%, 75%, 80%, 85%, 90%, 95%, 99% or more compared to the level of expression or activity in a control. In some embodiments, the inhibited expression or activity may be between about 10% and about 25%, about 10% and about 50%, about 10% and about 75%, about 1% and about 50%, about 1% and about 25%, about 25% and about 50%, 50% and about 75% or any other range between 0.5% and 99% the level of expression or activity in a control. An "inhibitor" is a compound that inhibits a cellular function (e.g., replication) e.g., by binding, partially or totally blocking stimulation, decreasing, preventing, or delaying activation, or inactivating, desensitizing, or down-regulate signal transduction, gene expression or enzymatic activity necessary for protein activity. Non-limiting examples of inhibitors include RNA interference-inducing (RNAi) molecules (e.g., siRNA, shRNA, miRNA, snoRNA), antisense oligonucleotides, aptamers (e.g., DNA aptamers and RNA aptamers), small molecules, or a polypeptide (e.g., an antibody or a soluble peptide such as the extracellular domain of a receptor or a ligand-binding portion thereof)

Non-limiting examples of inhibitors useful in aspects of the present subject matter include neutralizing antibodies, small molecules, and soluble peptides. In some embodiments, the compound that preferentially inhibits IL-7 signal transduction comprises a neutralizing anti-IL-7R antibody, a small molecule IL-7 inhibitor, a soluble peptide that binds to IL-7, or an antibody that binds to IL-7. In various embodiments, the compound that preferentially inhibits IL-15 signal transduction comprises a neutralizing anti-IL-15R antibody, a small molecule IL-15 inhibitor, a soluble peptide that binds to IL-15, or an antibody that binds to IL-15.

Subjects suffering from an ocular immune inflammatory disease may suffer from one or more symptoms. Non-limiting examples of such symptoms include a sandy or gritty feeling (e.g., self-reported by a subject) as if something is in the eye, eye dryness, heavy eyelids, stinging, itching, burning, irritation, pain, redness, inflammation, discharge, inability to cry when emotionally stressed, eye fatigue, blurred vision, or excessive watering, and wherein said method inhibits or reduces the severity of the sandy or gritty feeling as if something is in the eye, eye dryness, heavy eyelids, stinging, itching, burning, irritation, pain, redness, inflammation, discharge, inability to cry when emotionally stressed, eye fatigue, blurred vision, and excessive watering. In embodiments, the method described herein may include identifying a subject having one or more of these symptoms.

Compositions of the present subject matter can be formulated in a variety of forms. In various embodiments, the composition is in the form of a solid, an ointment, a gel, a liquid, an aerosol, a mist, a polymer, a contact lens, a film, an emulsion, or a suspension. In some embodiments, the composition is administered topically. In preferred embodiments, treatment does not comprise systemic administration or substantial dissemination to non-ocular tissue of the composition.

In certain embodiments, the number of memory Th17 cells in the eye of the subject is reduced after the composition is administered. In some embodiments, the number of memory Th17 cells in the eye of the subject is reduced by at least 1, 2, 3, 4, 5, 6, 7, 8, 9, 10, 20, 30, 40, 50, 60, 70, 80, 90, 91, 92, 93, 94, 95, 96, 97, 98, 99, or 100% or between 1-10, 1-25, 10-25, 25-50, 10-50, 50-75, or 50-100%.

Aspects of the present subject matter also relate to the combination of IL-7 and/or IL-15 inhibition with one or more inhibitors of IL-17-mediated signal transduction. Some IL-17 inhibitors reduce or block binding of IL-17 to an IL-17 receptor.

Various implementations of the present subject matter relate to inhibitors that specifically block or reduce IL-7 or IL-15-mediated signal transduction. In some embodiments, the compound that preferentially inhibits IL-7 signal transduction binds to IL-7 or IL-7R with at least 5, 10, 15, 20, 25, 30, 35, 40, 45, 50, 55, 60, 75, 80, 85, 90, 95, 100% or 2-fold, 5-fold, 10-fold, 100-fold, or 1000-fold higher affinity than IL-1, IL-2, IL-3, IL-4, IL-5, IL-6, IL-8, IL-10, IL-11, IL-12, IL-13, IL-14, IL-15, IL-16, IL-17, IL-18, IL-19, IL-20, IL-21, IL-22, IL-23, IL-24, IL, 25, IL-26, IL-27, IL-28, IL-29, IL-30, IL-31, IL-32, IL-33, IL-34, IL-35, IL-36, IL-37, IL-38 and/or, interferon gamma (IFN-γ) or a receptor thereof. In certain embodiments, the compound that preferentially inhibits IL-15 signal transduction binds IL-15 or IL-15R with at least 5, 10, 15, 20, 25, 30, 35, 40, 45, 50, 55, 60, 75, 80, 85, 90, 95, 100% or 2-fold, 5-fold, 10-fold, 100-fold, or 1000-fold higher affinity than IL-1, IL-2, IL-3, IL-4, IL-5, IL-6, IL-7, IL-8, IL-10, IL-11, IL-12, IL-13, IL-14, IL-16, IL-17, IL-18, IL-19, IL-20, IL-21, IL-22, IL-23, IL-24, IL, 25, IL-26, IL-27, IL-28, IL-29, IL-30, IL-31, IL-32, IL-33, IL-34, IL-35, IL-36, IL-37, IL-38 and/or, IFN-γ or a receptor thereof. In various embodiments, the compound that preferentially inhibits IL-7 signal transduction inhibits IL-7-mediated signal transduction at least 5, 10, 15, 20, 25, 30, 35, 40, 45, 50, 55, 60, 75, 80, 85, 90, 95, 100% or 2-fold, 5-fold, 10-fold, 100-fold, or 1000-fold more than IL-1, IL-2, IL-3, IL-4, IL-5, IL-6, IL-8, IL-10, IL-11, IL-12, IL-13, IL-14, IL-15, IL-16, IL-17, IL-18, IL-19, IL-20, IL-21, IL-22, IL-23, IL-24, IL, 25, IL-26, IL-27, IL-28, IL-29, IL-30, IL-31, IL-32, IL-33, IL-34, IL-35, IL-36, IL-37, IL-38 and/or, IFN-γ-mediated signal transduction. In some embodiments, the compound that preferentially inhibits IL-15 signal transduction inhibits IL-15-mediated signal transduction at least 5, 10, 15, 20, 25, 30, 35, 40, 45, 50, 55, 60, 75, 80, 85, 90, 95, 100% or 2-fold, 5-fold, 10-fold, 100-fold, or 1000-fold more than IL-1, IL-2, IL-3, IL-4, IL-5, IL-6, IL-7, IL-8, IL-10, IL-11, IL-12, IL-13, IL-14, IL-16, IL-17, IL-18, IL-19, IL-20, IL-21, IL-22, IL-23, IL-24, IL, 25, IL-26, IL-27, IL-28, IL-29, IL-30, IL-31, IL-32, IL-33, IL-34, IL-35, IL-36, IL-37, IL-38 and/or, IFN-γ-mediated signal transduction.

Various methods and compositions of the present subject matter do not include a Janus kinase (Jak) 1, 2, or 3 inhibitor. For example, Roluxitinib, Lestaurtinib, Tofacinitinib, INCB-28050, CYT387, GLPG-0634, AZD1480, VX509, R348, TG101348, AC-430, R723, BMS911543, CEP33779 or any other Jak 1, 2, or 3 inhibitor may be excluded from a composition or method of the present invention. Jak 1, 2, and 3 inhibitors may not be suitable for use in certain embodiments of the present subject matter.

In some embodiments, a compound that that preferentially inhibits IL-7 signal transduction or a compound that preferentially inhibits IL-15 signal transduction is administered as a monotherapy. As used herein, "monotherapy" means a therapy that is administered to treat a disease, such as DED, autoimmune uveitis, or GVHD, without any other therapy that is used to treat the disease.

Aspects of the present invention also provide a composition having a compound that preferentially inhibits interleukin-7 (IL-7) signal transduction or a compound that preferentially inhibits interleukin-15 (IL-15) signal transduction in an ophthalmically acceptable vehicle.

Contact lenses are also provided. In various embodiments, contact lenses of the present subject matter comprise a composition comprising a compound that preferentially inhibits interleukin-7 (IL-7) signal transduction and/or a compound that preferentially inhibits interleukin-15 (IL-15) signal transduction, wherein said composition is incorporated into or coated onto the lenses.

Also provided is a device comprising a polymer and a bioactive composition comprising a compound that preferentially inhibits interleukin-7 (IL-7) signal transduction and/or a compound that preferentially inhibits interleukin-15 (IL-15) signal transduction.

Aspects of the present subject matter also provide an eye drop composition having a compound that preferentially inhibits interleukin-7 (IL-7) signal transduction and/or a compound that preferentially inhibits interleukin-15 (IL-15) signal transduction and a pharmaceutically acceptable carrier. In certain embodiments, the eye drop composition is within a dispenser suitable for administering a drop of said composition to an eye of a subject. In some embodiments, the composition has an osmolarity between about 200 to about 400 milliosmoles/kilogram inclusive and a pH from about 6.5 to about 7.5, inclusive.

Aspects of the present invention relate to compositions comprising an antibody that binds to IL-7 or IL-7R so as to inhibit or reduce binding of IL-7 with IL-7R and/or an antibody that binds to IL-15 or IL-15R so as to inhibit or reduce binding of IL-15 with IL-SR. In various embodiments, the antibody is present at a concentration of about 0.01, 0.1, 0.2, 0.3, 0.4, 0.5, 0.75, 1, 1.25, 1.5, 2, 3, 4, 5, 6, 7, 8, 9, 10, 0.01-10, 0.1-2.5, 0.5-2.5, 2.5-5, or 0.5-5 mg/ml. In some embodiments, a dose of an antibody is about 0.5, 1, 5, 7, 8, 9, 10, 15, 20, 25, 30, 35, 40, 45, 50, 55, 60, 65, 70, 75, 80, 85, 90, 95, 100, 0.5-100, 0.5-50, 50-100, 1-10, 1-25, 25-50, or 1-50 µg. Compositions of the present invention may include, e.g., phosphate buffered saline (PBS).

In various implementations of the present subject matter, a symptom of the ocular immunoinflammatory disorder is reduced within about 5, 15, 30, or 60 minutes; or within 1, 2, 3, 4, 5, 6, 7, 8, 9, 10, 11, 12, 13, or 14 days after administration of an inhibitor. In some embodiments, a composition is administered to the eye of the subject, less than 1, 2, 3, 4, 5, or 6 times per day, about 1, 2, 3, 4, 5, 6, or 7 times per week; or once daily. In certain embodiments, the composition is administered by the subject (i.e., self-administration) or by a physician. Aspects of the present subject matter provide methods for treating a subject afflicted with an ocular immunoinflammatory disorder. Such methods include locally administering to an eye of the subject a composition having an effective amount of an inhibitor of an interleukin-7 (IL-7) pathway or an interleukin-15 (IL-15) pathway so as to thereby treat the subject.

In various embodiments, a method comprises administering an inhibitor of the IL-7 pathway which is (i) a compound that reduces binding of IL-7 to an IL-7 receptor (IL-7R); (ii) a compound that reduces IL-7R signaling; (iii) a compound that reduces formation of IL-7R; (iv) a compound that reduces expression of IL-7; and/or (v) a compound that reduces expression of a polypeptide within IL-7R. Alternatively or in addition, a method comprises administering an inhibitor of the IL-15 pathway which is (i) a compound that reduces binding of IL-15 to an IL-15 receptor (IL-15R); (ii) a compound that reduces IL-15R signaling; (iii) a compound that reduces formation of IL-15R; (iv) a compound that reduces expression of IL-15; and/or (v) a compound that reduces expression of a polypeptide within IL-15R.

Various implementations of the subject matter herein relate to the treatment of an ocular immunoinflammatory disorder that is a memory Th17 cell-mediated ocular immunoinflammatory disorder. In certain embodiments, the Th17 cell-mediated ocular immunoinflammatory disorder is dry eye disease (DED).

The IL-7 pathway may be inhibited using many types of inhibitors. In certain embodiments, (i) the compound that reduces binding of IL-7 to IL-7R; (ii) the compound that reduces IL-7R signaling; (iii) the compound that reduces formation of IL-7R; (iv) the compound that reduces expression of IL-7; and/or (v) the compound that reduces expression of a polypeptide within IL-7R, is a small molecule, an antibody, an antibody fragment, a polypeptide, a DNA aptamer, an RNA aptamer, or an oligonucleotide. Non-limiting examples of oligonucleotides include ribozymes, antisense oligonucleotides, morpholinos, and RNA interference (RNAi) molecules.

The IL-15 pathway may also be inhibited using a many types of inhibitors. In various embodiments, (i) the compound that reduces binding of IL-15 to IL-15R; (ii) the compound that reduces IL-15R signaling; (iii) the compound that reduces formation of IL-15R; (iv) the compound that reduces expression of IL-15; and/or (v) the compound that reduces expression of a polypeptide within IL-15R, is a small molecule, an antibody, an antibody fragment, a polypeptide, a DNA aptamer, an RNA aptamer, or an oligonucleotide. As with IL-7 pathway inhibitors, on-limiting examples of oligonucleotides include ribozymes, antisense oligonucleotides, morpholinos, and RNA interference (RNAi) molecules.

Compositions and methods of the present subject matter are effective to treat subjects afflicted with a variety of symptoms. In some embodiments, the subject suffers from a sandy or gritty feeling as if something is in the eye, eye dryness, heavy eyelids, stinging, itching, burning, irritation, pain, redness, inflammation, discharge, inability to cry when emotionally stressed, eye fatigue, blurred vision, or excessive watering, and wherein said method inhibits or reduces the severity of the sandy or gritty feeling as if something is in the eye, eye dryness, heavy eyelids, stinging, itching, burning, irritation, pain, redness, inflammation, discharge, inability to cry when emotionally stressed, eye fatigue, blurred vision, or excessive watering.

In certain embodiments, a composition of the present subject matter is in the form of a solid, an ointment, a gel, a liquid, an aerosol, a mist, a polymer, a contact lens, a film, an emulsion, or a suspension. In some embodiments, the composition is administered topically. For example, some implementations do not include the systemic administration or substantial dissemination to non-ocular tissue of the composition.

In various embodiments, the number or activity of Th17 cells is altered after a composition is administered. For example, the number of memory Th17 cells in the eye of the subject is reduced after the composition is administered.

In some embodiments, the composition further comprises an inhibitor of an IL-17 pathway. Non-limiting examples of IL-17 pathway inhibitors are described in U.S. Patent Application Publication No. US20110104236 A1, published May 5, 2011, the entire content of which is incorporated herein by reference. For example, the IL-17 pathway inhibitor may block or reduce binding of IL-17 to an IL-17 receptor. In various embodiments, the IL-17 inhibitor is a small molecule, an antibody, an antibody fragment, a polypeptide, a DNA aptamer, an RNA aptamer, or an oligonucleotide.

Various implementations of the present subject matter relate to inhibitors that specifically target the IL-7 pathway or the IL-15 pathway. For example, an inhibitor of the IL-7 pathway may bind IL-7 or IL-7R with at least 5, 10, 15, 20, 25, 30, 35, 40, 45, 50, 55, 60, 75, 80, 85, 90, 95, 100% or 2-fold, 5-fold, 10-fold, 100-fold, or 1000-fold higher affinity than IL-1, IL-2, IL-3, IL-4, IL-5, IL-6, IL-8, IL-10, IL-11, IL-12, IL-13, IL-14, IL-15, IL-16, IL-17, IL-18, IL-19, IL-20, IL-21, IL-22, IL-23, IL-24, IL, 25, IL-26, IL-27, IL-28, IL-29, IL-30, IL-31, IL-32, IL-33, IL-34, IL-35, IL-36, IL-37, IL-38 and/or, interferon gamma (IFN-γ), or a receptor thereof. Additionally, an inhibitor of the IL-15 pathway may bind IL-15 or IL-15 with at least 5, 10, 15, 20, 25, 30, 35, 40, 45, 50, 55, 60, 75, 80, 85, 90, 95, 100% or 2-fold, 5-fold, 10-fold, 100-fold, or 1000-fold higher affinity than IL-1, IL-2, IL-3, IL-4, IL-5, IL-6, IL-7, IL-8, IL-10, IL-11, IL-12, IL-13, IL-14, IL-16, IL-17, IL-18, IL-19, IL-20, IL-21, IL-22, IL-23, IL-24, IL, 25, IL-26, IL-27, IL-28, IL-29, IL-30, IL-31, IL-32, IL-33, IL-34, IL-35, IL-36, IL-37, IL-38 and/or, interferon gamma (IFN-γ), or a receptor thereof.

Aspects of the present invention also provide contact lens comprising a composition comprising an effective amount of an inhibitor of an interleukin-7 (IL-7) pathway or an interleukin-15 (IL-15) pathway, wherein said composition is incorporated into or coated onto said lens. Devices including a polymer and a bioactive composition having an effective amount of an inhibitor of an interleukin-7 (IL-7) pathway or an interleukin-15 (IL-15) pathway are also provided. In various embodiments, the device is for incorporation into or onto an ocular tissue. For example, the device may be in contact with an ocular tissue. Also provided are devices comprising a polymer and a bioactive composition having an effective amount of an inhibitor of an interleukin-7 (IL-7) pathway or an interleukin-15 (IL-15) pathway. In certain embodiments, such devices are implanted or injected into an ocular tissue or fluid cavity. Aspects of the present invention further provide compositions with an effective amount of an inhibitor of an interleukin-7 (IL-7) pathway or an interleukin-15 (IL-15) pathway in an ophthalmically acceptable vehicle.

Various embodiments of the present subject matter provide an eye drop composition having an effective amount of an inhibitor of an interleukin-7 (IL-7) pathway or an interleukin-15 (IL-15) pathway and a pharmaceutically acceptable carrier. Preferably, such a composition is within a dispenser suitable for administering a drop of said composition to an eye of a subject. In some embodiments, the composition has an osmolarity between about 200 to about 400 milliosmoles/kilogram inclusive and a pH from about 6.5 to about 7.5 inclusive.

In certain embodiments, a composition of the present subject matter may comprise a neutralizing or function-blocking antibody against IL-7 and/or IL-15 and/or against IL-7R formation and/or IL-15R formation. The neutralizing or function-blocking antibody may be a reformulated or humanized derivative of or bind to the epitope of an affinity-purified polyclonal antibody.

Exemplary methods for inhibiting or reducing the severity of an ocular immunoinflammatory disease may be carried out by locally administering to an eye of a subject a composition comprising a polynucleotide, a polypeptide, an antibody, a compound, or a small molecule that inhibits or modifies the transcription, transcript stability, translation, modification, localization, secretion, or function of a polynucleotide or polypeptide encoding IL-7 or IL-15 or any component of IL-7R or IL-15R.

In certain embodiments, the composition may comprise an intrabody that binds to IL-7R or IL-15R or any synthetic intermediate or subunit of IL-7, IL-7R, IL-15, or IL-15R. The composition may alternatively, or in addition, comprise a soluble fragment of IL-7R which binds IL-7 and/or a soluble fragment of IL-15R which binds IL-15.

Exemplary polypeptides include, but are not limited to, fusion and/or chimeric proteins capable of disrupting IL-7 or IL-15 function.

In various embodiments, a composition comprises a ribozyme, an antisense oligonucleotide (such as a morpholino), a microRNA (miRNA), a short hairpin RNA (shRNA), or a short interfering RNA (siRNA) to reduce or silence gene expression.

In some embodiments, function-blocking antibodies targeted against IL-7, IL-15, IL-7R and/or IL-15R are monoclonal or polyclonal. Antibodies include those that bind to one or more sequences within an IL-7, IL-15, IL-7 receptor polypeptide, or IL-15 receptor polypeptide. In certain embodiments, the antibody is an intrabody. In some embodiments, the antibody comprises a single chain, a humanized, a recombinant, or a chimeric antibody.

In various implementations of the present subject matter, inhibitors of IL-7, IL-15, IL-7R and/or IL-15R are administered either simultaneously or sequentially with a secondary composition comprising one or more of the following: an antibiotic, an immunosuppressive composition, an anti-inflammatory composition, a growth factor, a steroid, a chemokine, or a chemokine receptor.

A small molecule is a compound that is less than 2000 daltons in mass. The molecular mass of the small molecule is preferably less than 1000 daltons, more preferably less than 600 daltons, e.g., the compound is less than 500 daltons, 400 daltons, 300 daltons, 200 daltons, or 100 daltons. Small molecules may be, e.g., organic or inorganic. Exemplary organic small molecules include, but are not limited to, aliphatic hydrocarbons, alcohols, aldehydes, ketones, organic acids, esters, mono- and disaccharides, aromatic hydrocarbons, amino acids, and lipids. Exemplary inorganic small molecules comprise trace minerals, ions, free radicals, and metabolites. Alternatively, small molecule inhibitors can be synthetically engineered to consist of a fragment, or small portion, or a longer amino acid chain to fill a binding pocket of an enzyme. Typically small molecules are less than one kilodalton.

In certain embodiments, the composition comprises one or more antibiotic compositions to be used in combination with an inhibitor of IL-7 or IL-15 function. The antibiotic and IL-7 or IL-15 inhibitor compositions are administered simultaneously or sequentially. Exemplary antibiotic compositions used for combination-therapy with inhibitors of IL-7 or IL-15 function include but are not limited to, amikacin, gentamicin, kanamycin, neomycin, netilmicin, streptomycin, tobramycin, teicoplanin, vancomycin, azithromycin, clarithromycin, clarithromycin, dirithromycin, erythromycin, roxithromycin, troleandomycin, amoxicillin, ampicillin, azlocillin, carbenicillin, clozacillin, dicloxacillin, flucozacillin, mezlocillin, nafcillin, penicillin, piperacillin, ticarcillin, bacitracin, colistin, polymyxin B, ciprofloxacin, enoxacin, gatifloxacin, levofloxacin, lomefloxacin, moxifloxacin, norfloxacin, oflazacin, trovafloxacin, mafenide, sulfacetamide, sulfamethizole, sulfasalazine, sulfisoxazole, tetracycline, trimethoprim, cotrimoxazole, demeclocycline, soxycycline, minocycline, doxycycline, oxytetracycline, or tetracycline.

In some embodiments, the composition comprises an inhibitor of IL-7, IL-15, IL-7R, and/or IL-15R, administered simultaneously or sequentially with a second immunosuppressive composition. The composition comprising an IL-7, IL-15, IL-7R, and/or IL-15R inhibitor may be administered, e.g., topically or intraocularly. The second immunosuppressive composition may be administered topically, intraocularly, or systemically. In various embodiments, the immunosuppressive compound may comprise cyclosporin A or an analog thereof a concentration of 0.05-4.0% (mg/ml). Alternatively, or in addition, the immunosuppressive composition may comprise a glucocorticoid, a cytostatic agent, an alkylating agent (nitrogen mustards/cyclophosphamide, nitrosoureas, platinum compounds), an antimetabolic agent (methotrexate, any folic acid analog, azathioprine, mercaptopurine, any purine analog, any pyrimidine analog, any inhibitor of protein synthesis), a cytotoxic antibiotic (dactinomycin, an anthracycline, mitomycin C, bleomycin, mithramycin), a polyclonal antibody (Atgam®, Thympglobuline®, any antibody against the antilymphocyte or antithymocyte antigens), a monoclonal antibody (OKT3®, any antibody against the T-cell receptor, any antibody against IL-2, basiliximab/Simulect®, declizumab/Zenapax®), Tacrolimus/Prograf™/FK506, Sirolimus/Rapamune™/Rapamycin, interferon beta, interferon gamma, an opioid, a TNFα binding protein, mycophenolate, or FTY720.

In various embodiments, compositions of the present subject matter comprise a polynucleotide, an aptamer, a polypeptide, an antibody or a fragment thereof, or a small molecule that binds or modifies the function of IL-7, IL-15, IL-7R, or IL-15R administered topically with a pharmaceutically appropriate carrier. Delivery methods for polynucleotide compositions include, but are not limited to, liposomes, receptor-mediated delivery systems, naked DNA, and engineered viral vectors such as herpes viruses, retroviruses, adenoviruses and adeno-associated viruses, among others. Polynucleotide compositions may be administered topically with a pharmaceutically acceptable liquid carrier, e.g., a liquid carrier, which is aqueous or partly aqueous. In certain embodiments, polynucleotide sequences within the composition are associated with a liposome (e.g., a cationic or anionic liposome).

A number of methods have been developed for delivering short DNA or RNA sequences into cells; e.g., polynucleotide molecules can be contacted directly onto the tissue site, or modified polynucleotide molecules, designed to specifically target desired cell types (e.g., sequences linked to peptides or antibodies that specifically bind receptors or antigens expressed on the target cell surface).

An exemplary approach uses a recombinant DNA construct in which the short polynucleotide sequence is placed under the control of a strong polymerase III or polymerase II promoter. The use of such a construct will result in the transcription of sufficient amounts of polynucleotide that will form complementary base pairs with the endogenous transcripts of nucleic acids of the invention and thereby prevent translation of endogenous mRNA transcripts. The invention encompasses the construction of a short polynucleotide using the complementary strand as a template. For example, a vector can be introduced in vivo such that it is taken up by a cell and directs the transcription of an interfering RNA or precursor to a double stranded RNA molecule. Alternatively, the template for the short polynucleotide transcript is placed under the transcriptional control of a cell-type specific promoter or other regulatory element. Thus, diffusion or absorption of a topically administered composition beyond the intended ocular target tissue does not cause deleterious or systemic side effects. The vector remains episomal or becomes chromosomally integrated, as long as it can be transcribed to produce the desired polynucleotide.

Expression vectors are constructed by recombinant DNA technology methods standard in the art. Vectors can be plasmid, viral, or others known in the art, used for replication and expression in mammalian cells. Expression of the sequence encoding the short polynucleotide can be placed under the control of any promoter known in the art to act in mammalian, preferably human cells. Promoters are inducible or constitutive. Exemplary promoters include, but are not limited to: the SV40 early promoter region (Bernoist et al., Nature 290:304, 1981); the promoter contained in the 3' long terminal repeat of Rous sarcoma virus (Yamamoto et al., Cell, 22:787-797, 1988); the herpes thymidine kinase promoter (Wagner et al., Proc. Natl. Acad. Sci. USA, 78:1441, 1981); or the regulatory sequences of the metallothionein gene (Brinster et al., Nature, 296:39, 1988).

In some embodiments, polypeptide compositions are associated with liposomes alone or in combination with receptor-mediated delivery systems, to enable transport across the plasma membrane. Polypeptide compositions may be, e.g., soluble or membrane-bound. An exemplary receptor-mediated delivery system involves fusion of a low-density or very-low-density lipoprotein containing particle or vesicle to the low-density lipoprotein (LDL) receptor (LDLR) as observed with Hepatitis C Virus (HCV) infection and HCV-mediated drug delivery methods.

Various implementations of the present subject matter include a composition having one or more extracellular or intracellular antibodies (also called intrabodies) raised or directed against IL-7, IL-15, IL-7R (or a subunit thereof), or IL-15R (or a subunit thereof). Extracellular antibodies are topically administered with a pharmacologically appropriate aqueous or non-aqueous carrier. Sequences encoding intracellular antibodies are subcloned into a viral or mammalian expression vector, packed in a lipophilic device to facilitate transport across the plasma membrane, and topically administered to eye tissue with a pharmacologically appropriate aqueous or non-aqueous carrier. Once inside the plasma membrane, host cell machinery transcribes, translates, and processes the intrabody code to generate an intracellular function-blocking antibody targeted against IL-7, IL-15, IL-7R (or a subunit thereof), or IL-15R (or a subunit thereof). In the case of secreted molecules, intracellular antibodies prevent post-translational modification or secretion of the target protein. In the case of membrane-bound molecules, intracellular antibodies may also prevent intracellular signaling events upon receptor engagement or binding by IL-7 or IL-15.

In some embodiments, a composition of the present subject matter comprises an inhibitor of IL-7, IL-15, IL-7R, and/or IL-15R in combination with other inhibitory elements. Inhibitors of IL-7, IL-15, IL-7R, and/or IL-15R and other inhibitory elements may be administered simultaneously or sequentially. In one embodiment, the composition comprises an inhibitor of IL-7, IL-15, IL-7R and/or IL-15R function and an inhibitor of tumor necrosis factor alpha (TNFα). Exemplary functional blockers of TNFα include, but are not limited to, recombinant and/or soluble TNFα receptors, monoclonal antibodies, and small molecule inhibitors and/or inverse agonists. One or more commercially-available TNF-α blocking agents are reformulated for topical administration in certain embodiments. Exemplary commercial TNF-α blocking agents used for reformulation include, but are not limited to, etanerept/Embrel, infliximab/Remicade, and adalimumab/Humira. Alternatively or in addition, the composition comprises an inhibitor of IL-7, IL-15, IL-7R, and/or IL-15R and inhibitor(s) of one or more interleukin cytokines. Exemplary cytokines include, but are not limited to, IL-1, IL-2, IL-4, IL-5, IL-6, IL-8, IL-12, IL-18, and IL-23. In various embodiments, the composition comprises an inhibitor of IL-7, IL-15, IL-7R, and/or IL-15R and an inhibitor of interferon-gamma. In some embodiments, the composition comprises an inhibitor of IL-7, IL-15, IL-7R, and/or IL-15 SR and inhibitor(s) of one or more chemokines and their receptors. Exemplary chemokines and receptors comprised by the composition of this embodiment include, but are not limited to, chemokine (C-C motif) receptor 1 (CCR1), chemokine (C-C motif) receptor 2 (CCR2), chemokine (C-C motif) receptor 5 (CCR5), chemokine (C-C motif) receptor 7 (CCR7), and chemokine (C-X-C motif) receptor 3 (CXCR3).

In some embodiments wherein the composition comprises an inhibitor of IL-7, IL-15, IL-7R, and/or IL-15R and a second composition, the respective doses of the inhibitor to the second composition is a ratio between 1:10 and 10:1 (mass/weight). Alternatively, the ratio is 1:9, 1:8, 1:7, 1:6, 1:5, 1:4, 1:3, 1:2, 1:1, 2:1, 3:1, 4:1, 5:1, 6:1, 7:1, 8:1, or 9:1.

Aspects of the present subject matter also relate to a contact lens device consisting of a composition that inhibits an activity of IL-7, IL-15, IL-7R, and/or IL-15R and a pharmaceutically compatible polymer. In certain embodiments, a composition also comprises a combination of inhibitors of IL-7, IL-15, IL-7R and/or IL-15R function as well as secondary compositions. For example, the composition is incorporated into or coated onto said lens. The composition is either chemically bound or physically entrapped by the contact lens polymer. The contact lens may be, e.g., either hydrophobic or hydrophilic.

The present subject matter also provides a drug-delivery device consisting of a composition that inhibits an activity of IL-7, IL-15, IL-7R and/or IL-15R and a pharmaceutically compatible polymer. In various embodiments, this composition also comprises a combination of inhibitors of IL-7, IL-15, IL-7R and/or IL-15R function as well as secondary compositions. For example, the composition is incorporated into or coated onto said polymer. The composition is either chemically bound or physically entrapped by the polymer. The polymer is either, e.g., hydrophobic or hydrophilic. The polymer device may comprise multiple physical arrangements. Exemplary physical forms of the polymer device include, but are not limited to, a film, a scaffold, a chamber, a sphere, a microsphere, a stent, or other structure. The polymer device may have, e.g., internal and external surfaces. In some embodiments, the device has one or more internal chambers. These chambers may contain one or more compositions. In certain embodiments, the device contains polymers of one or more chemically-differentiable monomers. The subunits or monomers of the device polymerize in vitro or in vivo.

Various implementations of the present subject matter comprise a device comprising a polymer and a bioactive composition incorporated into or onto said polymer, wherein said bioactive composition inhibits an activity of IL-7, IL-15, IL-7R and/or IL-15R, and wherein said device is implanted or injected into an ocular surface tissue, an adnexal tissue in contact with an ocular surface tissue, a fluid-filled ocular or adnexal cavity, or an ocular or adnexal cavity.

Exemplary mucoadhesive polyanionic natural or semi-synthetic polymers from which the device is formed include, but are not limited to, polygalacturonic acid, hyaluronic acid, carboxymethylamylose, carboxymethylchitin, chondroitin sulfate, heparin sulfate, and mesoglycan. In various embodiments, the device comprises a biocompatible polymer matrix that may optionally be biodegradable in whole or in part. A hydrogel is one example of a suitable polymer matrix material. Examples of materials which can form hydrogels include polylactic acid, polyglycolic acid, PLGA polymers, alginates and alginate derivatives, gelatin, collagen, agarose, natural and synthetic polysaccharides, polyamino acids such as polypeptides particularly poly (lysine), polyesters such as polyhydroxybutyrate and poly-.epsilon.-caprolactone, polyanhydrides; polyphosphazines, poly(vinyl alcohols), poly(alkylene oxides) particularly poly (ethylene oxides), poly(allylamines)(PAM), poly(acrylates), modified styrene polymers such as poly(4-aminomethylstyrene), pluronic polyols, polyoxamers, poly(uronic acids), poly(vinylpyrrolidone) and copolymers of the above, including graft copolymers. In certain embodiments, the scaffolds may be fabricated from a variety of synthetic polymers and naturally-occurring polymers such as, but not limited to, collagen, fibrin, hyaluronic acid, agarose, and laminin-rich gels.

One exemplary material for the hydrogel is alginate or modified alginate material. Alginate molecules are comprised of (1-4)-linked 3-D-mannuronic acid (M units) and α L-guluronic acid (G units) monomers which vary in proportion and sequential distribution along the polymer chain. Alginate polysaccharides are polyelectrolyte systems which have a strong affinity for divalent cations (e.g. $Ca^{+2}$, $Mg^{+2}$, $Ba^{+2}$) and form stable hydrogels when exposed to these molecules. See Martinsen A., et al., Biotech. & Bioeng., 33 (1989) 79-89.

Certain embodiments of the present subject matter utilize an alginate or other polysaccharide of a lower molecular weight, preferably of size which, after dissolution, is at the renal threshold for clearance by humans. Polymeric devices are located topically or subcutaneously, though very superficially, wherein either a composition chemically bound or physically entrapped by the polymeric device or the device itself, degrades and must be cleared from the body. For a biodegradable polymeric device, it is preferred that the alginate or polysaccharide is reduced to a molecular weight of 1000 to 80,000 daltons, more preferably 1000 to 60,000 daltons, particularly preferably 1000 to 50,000 daltons. It is also useful to use an alginate material of high guluronate content since the guluronate units, as opposed to the mannuronate units, provide sites for ionic crosslinking through divalent cations to gel the polymer.

Internal and external surfaces optionally contain pores. Pores are either created prior to administration into a subject or result from the inclusion of pore-forming agents within the device that perforate surfaces upon administration to a subject. Exemplary pore forming agents include, but are not limited to, water soluble compounds such as inorganic salts and sugars.

In various embodiments, a device of the present subject matter is administered topically, subconjunctively, or in the episcleral space, subcutaneously, or intraductally. In some embodiments, the device is placed on or just below the surface if an ocular tissue. In certain embodiments, the device is placed inside a tear duct or gland. In some implementations relating to polymers, the composition incorporated into or onto the polymer is released or diffuses from the device.

Aspects of the present subject matter relate to compositions with variable physical and chemical forms; however, in various embodiments the compositions are topically administered and contact an eye directly. The composition may be administered, e.g., as a solid, a paste, an ointment, a gel, a liquid, an aerosol, a mist, a polymer, a film, an emulsion, or a suspension. Furthermore, the composition may be incorporated into or coated onto a contact lens or drug delivery device, from which one or more molecules diffuse away from the lens or device or are released in a temporally-controlled manner. In such embodiments, the contact lens composition either remains on the ocular surface (e.g. if the lens is required for vision correction) or the contact lens dissolves as a function of time simultaneously releasing the composition into closely juxtaposed tissues. Similarly, the drug delivery device is optionally biodegradable or permanent in various embodiments.

In some embodiments, the invention comprises a composition with means to inhibit the transcription, transcript stability, translation, modification, localization, secretion, or receptor binding of IL-7 and/or IL-15. In certain embodiments, the composition is capable of binding to one or more regions of an 11-7 or IL-15 mRNA transcript or a IL-7 or IL-15 polypeptide.

In various embodiments, the composition comprises an inhibitor or inverse agonist of a receptor for IL-7. IL-7R is a heterodimer comprising interleukin-7 receptor-α (CD127) and common-γ chain receptor (CD132). In some embodiments an inhibitor is defined as a binding partner, or ligand, of an IL-7R that inhibits the function of an agonist, IL-7, or inverse agonist by blocking its binding to the receptor. An inverse agonist of a receptor for IL-7 is a molecule which binds to the same IL-7R binding-site as an agonist, for instance, IL-7, but exerts the opposite pharmacological effect. In some embodiments, the composition comprises a polynucleotide, a polypeptide, an antibody, a compound, or a small molecule that binds to a region of an IL-7R mRNA or polypeptide.

In certain embodiments, the composition comprises an inhibitor or inverse agonist of a receptor for IL-15. IL-15R is a heterotrimer comprising IL-15R alpha, IL-2/IL-15 receptor beta chain (CD122), and common-γ chain receptor (CD132). In some embodiments an inhibitor is defined as a binding partner, or ligand, of an IL-15R that inhibits the function of an agonist, IL-15, or inverse agonist by blocking its binding to the receptor. An inverse agonist of a receptor for IL-15 is a molecule which binds to the same IL-15R binding-site as an agonist, for instance, IL-15, but exerts the opposite pharmacological effect. In some embodiments, the composition comprises a polynucleotide, a polypeptide, an antibody, a compound, or a small molecule that binds to a region of an IL-15R mRNA or polypeptide.

Aspects of the present subject matter provide a method of reducing Th17 cell abundance in an ocular, adnexal, or lymph tissue of a subject in need thereof including administering to the subject a composition that inhibits an activity of 11-7, IL-15, IL-7R, and/or IL-15R.

Various embodiments relate to a method for treating an ocular immunoinflammatory disorder comprising inhibiting the survival or proliferation of a Th17 cell in an eye tissue, wherein the survival or proliferation is inhibited by administering to a subject an inhibitor of IL-15 or IL-7. In non-limiting examples, immunoinflammatory disorder comprises DED, autoimmune uveitis, or ocular graft versus host disease. In some embodiments, the method comprises topically administering a compound that preferentially inhibits IL-15 signal transduction or a compound that preferentially inhibits IL-7 signal transduction to the surface of the eye of a human subject.

Included herein are compositions comprising an inhibitor of IL-15 or IL-7 for use in treating an ocular immunoinflammatory disorder (e.g., DED, autoimmune uveitis, or ocular graft versus host disease). In some embodiments, treating the ocular immunoinflammatory disorder comprises inhibiting the survival or proliferation of a Th17 cell in an eye tissue. In some embodiments, the inhibitor of IL-15 comprises a compound that preferentially inhibits IL-15 signal transduction. In some embodiments, the inhibitor of IL-7 comprises a compound that preferentially inhibits IL-7 signal transduction.

Each embodiment disclosed herein is contemplated as being applicable to each of the other disclosed embodiments. Thus, all combinations of the various elements described herein are within the scope of the invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

DESCRIPTION OF THE DRAWINGS

(FIG. 1A) Increased expression of IL-7 and IL-15 in both draining lymph nodes (DLN) and conjunctiva was observed in chronic DED (DED D28). mRNA expression levels have been normalized to naive mice (NL). (FIG. 1B) Constitutively high protein expression of IL-7 and IL-15 in DLN, and increased both proteins in conjunctiva were observed in chronic DED. (FIG. 1C) Up-regulation of both IL-7 and IL-15 receptors (IL-7R and IL-15R) on memory Th17 cells (mTh17) was observed in chronic DED, as compared to effector Th17 cells (eTh17). MFI: mean fluorescein intensity. *, $p<0.05$.

(FIG. 4A) In the absence of an inhibitor, IL-7 and IL-15 can bind their respective receptors (IL-7R and IL-15R, respectively), which leads to signal transduction. (FIG. 4B) In various embodiments, an inhibitor that binds IL-7 or IL-15 blocks receptor binding. (FIG. 4C) In certain embodiments, an inhibitor that binds IL-7R or IL-15R blocks receptor binding.

(FIG. 5B) At the end of the treatment, ocular surface memory Th17 cells were almost completely depleted by either anti-IL-7 or anti-IL-15 treatment.

DETAILED DESCRIPTION

Figure 1A:
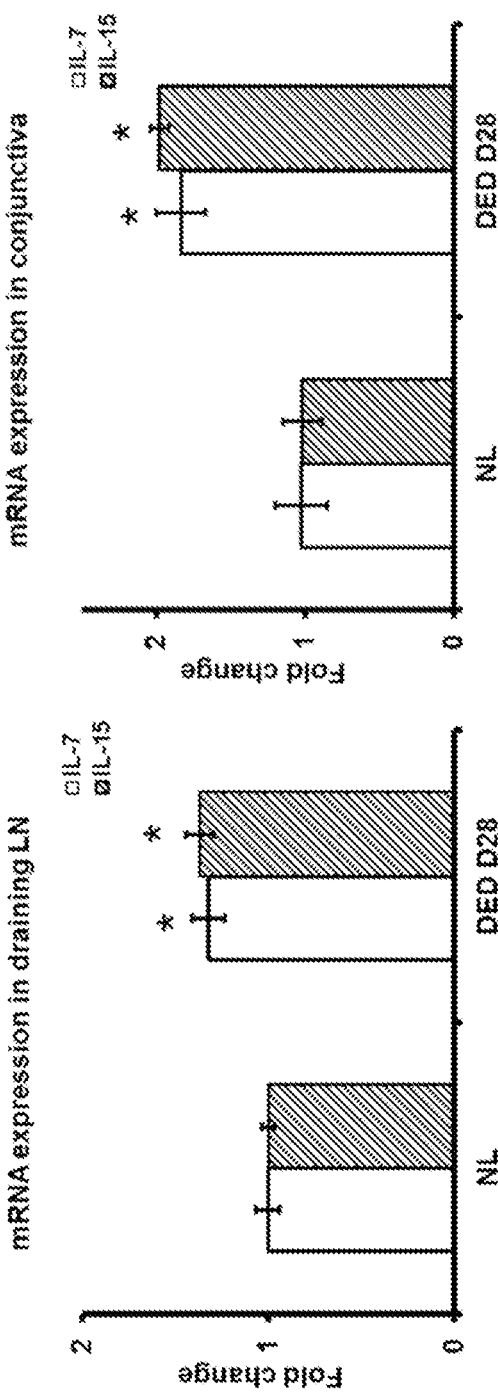
FIGS. 1A-1C are a graphs showing increased expression of IL-7 and IL-15 as well as their respective receptors on memory Th17 cells in chronic DED mice.

The subject matter described herein provides novel methods for the treatment of memory Th17 cell-mediated ocular disorders including DED, autoimmune uveitis, and ocular GVHD, comprising ocular delivery (e.g. topical, subconjunctival, or intravitreal administration) of an IL-7/IL-7R and/or an IL-15/IL-15R signaling inhibitor into the eye in combination with a pharmaceutically acceptable carrier. This is a novel and fundamentally different approach to the treatment of ocular immunoinflammatory diseases (e.g., DED, autoimmune uveitis, and ocular GVHD), compared to current nonspecific approaches. Current approaches for treating ocular immunoinflammatory diseases such as DED are reliant on the use of nonspecific anti-inflammatory agents, such as corticosteroids, that are fraught with side-effects.

Without wishing to be bound by any scientific theory, the persistent ocular surface inflammation in DED is mediated by memory T helper 17 (Th17) cells and immunological memory has a central role in maintaining chronic ocular disease (Mucosal Immunol 2014; 7:38-45). Very little is known about the factors that regulate long-term maintenance of memory Th17 cells. Aspects of the present subject matter relate to the surprising discovery that inhibitors of the IL-7 and IL-15 pathways are useful for treating ocular immunoinflammatory diseases such as DED.

Non-limiting examples of IL-7/IL-7R or IL-15/IL-15R signaling inhibitors include agents that prevent or reduce IL-7R or IL-15R mediated signal transduction. For example, IL-7R mediated signal transduction may be prevented or reduced by inhibiting the binding of IL-7 to IL-7R. Likewise, IL-15R mediated signal transduction may be reduced or prevented by inhibiting the binding of IL-15 to IL-15R. Such agents may comprise, but are not restricted to, the following: neutralizing anti-IL-7R antibodies and fragments thereof; anti-IL-15R antibodies and fragments thereof; small molecular inhibitors of IL-7R or IL-15R; proteins such as anti-IL-7 and anti-IL-15 fusion proteins (such as a soluble version or fragment of IL-7R or IL-15R); anti-IL-7 antibodies and fragments thereof; anti-IL-15 antibodies and fragments thereof; and aptamers (e.g., DNA or RNA aptamers) that bind to IL-7, IL-7R, IL-15, or IL-15R. In various embodiments, combinations of one, two, three, four or more of these agents are administered.

Non-limiting examples of inhibitors useful in various embodiments of the present subject matter include: Human IL-7 monoclonal antibody (Clone #MAB207, R&D Systems (Minneapolis, Minn., USA)); Human IL-7 polyclonal antibody (Clone #AF-207, R&D Systems); Human IL-7R alpha (CD127) antibody (Clone #MAB306, R&D Systems); Anti-human CD127 (Clone #eBioRDRS, eBiosceience (San Diego, Calif., USA)); Soluble human IL-7R alpha (CD127)-Fc chimera (Cat #306-IR, R&D Systems); Human IL-15 monoclonal antibody (Clone #MAB247, R&D Systems); Human IL-15 monoclonal antibody (Clone #MAB647, R&D Systems); Human IL-15R alpha antibody (Clone #AF247, R&D Systems); Anti-human IL-15 (Clone #ct2nu, eBiosceience); Anti-human CD215 (IL-15R alpha) (Clone #eBioJM7A4, eBiosceience); and Soluble human IL-15R alpha-Fc chimera (Cat #147-IR, R&D Systems).

In various embodiments, the inhibitor is an extracellular portion of an IL-7R or IL-15R protein subunit. In some embodiments, the extracellular portion is fused to an antibody or a fragment thereof. For example, the extracellular portion may be fused to the Fc domain of an antibody (e.g., human IgG$_1$). The fusion may be direct or via, e.g., a polypeptide linker such as IIEGRMD (SEQ ID NO: 37) or IEGRDMD (SEQ ID NO: 38).

A non-limiting example of a soluble human IL-7R alpha (CD127)-Fc chimera is available from R&D Systems (Minneapolis, Minn., USA) (Cat #306-IR).

Source: Mouse myeloma cell line, NS0-derived

| Human IL-7 R alpha (Glu21-Lys261) Accession # P16871.3 N-terminus | IIEGRMD | Human IgG$_1$ (Pro100-Lys330) C-terminus |
|---|---|---|

UniProt Accession #: P16871.3 (SEQ ID NO: 10)
N-terminal Sequence Analysis: Glu21
Predicted Molecular Mass: (monomer) kDa
SDS-PAGE: 80-90 kDa, reducing conditions A non-limiting example of a soluble human IL-15R alpha-Fc chimera is available from R&D Systems (Minneapolis, Minn., USA) (Cat #147-IR).

Source: *Spodoptera frugiperda*, Sf21 baculovirus)-derived

| Human IL-15 R alpha (Ile31-Thr172) Accession # EAW86418 N-terminus | IEGRDMD | Human IgG$_1$ (Pro100-Lys330) | 6-His tag C-terminus |
|---|---|---|---|

GenBank Accession #: EAW86418 (SEQ ID NO: 35)
N-terminal Sequence Analysis: Ile31
Predicted Molecular Mass: 42.6 (monomer) kDa
SDS-PAGE: 60-70 kDa, reducing conditions Without wishing to be bound by any scientific theory, methods and compositions herein relieve one or more symptoms of a chronic ocular inflammatory disease (e.g., DED) by suppressing the memory Th17 response in chronic ocular immunoinflammatory diseases.

Ocular Immunoinflammatory Diseases

DED is one of the most frequently encountered ocular morbidities and may also be referred to as Dry Eye Syndrome. Twenty-five percent of patients who visit ophthalmic clinics report symptoms of dry eye, making it a growing public health problem and one of the most common conditions seen by eye care practitioners. DED is a highly prevalent condition, estimated to affect 10-20% of the adult population (Ocul Surf 2007; 5:75-92). The disease is seen with increased prevalence in patients with autoimmune diseases, which affect approximately 8% of the population. At present, non-specific anti-inflammatory therapies are the mainstay of treatment for moderate to severe DED, along with topical cyclosporine (the only FDA approved drug for the treatment of DED).

DED is a predominant ocular immunoinflammatory disease. However, other diseases may be treated using methods and compositions provided herein. Exemplary contemplated ocular surface inflammatory diseases include, but are not limited to, penetrating keratoplasty (corneal transplantation), corneal neovascularization, allergy, conjunctivitis, and microbial keratitis. Contemplated disorders can be caused by autoimmune mechanisms, bone marrow transplant, surgery (general eye surgery, corneal transplantation, refractive surgery, LASIK), allergy, infection, trauma, injury, drug use, tear film abnormalities, contact lens use, neovascularization, tumor formation or growth, exposure to airborne or liquid irritants, hormonal variation, deprivation of essential fatty acids, and genetic predisposition.

In various embodiments, a subject who is afflicted with or suffering from an ocular immunoinflammatory disease may be treated using a method or composition of the invention. In certain embodiments, a subject who is "afflicted with" is "suffering from" or is "in need" of treatment for a disease may be a subject who has been affirmatively diagnosed to have that disease. In some embodiments, a subject who is in need of preventative or prophylactic treatment for a disease is a subject who is at risk of developing that disease. In some embodiments, the subject has not been diagnosed with the disease, but has one or more symptoms of the disease.

As used herein, a "symptom" associated with a disease includes any clinical or laboratory manifestation associated with the disease, and is not limited to what the subject can feel or observe. Non-limiting examples of DED symptoms include pain (such as stinging or burning of the eye); ulcers or scars on the cornea; decrease tolerance for dry environments; reduced vision; a sandy or gritty feeling as if something is in the eye; episodes of excess tears following very dry eye periods; a stringy discharge from the eye; redness of the eye; episodes of blurred vision; heavy eyelids; inability to cry when emotionally stressed; uncomfortable contact lenses: decreased tolerance of reading, working on the computer, or any activity that requires sustained visual attention; and eye fatigue. Non-limiting examples of autoimmune uveitis symptoms include redness of the eye; blurred vision; photophobia; sensitivity to light; irregular pupil; eye pain; floaters, which are dark spots that appear to float in the visual field; headaches; dilated ciliary vessels; presence of cells and flare in the anterior chamber; keratic precipitates ("KP") on the posterior surface of the cornea; a hypopyon; pigment deposits on the lens; a festooned pupil on dilation of pupil; busacca nodules (inflammatory nodules located on the surface of the iris); and synechia Photopsia or seeing flashing lights. Non-limiting examples of ocular GV-HD symptoms include blurry vision; foreign body sensation; burning sensation; severe light sensitivity; chronic conjunctivitis (pink eye); dry eyes; and eye pain. In embodiments, the method described herein may include identifying a subject having one or more of these symptoms.

"Treating" (or treatment of) a disease or condition includes ameliorating at least one symptom of the particular disease or condition, even if the underlying pathophysiology is not affected. The efficacy of the treatment can be evaluated, e.g., as compared to a standard, e.g., improvement in the value or quality of a parameter (e.g., self-reported pain level, tolerance for dry environments, numbers of ulcers or scars on the cornea, and vision quality) as compared to the value or quality of the parameter prior to treatment. As another example, the efficacy of treatment can be evaluated, e.g., as compared to a standard, e.g., slowing progression of the disease as compared to a usual time course for the disease in a cohort that has not been treated or compared to historical data on disease progression. Treating a disease also includes slowing its progress; and/or relieving the disease, e.g., causing regression of the disease. In some embodiments, the progressive worsening (e.g., the increasing intensity) of a symptom is slowed, reduced, or halted.

"Preventing" (or prevention of) a disease includes stopping a disease from occurring in a subject, who may be predisposed to the disease but has not yet been diagnosed as having it. Preventing a disease also includes delaying the onset of the disease. The efficacy of the prevention can be evaluated, e.g., as compared to a standard, e.g., delaying onset of the disease as compared to a usual time of onset for the disease in a cohort that has not been treated or compared to historical data on disease onset.

As used herein and depending on the context in which it is used, "therapeutically effective amount" refers to an amount which is effective in reducing, eliminating, treating, preventing or controlling a symptom of a disorder or condition. The term "controlling" is intended to refer to all processes wherein there may be a slowing, interrupting, arresting, or stopping of the progression of the diseases and conditions described herein, but does not necessarily indicate a total elimination of all disease and condition symptoms, and is intended to include prophylactic treatment.

Aspects of the present subject matter relate to administering an IL-7, IL-7R, IL-15, and/or IL-15R inhibitor to a subject at risk of developing an ocular immunoinflammatory disease.

Dry Eye Disease (DED)

DED and related diseases can be caused by autoimmune and environmental conditions as well as any activity that decreases the rate of blinking. Alternatively, DED and related diseases are caused by decreased tear production or a change in tear composition that results in inadequate lubrication of the eye. Contact lens use, eye surgery, and eye injury can induce DED. Finally, DED often occurs as a consequence of aging and hormonal changes.

DED is a multifactorial disorder of the tears and ocular surface that results in symptoms of discomfort, visual disturbance, and tear film instability, with potential damage to the ocular surface. It is accompanied by increased osmolarity of the tear film and inflammation of the ocular surface (Lemp Mass. Report of the National Eye Institute/Industry Workshop on clinical trials in dry eyes. CLAO J 1995; 21:221-2). For a more detailed definition, see The definition and classification of dry eye disease: report of the Definition and Classification Subcommittee of the International Dry Eye WorkShop. Ocular Surface. 2007 April; 5(2):75-92, the entire content of which is incorporated herein by reference. The method of therapy inhibits or reduces the severity of at least one of these signs or symptoms.

Synonyms and related disorders of DED include, but are not limited to, keratoconjunctivitis sicca (KCS), Sjögren syndrome (SS), Sjögren syndrome associated keratoconjunctivitis sicca, non-Sjögren syndrome associated keratoconjunctivitis sicca, keratitis sicca, sicca syndrome, xerophthalmia, tear film disorder, decreased tear production, aqueous tear deficiency (ATD), meibomian gland dysfunction (MGD), and evaporative loss. In some embodiments, a subject is identified as suffering from DED or a related disorder by detecting a sign or symptom selected from the group consisting of dry, scratchy, stingy, itchy, burning or pressured sensations, irritation, pain, redness, inflammation, discharge, and excessive eye watering. In various embodiments, a subject is identified as suffering from DED or a related disorder if their tear composition is insufficient for proper eye tissue lubrication. The method of therapy for DED inhibits or reduces the severity of at least one of sign or symptom of DED.

Subjects at risk of developing DED include subjects who are taking antihistamines, nasal decongestants, tranquilizers, certain blood pressure medicines, Parkinson's medications, birth control pills and/or anti-depressants; subjects with a skin disease on or around the eyelids can result in dry eye; subjects suffering from a disease of the glands in the eyelids (such as meibomian gland dysfunction); subjects who are pregnant; female subjects who are on hormone replacement therapy (such as estrogen and/or progesterone); subjects who have had the refractive surgery known as LASIK; subjects who have suffered from a chemical or thermal burn on the membrane lining the eyelids and covering the eye; subjects afflicted with allergies; subjects afflicted with an immune system disorder (such as Sjögren's syndrome, lupus, or rheumatoid arthritis); subjects who have had an eye infection; subjects who have had ocular exposure to an irritant such as a chemical fume or tobacco smoke; and subjects with exposure keratitis.

Autoimmune Uveitis

The Th17 response plays a major pathogenic role is autoimmune uveitis. See, for example, Yoshimura et al., (2009) Rheumatology (Oxford). 2009; 48:347-354, the entire content of which is incorporated herein by reference. Uveitis is swelling and irritation of the uvea, the middle layer of the eye. The uvea provides most of the blood supply to the retina. Uveitis can be caused by autoimmune disorders, including rheumatoid arthritis or ankylosing spondylitis. The most common form of uveitis is anterior uveitis. This involves inflammation in the front part of the eye. It is often called iritis because it usually only affects the iris, the colored part of the eye. The inflammation may be linked with autoimmune diseases. The disorder may affect only one eye. It is most common in young and middle-aged people. Posterior uveitis affects the back part of the uvea. It involves primarily the choroid, which is a layer of blood vessels and connective tissue in the middle part of the eye. This type of uveitis is called choroiditis. If the retina is also involved, it is called chorioretinitis. Subjects with an autoimmune disease may develop this condition. Another form of uveitis is pars planitis. This inflammation affects the narrowed area (pars plana) between the colored part of the eye (iris) and the choroid. Pars planitis most often occurs in young men. It is generally not associated with any other disease. However, it may be linked to Crohn's disease and multiple sclerosis.

As used herein "autoimmune uveitis" refers to uveitis that is caused or associated with an autoimmune disorder.

Ocular Graft Versus Host Disease (GVHD)

Increased IL-17 levels in tears of patients with ocular GVHD has been observed. See, for example, Kang et al., (2011) J Korean Med Sci, 26: 938-944, the entire content of which is incorporated herein by reference. Ocular Graft Versus Host Disease (GVHD) occurs in patients who have undergone allogenic hematological stem cell transplantation. It can occur in patients who have acute or chronic GVHD, though it is more common in patients with the chronic form. Approximately 40-90% of patients with chronic GVHD will develop ocular symptoms. Ocular manifestations can include moderate to severe keratoconjuncitvitis sicca, bilateral marginal keratitis, anterior uveitis, corneal ulceration or neovascularization.

Memory Th17 Cells

T lymphocytes are circulating small white blood cells that play a central role in cell-mediated immunity. T helper cells (Th) are one subgroup of T lymphocytes expressing a surface marker protein Cluster of Differentiation 4 (CD4). Memory Th17 cells are a recently-identified population of T helper cells that produce interleukin-17 (IL-17). Memory Th17 cells may be referred to herein as "Th17 cells."

Human IL-7. IL-15, IL-7R and IL-15R

Amino acid sequences of IL-7 are accessible in public databases by the UniProt database accession number P13232 and are set forth herein as SEQ ID NO: 1 (corresponding to isoform 1), SEQ ID NO: 2 (corresponding to isoform 2), and SEQ ID NO: 3 (corresponding to isoform 3), and SEQ ID NO: 36 (corresponding to isoform 4). mRNA sequences which encode amino acid sequences of IL-7 are accessible in public databases by National Center for Biotechnology Information (NCBI) accession number NM_000880 the sequence of which is set forth herein as SEQ ID NO: 4 (corresponding to isoform 1); by NCBI accession number NM_001199886, the sequence of which is set forth herein as SEQ ID NO: 5 (corresponding to isoform 2); by NCBI accession number NM_001199887, the sequence of which is set forth herein as SEQ ID NO: 6 (corresponding to isoform 3); and by NCBI accession number NM_001199888, the sequence of which is set forth herein as SEQ ID NO: 7 (corresponding to isoform 4). The UniProt database entry for accession number P13232 is hereby incorporated herein by reference in its entirety.

Amino acid sequences of interleukin-7 receptor-α (CD127) are accessible in public databases by the UniProt database accession number P16871 and are set forth herein as SEQ ID NO: 8 (corresponding to isoform 1), SEQ ID NO: 9 (corresponding to isoform 3), SEQ ID NO: 10 (corresponding to isoform 4), and SEQ ID NO: 11 (corresponding to isoform 2). An mRNA sequence which encodes an amino acid sequence of interleukin-7 receptor-α (CD127) is accessible in public databases by NCBI accession number NM_002185, the sequence of which is set forth herein as SEQ ID NO: 12 (all isoforms). The UniProt database entry for accession number P16871 is hereby incorporated herein by reference in its entirety.

Amino acid sequences of common-T chain receptor (CD132) are accessible in public databases by the UniProt database accession number P31785 and are set forth herein as SEQ ID NO: 13 (corresponding to isoform 1) and SEQ ID NO: 14 (corresponding to isoform 2). An mRNA which encodes a common-γ chain receptor (CD132) amino acid sequence is accessible in public databases by NCBI accession number NM_000206, the sequence of which is set forth herein as SEQ ID NO: 15 (corresponding to isoform 1). The UniProt database entry for accession number P31785 is hereby incorporated herein by reference in its entirety.

Amino acid sequences of IL-15 are accessible in public databases by the UniProt database accession number P40933 and are set forth herein as SEQ ID NO: 16 (corresponding to isoform IL15-S48AA) and SEQ ID NO: 17 (corresponding to isoform IL15-S21AA). mRNA sequences which encode amino acid sequences of IL-15 are accessible in public databases by NCBI accession number NM_000585, the sequence of which is set forth herein as SEQ ID NO: 18 (corresponding to isoform IL15-S48AA); and by NCBI accession number NM_172175, the sequence of which is set forth herein as SEQ ID NO: 19 (corresponding to isoform IL15-S21AA). The UniProt database entry for accession number P40933 is hereby incorporated herein by reference in its entirety.

An amino acid sequence of IL-2/IL-15 receptor beta chain (CD122) is accessible in public databases by the UniProt database accession number P14784 and is set forth herein as SEQ ID NO: 20. An mRNA sequence which encodes an amino acid sequence of IL-2/IL-15 receptor beta chain (CD122) is accessible in public databases by NCBI accession number NM_000878, the sequence of which is set forth herein as SEQ ID NO: 21. The UniProt database entry for accession number P14784 is hereby incorporated herein by reference in its entirety.

Amino acid sequences of IL-15R alpha are accessible in public databases by the UniProt database accession number Q13261 and are set forth herein as SEQ ID NO: 22 (corresponding to isoform 1), SEQ ID NO: 23 (corresponding to isoform 2), SEQ ID NO: 24 (corresponding to isoform 3), SEQ ID NO: 25 (corresponding to isoform 4), SEQ ID NO: 26 (corresponding to isoform 5), SEQ ID NO: 27 (corresponding to isoform 6), SEQ ID NO: 28 (corresponding to isoform 7), SEQ ID NO: 29 (corresponding to isoform 8), and SEQ ID NO: 30 (corresponding to isoform 9). mRNA sequences which encode amino acid sequences of IL-15R alpha are accessible in public databases by NCBI accession number NM_002189, the sequence of which is set forth herein as SEQ ID NO: 31 (corresponding to isoform 1); by NCBI accession number NM_172200, the sequence of which is set forth herein as SEQ ID NO: 32 (corresponding to isoform 2); by NCBI accession number NM_001243539, the sequence of which is set forth herein as SEQ ID NO: 33 (corresponding to isoform 9); and by NCBI accession number NM_001256765, the sequence of which is set forth herein as SEQ ID NO: 34 (corresponding to isoform 4). The UniProt database entry for accession number Q13261 is hereby incorporated herein by reference in its entirety.

With respect to isoform 1 of interleukin-7 receptor-α (CD127), the signal peptide is predicted to include amino acid positions 1-20, the extracellular domain is predicted to include amino acids 21-239, the transmembrane domain is predicted to include 240-264, and the cytoplasmic domain is predicted to include amino acids 265-459, where the amino acid positions are numbered as in SEQ ID NO: 8.

With respect to isoform 1 of common-γ chain receptor (CD132), the signal peptide is predicted to include amino acid positions 1-22, the extracellular domain is predicted to include amino acids 23-262, the transmembrane domain is predicted to include 263-283, and the cytoplasmic domain is predicted to include amino acids 284-369, where the amino acid positions are numbered as in SEQ ID NO: 13.

With respect to IL-2/IL-15 receptor beta chain (CD122), the signal peptide is predicted to include amino acid positions 1-26, the extracellular domain is predicted to include amino acids 27-240, the transmembrane domain is predicted to include 241-265, and the cytoplasmic domain is predicted to include amino acids 266-551, where the amino acid positions are numbered as in SEQ ID NO: 20.

With respect to isoform 1 of IL-15R alpha, the signal peptide is predicted to include amino acid positions 1-30, the extracellular domain is predicted to include amino acids 31-205, the transmembrane domain is predicted to include 206-228, and the cytoplasmic domain is predicted to include amino acids 229-267, where the amino acid positions are numbered as in SEQ ID NO: 22.

Extracellular domains of proteins within the IL-7 and IL-15 receptor complexes are known. For example, an extracellular domain of interleukin-7 receptor-α (CD127) may include amino acids 1-239 or 21-239 of SEQ ID NO: 8; an extracellular domain of common-γ chain receptor (CD132) may include amino acids 1-262 or 23-262 of SEQ ID NO: 13; an extracellular domain of IL-15R alpha may include amino acids 1-205 or 31-205 of SEQ ID NO: 22; and an extracellular domain of IL-2/IL-15 receptor beta chain (CD122) may include amino acids 1-240 or 27-240 of SEQ ID NO: 20. In certain embodiments, an inhibitor of IL-7 transduction comprises a soluble compound comprising an extracellular domain of a protein within interleukin-7 receptor-α (CD127) or common-γ chain receptor (CD132). In some embodiments, an inhibitor of IL-15 transduction comprises a soluble compound comprising an extracellular domain of IL-15R alpha, IL-2/IL-15 receptor beta chain (CD122), or common-γ chain receptor (CD132). In various embodiments, an extracellular domain is part of a chimeric or fusion protein comprising the extracellular domain and a polypeptide such as an antibody Fc domain or a portion thereof.

Antibodies

The term "antibody" is used in the broadest sense and specifically covers monoclonal antibodies (including full length monoclonal antibodies), polyclonal antibodies, multispecific antibodies (e.g., bispecific antibodies), monovalent antibodies, multivalent antibodies, and antibody fragments so long as they exhibit the desired biological activity (e.g., Fab and/or single-armed antibodies).

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F (ab')$_2$; diabodies; linear antibodies; single-chain antibody molecules (e.g., scFv); and multispecific antibodies formed from antibody fragments.

The terms "full length antibody," "intact antibody," and "whole antibody" are used herein interchangeably to refer to an antibody having a structure substantially similar to a native antibody structure or having heavy chains that contain an Fc region.

An "Fv" fragment is an antibody fragment which contains a complete antigen recognition and binding site. This region consists of a dimer of one heavy and one light chain variable domain in tight association, which can be covalent in nature, for example in scFv. It is in this configuration that the three hypervariable regions (HVRs) of each variable domain interact to define an antigen binding site on the surface of the VH-VL dimer. Collectively, the six HVRs or a subset thereof confer antigen binding specificity to the antibody. However, even a single variable domain (or half of an Fv comprising only three HVRs specific for an antigen) has the ability to recognize and bind antigen, although usually at a lower affinity than the entire binding site.

A "Fab" fragment contains a variable and constant domain of the light chain and a variable domain and the first constant domain (CHI) of the heavy chain. F(ab') 2 antibody fragments comprise a pair of Fab fragments which are generally covalently linked near their carboxy termini by hinge cysteines between them. Other chemical couplings of antibody fragments are also known in the art.

"Single-chain Fv" or "scFv" antibody fragments comprise the VH and VL domains of an antibody, wherein these domains are present in a single polypeptide chain. Generally the Fv polypeptide further comprises a polypeptide linker between the VH and L domains, which enables the scFv to form the desired structure for antigen binding. For a review of scFv, see Pluckthun in The Pharmacology of Monoclonal Antibodies, Vol 113, Rosenburg and Moore eds. Springer-Verlag, New York, pp. 269-31S (1994).

The term "diabodies" refers to small antibody fragments with two antigen-binding sites, which fragments comprise a heavy chain variable domain (VH) connected to a light chain variable domain (VL) in the same polypeptide chain (VH and VL). By using a linker that is too short to allow pairing between the two domains on the same chain, the domains are forced to pair with the complementary domains of another chain and create two antigen-binding sites. Diabodies are described more fully in, for example, BP 404,097; WO 93/11161; and Hollinger et al., Proc. Natl. Acad. Sci. USA, 90:6444-6448 (1993).

The expression "linear antibodies" refers to the antibodies described in Zapata et al., Protein Eng., 8 (10): 1057-1062 (1995). Briefly, these antibodies comprise a pair of tandem Fd segments (V.sub.H-C.sub.H1-V.sub.H-C.sub.H1) which, together with complementary light chain polypeptides, form a pair of antigen binding regions. Linear antibodies can be bispecific or monospecific.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used may be made by a variety of techniques, including but not limited to the hybridoma method (see, e.g., Kohler and Milstein, Nature 256:495-97 (1975); Kozbor et al., Immunol. Today 4:72 (1983); Cole et al., in Monoclonal Antibodies and Cancer Therapy, Alan R. Liss, Inc. 77-96 (1985)), recombinant DNA methods (see, e.g., U.S. Pat. No. 4,816,567), phage-display methods (see, e.g., Clackson et al., Nature 352:624-28 (1991) and Marks et al., J. Mol. Biol. 222 (3):581-97 (1991)), and methods utilizing transgenic animals containing all or part of the human immunoglobulin loci, such methods and other exemplary methods for making monoclonal antibodies being described herein.

The term "chimeric" antibody refers to an antibody in which a portion of the heavy and/or light chain is derived from a particular source or species, while the remainder of the heavy and/or light chain is derived from a different source or species.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

Antisense Oligonucleotides

Antisense oligonucleotides are nucleotide sequences which are complementary to a specific DNA or RNA sequence. Once introduced into a cell, the complementary nucleotides combine with natural sequences produced by the cell to form complexes and block either transcription or translation. Preferably, an antisense oligonucleotide is at least 11 nucleotides in length, but can be at least 12, 15, 20, 25, 30, 35, 40, 45, or 50 or more nucleotides long. Longer sequences also can be used. Antisense oligonucleotide molecules can be directly administered or provided in a DNA construct and introduced into a cell to decrease the level of IL-7, IL-15, CD132, CD127, CD122, or IL-15R alpha gene products in the cell.

In some embodiments, antisense oligonucleotides can be deoxyribonucleotides, ribonucleotides, or a combination of both. In various embodiments, oligonucleotides mag be modified to increase the half-life of the oligonucleotide in vivo. Oligonucleotides can be synthesized manually or by an automated synthesizer, by covalently linking the 5' end of one nucleotide with the 3' end of another nucleotide with non-phosphodiester internucleotide linkages such alkylphosphonates, phosphorothioates, phosphorodithioates, alkylphosphonothioates, alkylphosphonates, phosphoramidates, phosphate esters, carbamates, acetamidate, carboxymethyl esters, carbonates, and phosphate triesters.

Modifications of gene expression can be obtained by designing antisense oligonucleotides which will form duplexes to the control, 5', or regulatory regions of the gene. Oligonucleotides derived from the transcription initiation site, e.g., between positions −10 and +10 from the start site, are used in various embodiments. Similarly, inhibition can be achieved using "triple helix" base-pairing methodology. Triple helix pairing is useful because it causes inhibition of the ability of the double helix to open sufficiently for the binding of polymerases, transcription factors, or chaperons. Therapeutic advances using triplex DNA have been described in the literature (Nicholls et al., 1993, J Immunol Meth 165:81-91). An antisense oligonucleotide also can be designed to block translation of mRNA by preventing the transcript from binding to ribosomes.

Precise complementarity is not required for successful complex formation between an antisense oligonucleotide and the complementary sequence of an IL-7, IL-15, CD132, CD127, CD122, or IL-15R alpha polynucleotide. Antisense oligonucleotides which comprise, for example, 2, 3, 4, or 5 or more stretches of contiguous nucleotides which are precisely complementary to an IL-7, IL-15, CD132, CD127, CD122, or IL-15R alpha polynucleotide, each separated by a stretch of contiguous nucleotides which are not complementary to adjacent IL-7, IL-15, CD132, CD127, CD122, or IL-15R alpha nucleotides, can provide sufficient targeting specificity for IL-7, IL-15, CD132, CD127, CD122, or IL-15R alpha mRNA, respectively. Preferably, each stretch of complementary contiguous nucleotides is at least 4, 5, 6, 7, or 8 or more nucleotides in length. Noncomplementary intervening sequences are preferably 1, 2, 3, or 4 nucleotides in length. One skilled in the art can easily use the calculated melting point of an antisense-sense pair to determine the degree of mismatching which will be tolerated between a particular antisense oligonucleotide and a particular IL-7, IL-15, CD132, CD127, CD122, or IL-15R alpha polynucleotide sequence. Antisense oligonucleotides can be modified without affecting their ability to hybridize to an IL-7, IL-15, CD132, CD127, CD122, or IL-15R alpha polynucleotide. These modifications can be internal or at one or both ends of the antisense molecule. For example, internucleoside phosphate linkages can be modified by adding cholesteryl or diamine moieties with varying numbers of carbon residues between the amino groups and terminal ribose. Modified bases and/or sugars, such as arabinose instead of ribose, or a 3', 5'-substituted oligonucleotide in which the 3' hydroxyl group or the 5' phosphate group are substituted, also can be employed in a modified antisense oligonucleotide. These modified oligonucleotides can be prepared by methods well known in the art. In some embodiments, the antisense oligonucleotide is a phosphorodiamidate morpholino oligomer (also referred to herein as a "PMO" or a "morpholino").

Ribozymes

Ribozymes are RNA molecules with catalytic activity (Uhlmann et al., 1987, Tetrahedron. Lett. 215, 3539-3542). Ribozymes can be used to inhibit gene function by cleaving an RNA sequence, as is known in the art. The mechanism of ribozyme action involves sequence-specific hybridization of the ribozyme molecule to complementary target RNA, followed by endonucleolytic cleavage. Examples include engineered hammerhead motif ribozyme molecules that can specifically and efficiently catalyze endonucleolytic cleavage of specific nucleotide sequences. The coding sequence of a polynucleotide can be used to generate ribozymes which will specifically bind to mRNA transcribed from the polynucleotide. Methods of designing and constructing ribozymes which can cleave other RNA molecules in trans in a highly sequence specific manner have been developed and described in the art. For example, the cleavage activity of ribozymes can be targeted to specific RNAs by engineering a discrete "hybridization" region into the ribozyme. The hybridization region contains a sequence complementary to the target RNA and thus specifically hybridizes with the target RNA.

Specific ribozyme cleavage sites within an RNA target can be identified by scanning the target molecule for ribozyme cleavage sites which include the following sequences: GUA, GUU, and GUC. Once identified, short RNA sequences of between 15 and 20 ribonucleotides corresponding to the region of the target RNA containing the cleavage site can be evaluated for secondary structural features which may render the target inoperable. Suitability of candidate RNA targets also can be evaluated by testing accessibility to hybridization with complementary oligonucleotides using ribonuclease protection assays. The nucleotide sequences shown in nucleotide sequences described herein (e.g., SEQ ID NOs 4-7, 12, 15, 18, 19, 21, and 31-34) and their complements provide sources of suitable hybridization region sequences. Longer complementary sequences can be used to increase the affinity of the hybridization sequence for the target. The hybridizing and cleavage regions of the ribozyme can be integrally related such that upon hybridizing to the target RNA through the complementary regions, the catalytic region of the ribozyme can cleave the target.

Ribozymes can be introduced into cells as part of a DNA construct. Mechanical methods, such as microinjection, liposome-mediated transfection, electroporation, or calcium phosphate precipitation, can be used to introduce a ribozyme-containing DNA construct into cells in which it is desired to decrease an IL-7, IL-15, CD132, CD127, CD122, or IL-15R alpha expression. Alternatively, if it is desired that the cells stably retain the DNA construct, the construct can be supplied on a plasmid and maintained as a separate element or integrated into the genome of the cells, as is known in the art. A ribozyme-encoding DNA construct can include transcriptional regulatory elements, such as a promoter element, an enhancer or VAS element, and a transcriptional terminator signal, for controlling transcription of ribozymes in the cells (U.S. Pat. No. 5,641,673). Ribozymes also can be engineered to provide an additional level of regulation, so that destruction of mRNA occurs only when both a ribozyme and a target gene are induced in the cells.

RNA Interference

As used herein, "RNA interference" compound refers to a compound capable of inducing RNA interference or "RNAi" of an IL-7, IL-15, CD132, CD127, CD122, or IL-15R alpha expression, depending on the context. RNAi involves mRNA degradation, but many of the biochemical mechanisms underlying this interference are unknown. The use of RNAi has been described in Fire et al., 1998, Carthew et al., 2001, and Elbashir et al., 2001, the contents of which are incorporated herein by reference.

Isolated RNA molecules can mediate RNAi. That is, the isolated RNA molecules of the present invention mediate degradation or block expression of mRNA that is the transcriptional product of the gene, which is also referred to as a target gene. For convenience, such mRNA may also be referred to herein as mRNA to be degraded. The terms RNA, RNA molecule (s), RNA segment(s) and RNA fragment(s) may be used interchangeably to refer to RNA that mediates RNA interference. These terms include double-stranded RNA, small interfering RNA (siRNA), hairpin RNA, single-stranded RNA, isolated RNA (partially purified RNA, essentially pure RNA, synthetic RNA, recombinantly produced RNA), as well as altered RNA that differs from naturally occurring RNA by the addition, deletion, substitution and/or alteration of one or more nucleotides. Such alterations can include addition of non-nucleotide material, such as to the end(s) of the RNA or internally (at one or more nucleotides of the RNA). Nucleotides in the RNA molecules of the present invention can also comprise nonstandard nucleotides, including non-naturally occurring nucleotides or deoxyribonucleotides. Collectively, all such altered RNAi molecules are referred to as analogs or analogs of naturally-occurring RNA. RNA of the present invention need only be sufficiently similar to natural RNA that it has the ability to mediate RNAi.

As used herein the phrase "mediate RNAi" refers to and indicates the ability to distinguish which mRNA molecules are to be afflicted with the RNAi machinery or process. RNA that mediates RNAi interacts with the RNAi machinery such that it directs the machinery to degrade particular mRNAs or to otherwise reduce the expression of the target protein. In one embodiment, the present invention relates to RNA molecules that direct cleavage of specific mRNA to which their sequence corresponds. It is not necessary that there be perfect correspondence of the sequences, but the correspondence must be sufficient to enable the RNA to direct RNAi inhibition by cleavage or blocking expression of the target mRNA.

As noted above, the RNA molecules of the present invention in general comprise an RNA portion and some additional portion, for example a deoxyribonucleotide portion. The total number of nucleotides in the RNA molecule is suitably less than in order to be effective mediators of RNAi. In preferred RNA molecules, the number of nucleotides is 16 to 29, more preferably 18 to 23, and most preferably 21-23.

Aptamers

As used herein, the terms "aptamer(s)" or "aptamer sequence(s)" are meant to refer to single stranded nucleic acids (RNA or DNA) whose distinct nucleotide sequence determines the folding of the molecule into a unique three dimensional structure. Aptamers comprising 15 to 120 nucleotides can be selected in vitro from a randomized pool of oligonucleotides (1014-1015 molecules). Aptamers that bind to pre-selected targets including proteins and peptides with high affinity and specificity can be designed and/or selected using methods known in the art. See, e.g., Cox, J. C.; Ellington, A. D. (2001) Bioorganic & Medicinal Chemistry 9 (10): 2525-2531; Cox, J. C.; Hayhurst, A.; Hesselberth, J.; Bayer, T. S.; Georgiou, G.; Ellington, A. D. (2002)

Nucleic Acids Research 30 (20): e108; and Neves, M. A. D.; O. Reinstein; M. Saad; P. E. Johnson (2010) Biophys Chem 153 (1): 9-16, the entire content of each of which is incorporated herein by reference.

Pharmaceutical Formulations and Delivery to the Eye

Dosages, formulations, dosage volumes, regimens, and methods for antagonizing the IL-7/IL-7R and IL-15/IL-17R pathways can vary. Thus, minimum and maximum effective dosages vary depending on the method of administration.

In various embodiments of the invention, a composition comprising an IL-7, IL-7R, IL-15, and/or IL-15R inhibitor may be administered only once or multiple times. For example, an IL-7, IL-7R, IL-15, and/or IL-15R inhibitor may be administered using a method disclosed herein at least about once, twice, three times, four times, five times, six times, or seven times per day week, month, or year. In some embodiments, a composition comprising an IL-7, IL-7R, IL-15, and/or IL-15R inhibitor is administered once per month. In certain embodiments, the composition is administered once per month via intravitreal injection. In various embodiments, such as embodiments involving eye drops, a composition is self-administered.

Preferred formulations are in the form of a solid, a paste, an ointment, a gel, a liquid, an aerosol, a mist, a polymer, a contact lens, a film, an emulsion, or a suspension. The formulations are administered topically, e.g., the composition is delivered and directly contacts the eye. The composition is present at a concentration of 0.01-50% (weight/volume). For example, the inhibitory composition is present at concentrations of 1% (weight/volume), 10% (weight/volume), 20% (weight/volume), 25% (weight/volume), 30% (weight/volume), 40% (weight/volume), 50% (weight/volume), or any percentage point in between. The method does not involve systemic administration or planned substantial dissemination of the composition to non-ocular tissue.

Optionally, the composition further contains a pharmaceutically-acceptable carrier. Exemplary pharmaceutical carriers include, but are not limited to, compounds selected from the group consisting of a physiological acceptable salt, poloxamer analogs with carbopol, carbopol/hydroxypropyl methyl cellulose (HPMC), carbopol-methyl cellulose, a mucolytic agent, carboxymethylcellulose (CMC), hyaluronic acid, cyclodextrin, and petroleum. In one embodiment, the mucolytic agent is N-acetyl cysteine.

For the treatment of an ocular immunoinflammatory disease, an IL-7, IL-7R, IL-15, and/or IL-15R inhibitor (e.g., a pharmaceutical composition comprising an IL-7, IL-7R, IL-15, and/or IL-15R inhibitor) may be administered locally, e.g., as a topical eye drop, peri-ocular injection (e.g., sub-tenon), intraocular injection, intravitreal injection, retrobulbar injection, intraretinal injection, subconjunctival injection, or using iontophoresis, or peri-ocular devices which can actively or passively deliver drug.

Pharmaceutical formulations adapted for topical administration may be formulated as aqueous solutions, ointments, creams, suspensions, lotions, powders, solutions, pastes, gels, sprays, aerosols, liposomes, microcapsules, microspheres, or oils.

Pharmaceutical formulations adapted for topical administrations to the eye include eye drops wherein an IL-7, IL-7R, IL-15, and/or IL-15R inhibitor is dissolved or suspended in a suitable carrier, especially an aqueous solvent. Formulations to be administered to the eye will have ophthalmically compatible pH and osmolality. The term "ophthalmically acceptable vehicle" means a pharmaceutical composition having physical properties (e.g., pH and/or osmolality) that are physiologically compatible with ophthalmic tissues.

In some embodiments, an ophthalmic composition of the present invention is formulated as sterile aqueous solutions having an osmolality of from about 200 to about 400 milliosmoles/kilogram water ("mOsm/kg") and a physiologically compatible pH. The osmolality of the solutions may be adjusted by means of conventional agents, such as inorganic salts (e.g., NaCl), organic salts (e.g., sodium citrate), polyhydric alcohols (e.g., propylene glycol or sorbitol) or combinations thereof.

In various embodiments, the ophthalmic formulations of the present invention may be in the form of liquid, solid or semisolid dosage form. The ophthalmic formulations of the present invention may comprise, depending on the final dosage form, suitable ophthalmically acceptable excipients. In some embodiments, the ophthalmic formulations are formulated to maintain a physiologically tolerable pH range. In certain embodiments, the pH range of the ophthalmic formulation is in the range of from about 5 to about 9. In some embodiments, pH range of the ophthalmic formulation is in the range of from about 6 to about 8, or is about 6.5, about 7, or about 7.5.

In some embodiments, the composition is in the form of an aqueous solution, such as one that can be presented in the form of eye drops. By means of a suitable dispenser, a desired dosage of the active agent can be metered by administration of a known number of drops into the eye, such as by one, two, three, four, or five drops.

One or more ophthalmically acceptable pH adjusting agents and/or buffering agents can be included in a composition of the invention, including acids such as acetic, boric, citric, lactic, phosphoric, and hydrochloric acids; bases such as sodium hydroxide, sodium phosphate, sodium borate, sodium citrate, sodium acetate, and sodium lactate; and buffers such as citrate/dextrose, sodium bicarbonate, and ammonium chloride. Such acids, bases, and buffers can be included in an amount required to maintain pH of the composition in an ophthalmically acceptable range. One or more ophthalmically acceptable salts can be included in the composition in an amount sufficient to bring osmolality of the composition into an ophthalmically acceptable range. Such salts include those having sodium, potassium, or ammonium cations and chloride, citrate, ascorbate, borate, phosphate, bicarbonate, sulfate, thiosulfate, or bisulfite anions.

Pharmaceutical compositions for ocular delivery also include in situ gellable aqueous composition. Such a composition comprises a gelling agent in a concentration effective to promote gelling upon contact with the eye or with lacrimal fluid. Suitable gelling agents include but are not limited to thermosetting polymers. The term "in situ gellable" as used herein includes not only liquids of low viscosity that form gels upon contact with the eye or with lacrimal fluid, but also includes more viscous liquids such as semi-fluid and thixotropic gels that exhibit substantially increased viscosity or gel stiffness upon administration to the eye. See, for example, Ludwig, Adv. Drug Deliv. Rev. 3; 57:1595-639 (2005), the entire content of which is incorporated herein by reference.

Drug Delivery by Contact Lens

The invention comprises a contact lens and a composition that inhibits an activity of an inflammatory interleukin-1 cytokine. For example, the composition is incorporated into or coated onto the lens. The composition is chemically bound or physically entrapped by the contact lens polymer.

Alternatively, a color additive is chemically bound or physically entrapped by the polymer composition that is released at the same rate as the therapeutic drug composition, such that changes in the intensity of the color additive indicate changes in the amount or dose of therapeutic drug composition remaining bound or entrapped within the polymer. Alternatively, or in addition, an ultraviolet (UV) absorber is chemically bound or physically entrapped within the contact lens polymer. The contact lens is either hydrophobic or hydrophilic.

Exemplary materials used to fabricate a hydrophobic lens with means to deliver the compositions of the invention include, but are not limited to, amefocon A, amsilfocon A, aquilafocon A, arfocon A, cabufocon A, cabufocon B, carbosilfocon A, crilfocon A, crilfocon B, dimefocon A, enflufocon A, enflofocon B, erifocon A, flurofocon A, flusilfocon A, flusilfocon B, flusilfocon C, flusilfocon D, flusilfocon E, hexafocon A, hofocon A, hybufocon A, itabisfluorofocon A, itafluorofocon A, itafocon A, itafocon B, kolfocon A, kolfocon B, kolfocon C, kolfocon D, lotifocon A, lotifocon B, lotifocon C, melafocon A, migafocon A, nefocon A, nefocon B, nefocon C, onsifocon A, oprifocon A, oxyfluflocon A, paflufocon B, paflufocon C, paflufocon D, paflufocon E, paflufocon F, pasifocon A, pasifocon B, pasifocon C, pasifocon D, pasifocon E, pemufocon A, porofocon A, porofocon B, roflufocon A, roflufocon B, roflufocon C, roflufocon D, roflufocon E, rosilfocon A, satafocon A, siflufocon A, silafocon A, sterafocon A, sulfocon A, sulfocon B, telafocon A, tisilfocon A, tolofocon A, trifocon A, unifocon A, vinafocon A, and wilofocon A.

Exemplary materials used to fabricate a hydrophilic lens with means to deliver the compositions of the invention include, but are not limited to, abafilcon A, acofilcon A, acofilcon B, acquafilcon A, alofilcon A, alphafilcon A, amfilcon A, astifilcon A, atlafilcon A, balafilcon A, bisfilcon A, bufilcon A, comfilcon A, crofilcon A, cyclofilcon A, darfilcon A, deltafilcon A, deltafilcon B, dimefilcon A, droxfilcon A, elastofilcon A, epsilfilcon A, esterifilcon A, etafilcon A, focofilcon A, galyfilcon A, genfilcon A, govafilcon A, hefilcon A, hefilcon B, hefilcon C, hilafilcon A, hilafilcon B, hioxifilcon A, hioxifilcon B, hioxifilcon C, hydrofilcon A, lenefilcon A, licryfilcon A, licryfilcon B, lidofilcon A, lidofilcon B, lotrafilcon A, lotrafilcon B, mafilcon A, mesafilcon A, methafilcon B, mipafilcon A, nelfilcon A, netrafilcon A, ocufilcon A, ocufilcon B, C, ocufilcon D, ocufilcon E, ofilcon A, omafilcon A, oxyfilcon A, pentafilcon A, perfilcon A, pevafilcon A, phemfilcon A, polymacon, senofilcon A, silafilcon A, siloxyfilcon A, surfilcon A, tefilcon A, tetrafilcon A, trilfilcon A, vifilcon A, vifilcon B, and xylofilcon A.

General Definitions

Unless specifically defined otherwise, all technical and scientific terms used herein shall be taken to have the same meaning as commonly understood by one of ordinary skill in the art (e.g., in cell culture, molecular genetics, and biochemistry).

As used herein, the term "about" in the context of a numerical value or range means ±10% of the numerical value or range recited or claimed, unless the context requires a more limited range.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible It is understood that where a parameter range is provided, all integers within that range, and tenths thereof, are also provided by the invention. For example, "0.2-5 mg" is a disclosure of 0.2 mg, 0.3 mg, 0.4 mg, 0.5 mg, 0.6 mg etc. up to and including 5.0 mg.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

Example 1: Effects of IL-7/IL-7R and IL-15/IL-15R Signaling Inhibition on the Maintenance of DED Memory Th17 Cells A goal of this study was to show that diminishing or eliminating memory Th17 cell-mediated ocular surface inflammation in DED can be achieved by interfering with the survival of memory Th17 cells through the topical blockade of IL-7/IL-7R and IL-15/IL-15R signaling. Experiments were performed as described below.

Figure 1B:
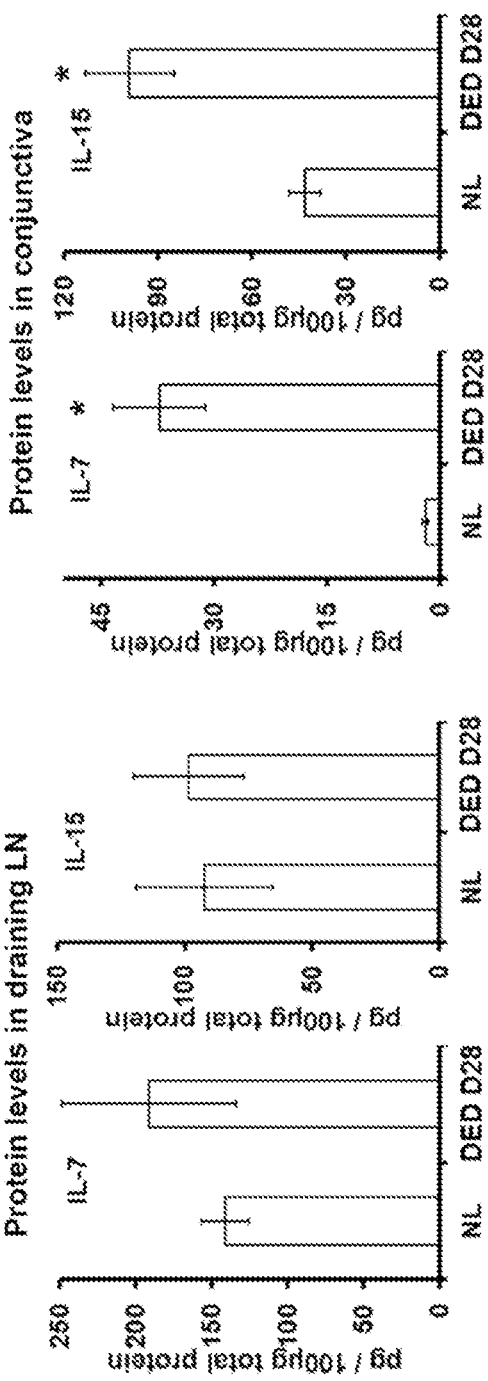
Figure 1C:
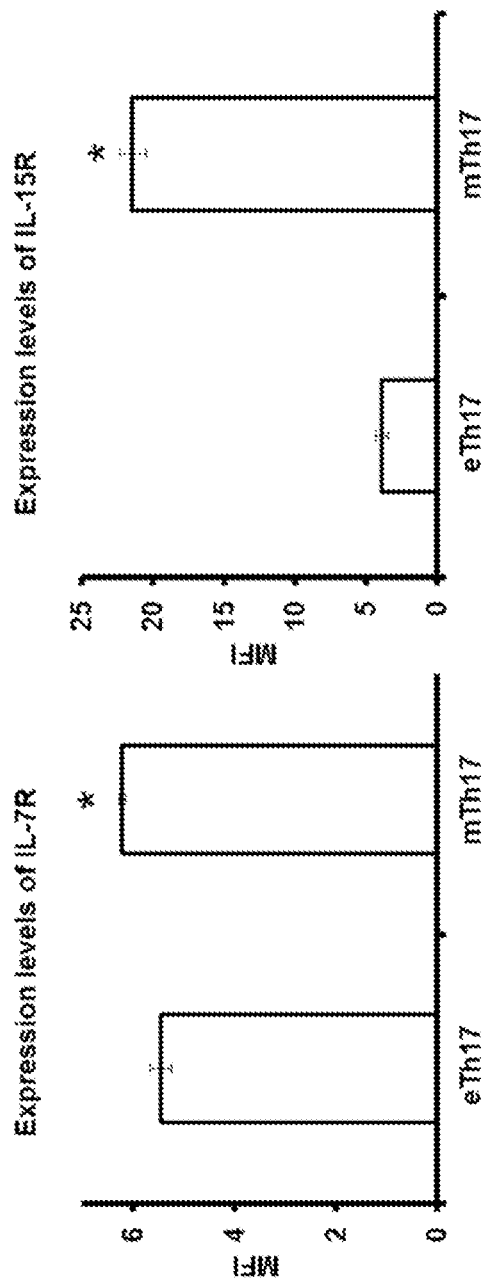

Chronic DED develops when mice are exposed to desiccating stress using a controlled environment chamber for 14 days and then housed in a standard environment for additional 14 days. There is an increase in the expression levels of IL-7 and IL-15 in both ocular surface and draining lymph nodes (DLNs) (FIG. 1A). In addition, memory Th17 cells from chronic DED also exhibit a significant up-regulation of both IL-7R and IL-15R (FIG. 1B).

Figure 2:
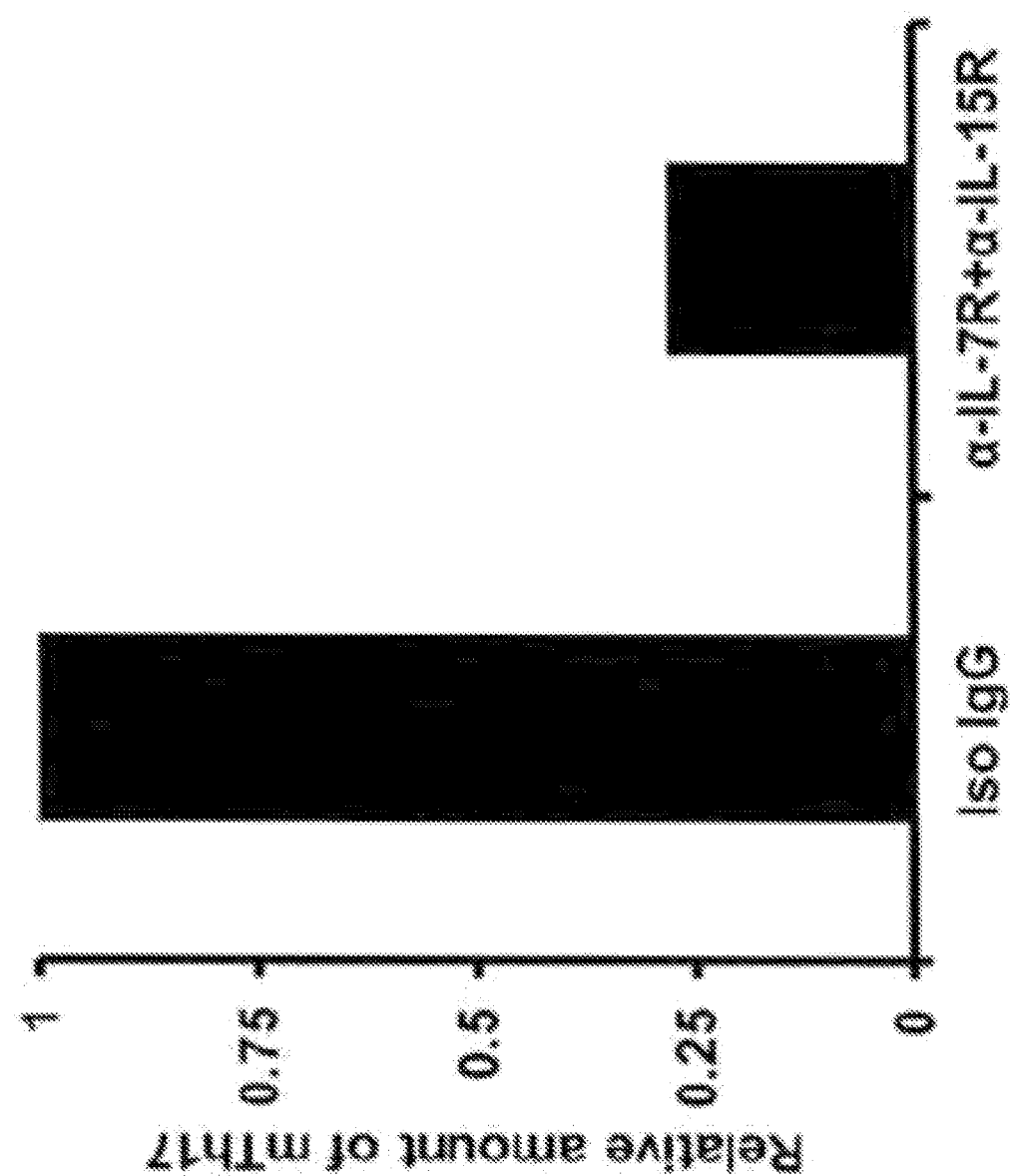
FIG. 2 is a graph showing that blockade of IL-7 and IL-15 receptors inhibits memory Th17 cells in chronic DED. Total DLN explant cultured in the presence of anti-IL-7R and anti-IL-15R antibodies showed a >70% reduction in the frequency of memory Th17 cells compared to that cultured with isotype IgG.
Figure 3:
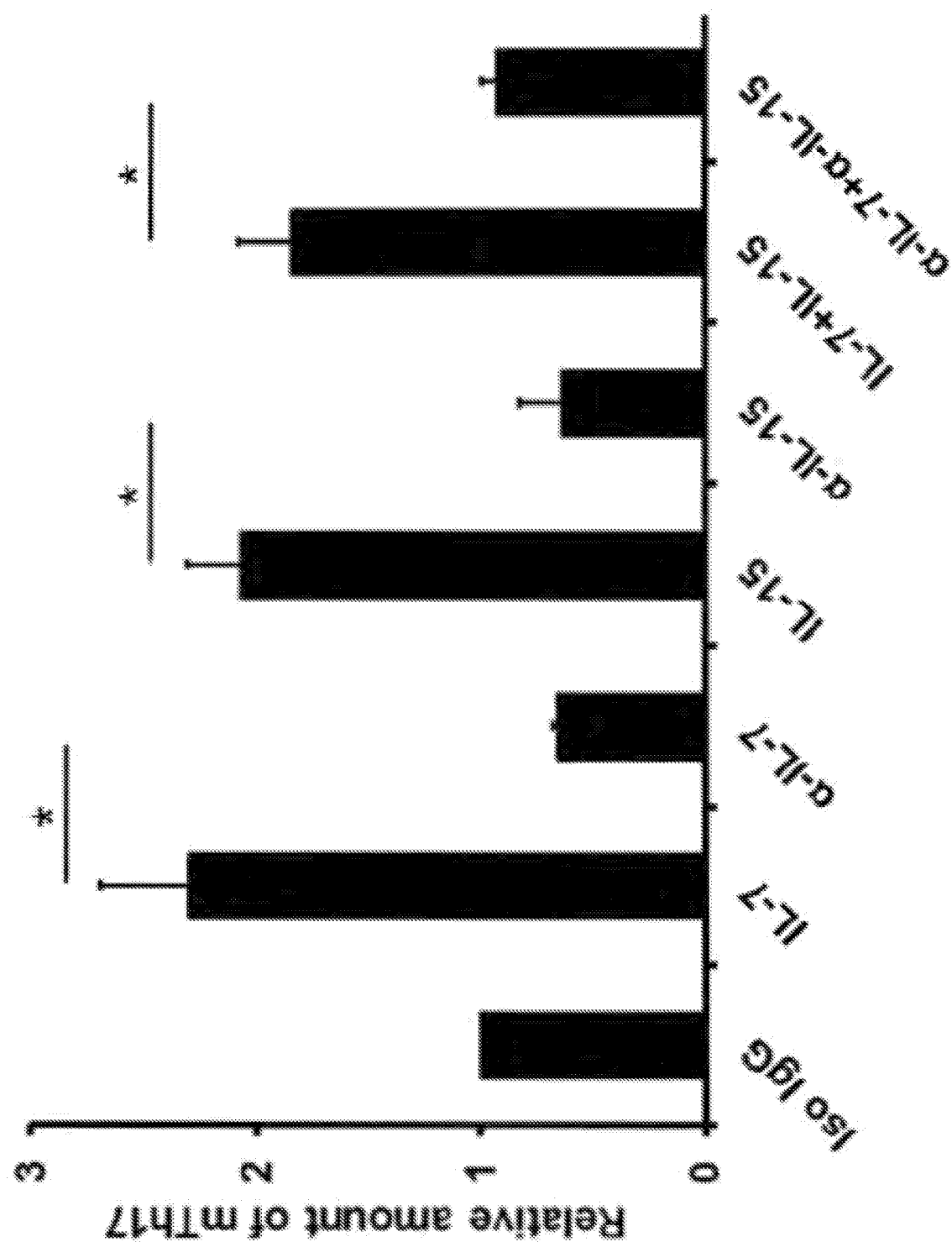
FIG. 3 is a graph showing that blockade of IL-7 and IL15 inhibits memory Th17 cells in chronic DED. Total DLN explant cultured in the presence of IL-7, IL-15, or combined IL-7 and IL-15 preserved significantly more memory Th17 cells than neutralization of each of them, respectively. *, $p<0.05$.
Figure 4A:
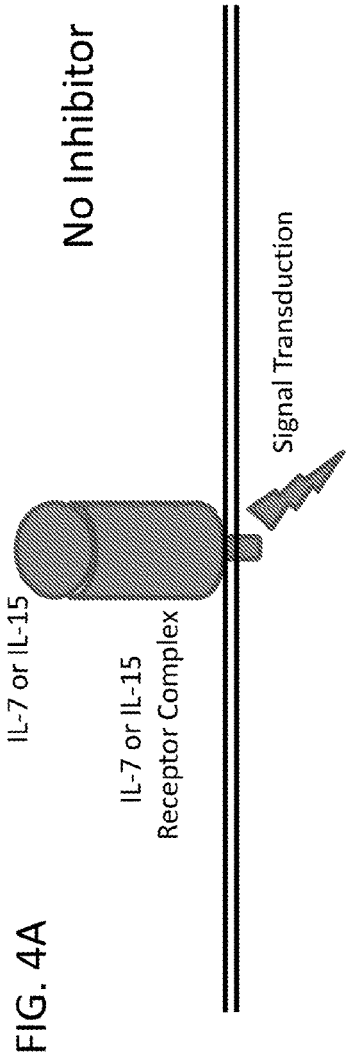
FIGS. 4A-4C are cartoons showing non-limiting examples of IL-7 and IL-15 inhibition.
Figure 4B:
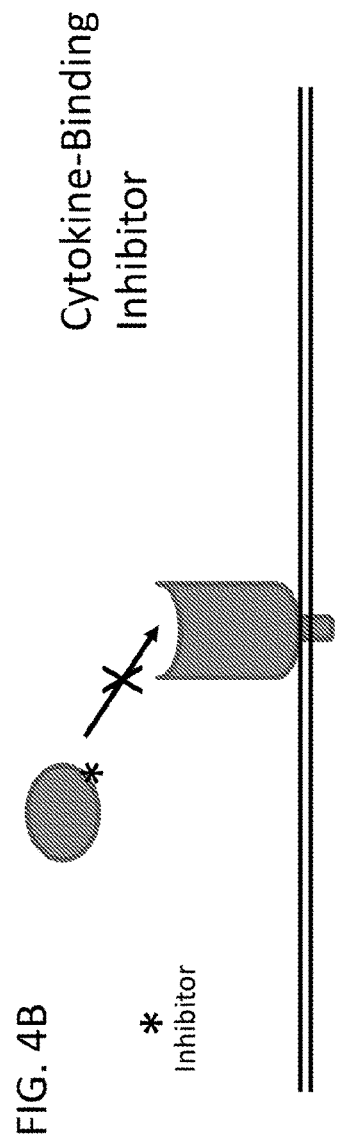
Figure 4C:
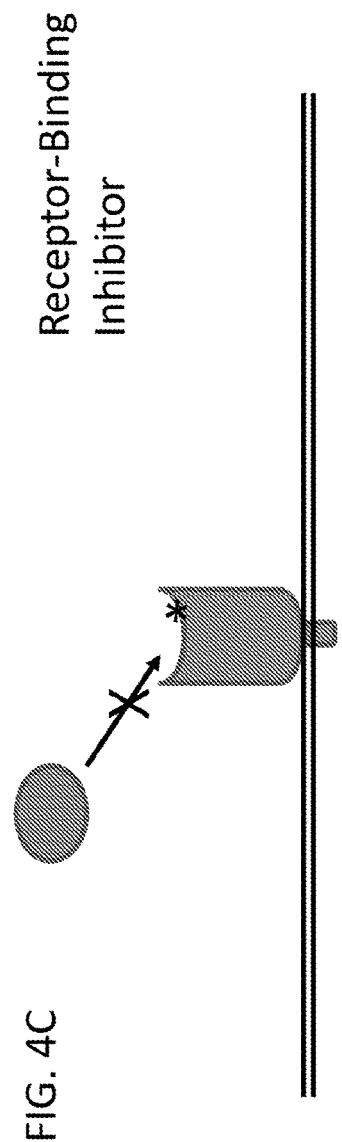

Next examined were the effects of IL-7/IL-7R and IL-15/IL-15R signaling blockade on the maintenance of DED memory Th17 cells using an in vitro culture system. Total DLNs were isolated from chronic DED and cultured for 72 hours. Initially, antibodies targeting the cytokine receptors were tested. After adding anti-IL-7R and anti-IL-15R antibodies to the explant culture, the frequency of recovered memory Th17 cells was reduced by >70% (FIG. 2). Thereafter, effects of modifying the environmental cytokine milieu on the maintenance of memory Th17 cells were investigated. Specifically, the DLN explant cultures were supplemented with the following various factors: IL-7, IL-15, combination of IL-7 and IL-15, anti-IL-7 antibody, anti-IL-15 antibody, combination of anti-IL-7 and anti-IL-15 antibodies, or control IgG. The presence of IL-7, IL-15, or combination of IL-7 and IL-15 led to significantly higher frequencies of recovered memory Th17 cells than the presence of anti-IL-7, anti-IL-15, or combination of anti-IL-7 and anti-IL-15 antibodies (p<0.05) (FIG. 3).

These findings demonstrate that both IL-7 and IL-15 maintain memory Th17 cells in DED. As described herein, reducing IL-7 and/or IL-15 signaling is a useful and specific therapeutic approach for treating DED.

Figure 5A:
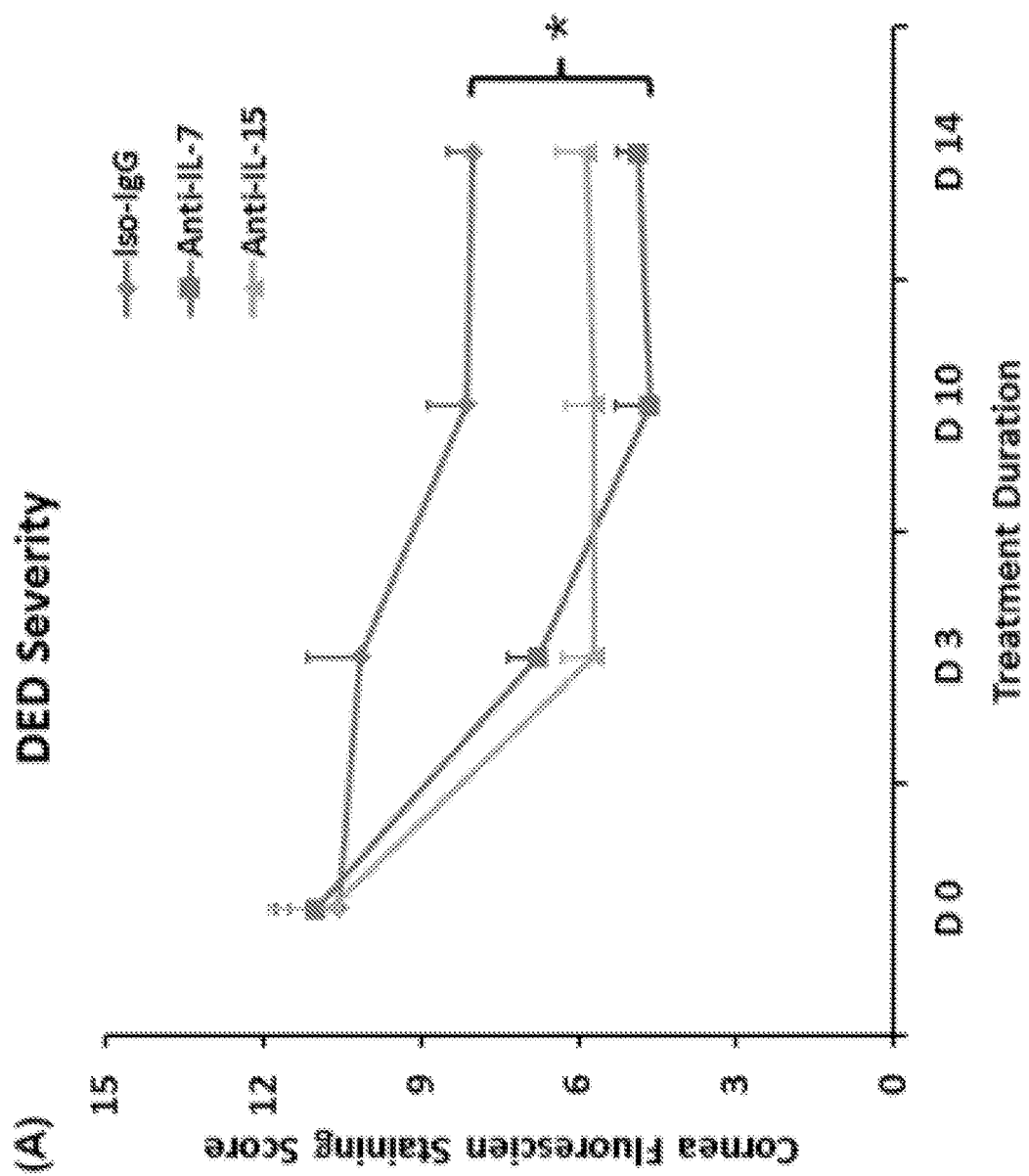
FIGS. 5A-5B are graphs showing that in vivo topical treatment with anti-IL-7 or anti-IL-15 antibody significantly decreased disease severity through depleting memory Th17 cells in chronic DED mice. (FIG. SA) DED was induced in mice and then these mice were treated with topical anti-IL-7, anti-IL-15, or isotype IgG (control group) eye drops for 14 days. Each of anti-IL-7 and anti-IL-15 treatment significantly decreased disease severity. *, $p<0.05$ at D3, D10, and D14 as compared with control group.
Figure 5B:
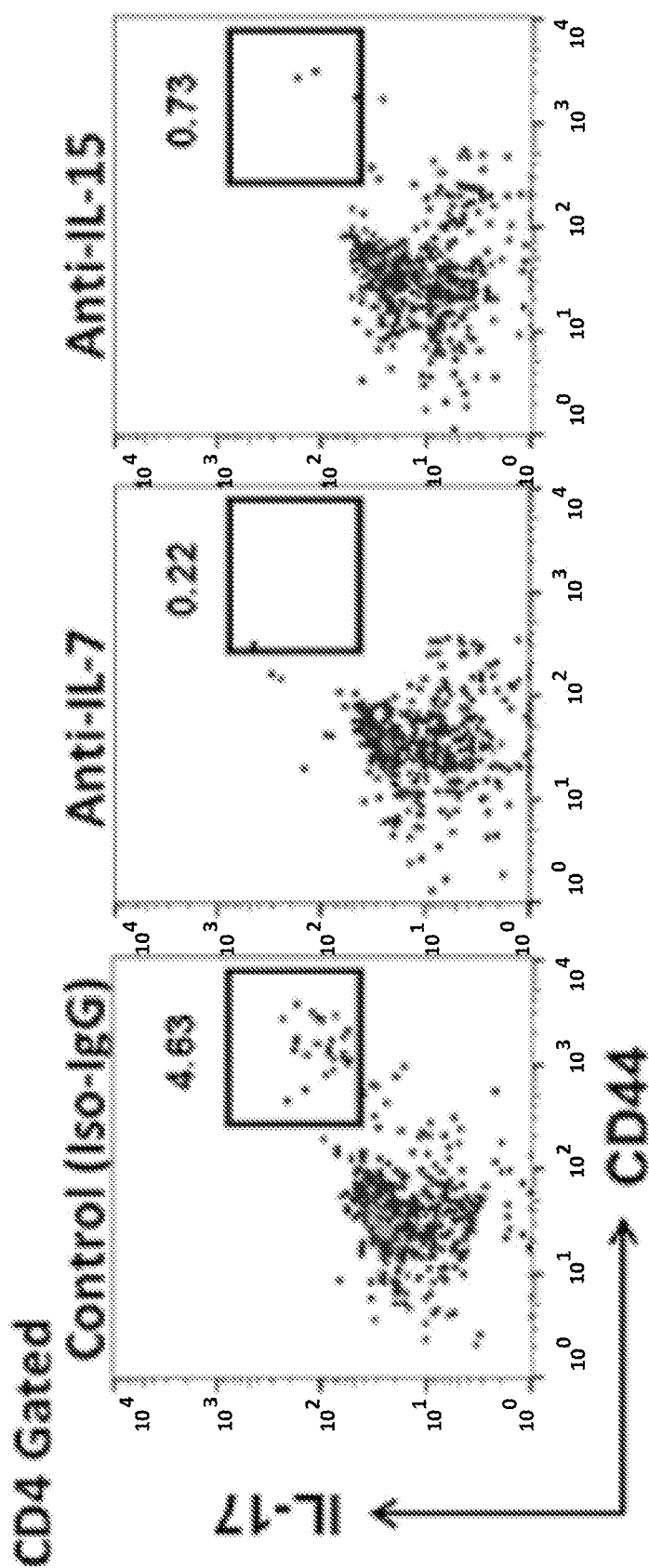
Figure 6:
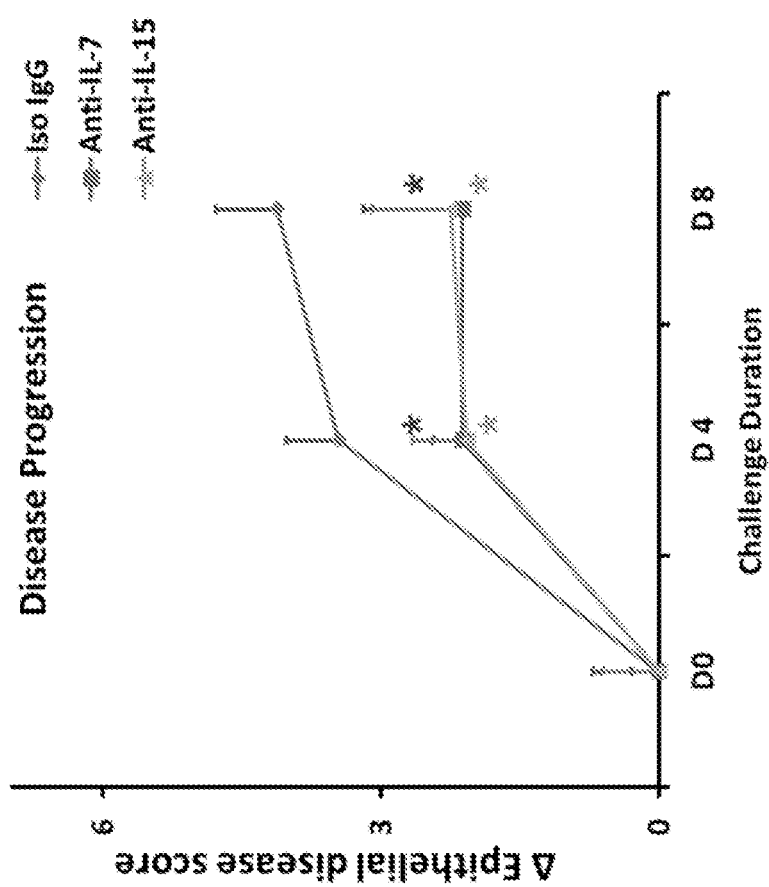
FIG. 6 is a graph showing that topical anti-IL-7 and anti-IL-15 antibody treatments have a long-term therapeutic effect. Chronic DED mice previously treated with topical anti-IL-7, anti-IL-15, or isotype IgG were re-challenged by desiccating environmental stress for 8 days without any further Ab treatment. Both anti-IL-7 and anti-IL-15 antibody pre-treated groups showed significantly reduced disease progression and severity as compared to isotype IgG. Δ epithelial disease score=disease score after re-challenge–disease score before re-challenge *, p<0.05.

Example 2: Topical Treatment with IL-7 and IL-15 Inhibitors Reduces DED Severity In vivo topical treatment with anti-IL-7 or anti-IL-15 antibodies significantly decreased disease severity and depleted memory Th17 cells in chronic DED mice. DED was induced in mice and the mice were treated with topical anti-IL-7, anti-IL-15, or isotype IgG (control group) eye drops for 14 days. Both anti-IL-7 and anti-IL-15 treatment significantly decreased disease severity as compared with control group (FIG. 5A). At the end of the treatment, ocular surface memory Th17 cells were almost completely depleted by each of anti-IL-7 and anti-IL-15 treatment (FIG. 5B).

Mouse IL-7 polyclonal antibody was used as the anti-IL-7 antibody in this study (Clone #AB-407, R&D Systems, Minneapolis, Minn., USA) at a dose of 10 µg three times per day (1 mg/ml). This antibody was provided in lyophilized form by the manufacture (R&D Systems) and was reconstituted in sterile phosphate buffered saline (PBS).

Anti-mouse IL-15 antibody was used as the anti-IL-15 antibody in this study (Clone #AIO.3, eBioscience, San Diego, Calif., USA) at a dose of 10 µg three times per day (1 mg/ml). This antibody was provided in azide-free aqueous buffer by the manufacture (eBioscience).

Isotype IgG is Polyclonal goat IgG (Catalog #ab37373, Abcam, Cambridge, Mass., USA). It was administered at a dose of 10 µg three times per day (1 mg/ml). This antibody was provided in borate buffered saline by the manufacture (Abcam).

Corneal fluorescein staining was used as a clinical evaluation tool for DED severity. Fluorescein (Sigma-Aldrich, St. Louis, Mo., USA; 1 µl 2.5%) was applied into the lateral conjunctival sac of the mice, and after 3 minutes, corneas were examined with a slit lamp biomicroscope under cobalt blue light. Punctate staining was recorded in a masked manner with the standard National Eye Institute grading system of 0-3 for each of the five areas of the cornea-central, superior, inferior, nasal, and temporal (CLAO J. 1995; 21:221-32).

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for treating a subject afflicted with Dry Eye Disease (DED), comprising locally administering to an eye of the subject a composition consisting of a neutralizing anti-IL-15R antibody or an antibody that binds to IL-15, or a neutralizing anti-IL-7R antibody or an antibody that binds to IL-7, and an ophthalmically acceptable vehicle.

2. The method of claim 1, wherein treating the subject afflicted with the ocular immunoinflammatory disorder comprises inhibiting the survival or proliferation of a Th17 cell in an eye tissue.

3. The method of claim 1, wherein said subject suffers from a sandy or gritty feeling as if something is in the eye, eye dryness, heavy eyelids, stinging, itching, burning, irritation, pain, redness, inflammation, discharge, inability to cry when emotionally stressed, eye fatigue, blurred vision, or excessive watering, and wherein said method inhibits or reduces the severity of the sandy or gritty feeling as if something is in the eye, eye dryness, heavy eyelids, stinging, itching, burning, irritation, pain, redness, inflammation, discharge, inability to cry when emotionally stressed, eye fatigue, blurred vision, or excessive watering.

4. The method of claim 1, wherein:
   (a) the composition is in the form of a solid, an ointment, a gel, a liquid, an aerosol, a mist, a polymer, a contact lens, a film, an emulsion, or a suspension;
   (b) said composition is administered topically;
   (c) said method does not comprise systemic administration to non-ocular tissue of the composition; or
   (d) the composition is administered by the subject.

5. The method of claim 1, wherein the number of memory Th17 cells in the eye of the subject is reduced after the composition is administered.

6. The method of claim 1, wherein a symptom of the ocular immunoinflammatory disorder is reduced
   (a) within 5, 15, 30, or 60 minutes after administering the composition begins; or
   (b) within 1, 2, 3, 4, 5, 6, 7, 8, 9, 10, 11, 12, 13, or 14 days after administering the composition begins.

7. The method of claim 1, wherein the composition is administered to the eye of the subject
   (a) less than 1, 2, 3, 4, 5, or 6 times per day;
   (b) about 1, 2, 3, 4, 5, 6, or 7 times per week; or
   (c) once daily.

8. The method of claim 1, wherein:
   (a) the compound that inhibits IL-7 signal transduction comprises an antibody that binds to IL-7; or
   (b) the compound that inhibits IL-15 signal transduction comprises an antibody that binds to IL-15.

9. The method of claim 1, wherein the composition consists of a neutralizing anti-IL-7R antibody or an antibody that binds to IL-7, and an ophthalmically acceptable excipient.

* * * * *